(12) United States Patent
Cooper et al.

(10) Patent No.: US 7,723,563 B2
(45) Date of Patent: May 25, 2010

(54) TRANSGENIC PROTEINS FROM MULTI-GENE SYSTEMS, METHODS, COMPOSITIONS, USES AND THE LIKE RELATING THERETO

(75) Inventors: Julian D. Cooper, Blacksburg, VA (US); Tanya K. O'Sickey, Terre Haute, IN (US); Stephen P. Butler, Blacksburg, VA (US)

(73) Assignee: Progenetics LLC, Blacksburg, VA (US)

( * ) Notice: Subject to any disclaimer, the term of this patent is extended or adjusted under 35 U.S.C. 154(b) by 1502 days.

(21) Appl. No.: 10/471,491

(22) PCT Filed: Mar. 11, 2002

(86) PCT No.: PCT/US02/07540

§ 371 (c)(1), (2), (4) Date: Feb. 12, 2004

(87) PCT Pub. No.: WO02/072024

PCT Pub. Date: Sep. 19, 2002

(65) Prior Publication Data

US 2004/0133932 A1    Jul. 8, 2004

Related U.S. Application Data

(60) Provisional application No. 60/274,983, filed on Mar. 12, 2001.

(51) Int. Cl.
*C12P 21/00* (2006.01)
*A01K 67/00* (2006.01)

(52) U.S. Cl. ............................................... 800/4; 800/8

(58) Field of Classification Search .................... 800/4, 800/8

See application file for complete search history.

(56) References Cited

U.S. PATENT DOCUMENTS 5,756,687 A * 5/1998 Denman et al. ............. 530/412

FOREIGN PATENT DOCUMENTS

WO  WO94/05796 A1  3/1994
WO  WO/99/01549 A1  1/1999

OTHER PUBLICATIONS

Ianilovitch, E et al. Mole Cancer Res 1:32-47, 2002.*
Liu, X et al. PNAS 92:9931-8835,1995.*
Campbell, SM et al. Nucleic Acid Reseach 12(22):8685-8697.*
Ambrosio et al. Gene 385:311-318, 2002.*
Naito et al. J Reprod Pert 113:137-143, 1998.*

* cited by examiner

*Primary Examiner*—Thaian N Ton
*Assistant Examiner*—Marcia S Noble
(74) *Attorney, Agent, or Firm*—Cooley Godward Kronish LLP

(57) ABSTRACT

A non-human transgenic mammalian animal, as described above, contains one or more exogenous double stranded DNA sequence(s) stably integrated into the genome of the animal, which comprises trans-acting regulatory units controlling expression of DNA sequences encoding proteins to be secreted into the milk of transgenic mammals. The DNA sequence of the trans-regulatory gene encodes transcriptional activating proteins, which are not secreted but made in a temporally controlled and mammary tissue specific manner. The DNA sequence containing the protein to be secreted in the milk is constructed on a separate gene sequence under the regulation of a minimal promoter and a trans-activation binding domain. The transgenic mammals are preferably pigs, cows, sheep, goats and rabbits. A related composition and method for making transgenic proteins which require specialized propeptides for proper post-translational processing is also described.

38 Claims, 23 Drawing Sheets

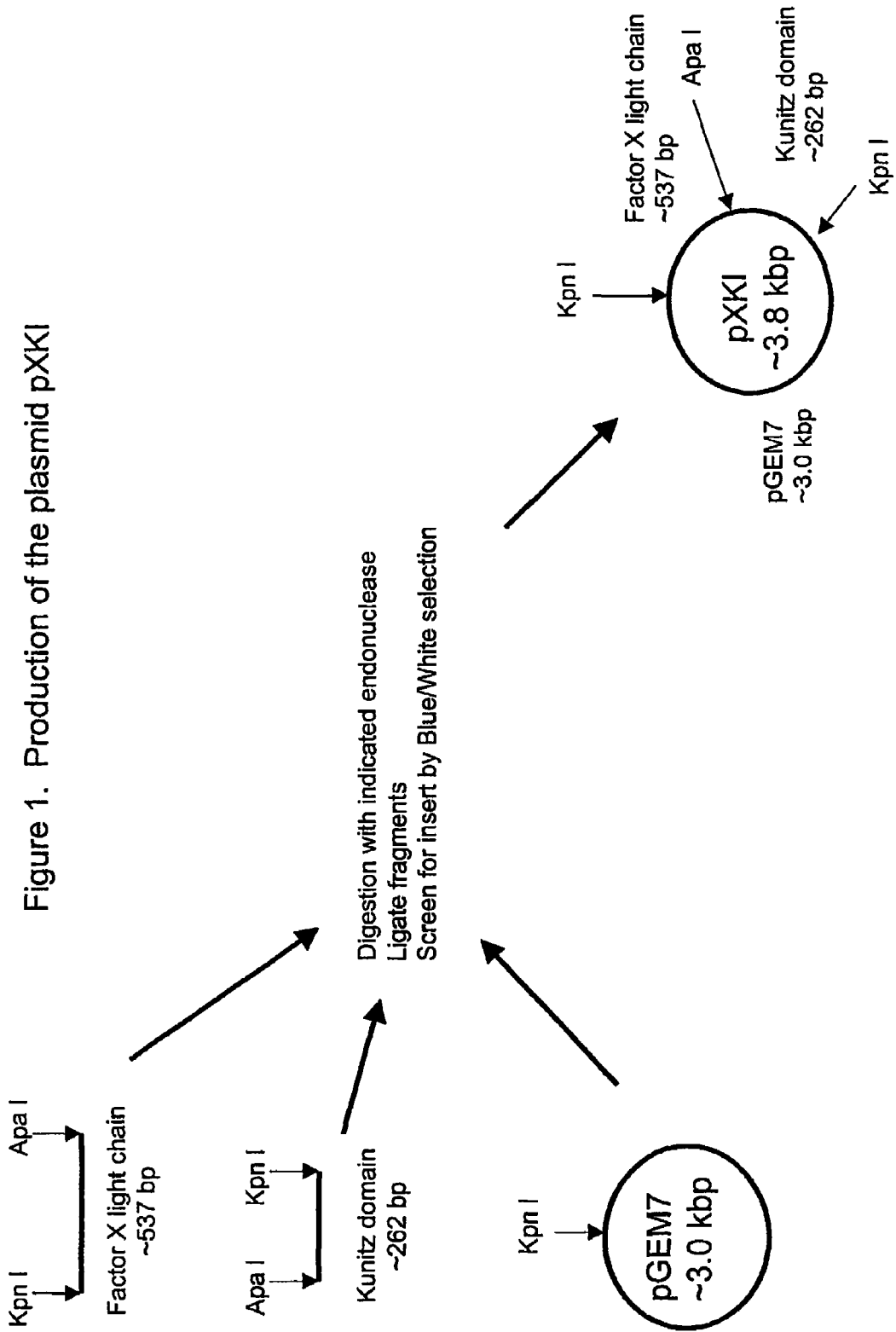
Figure 1. Production of the plasmid pXKI

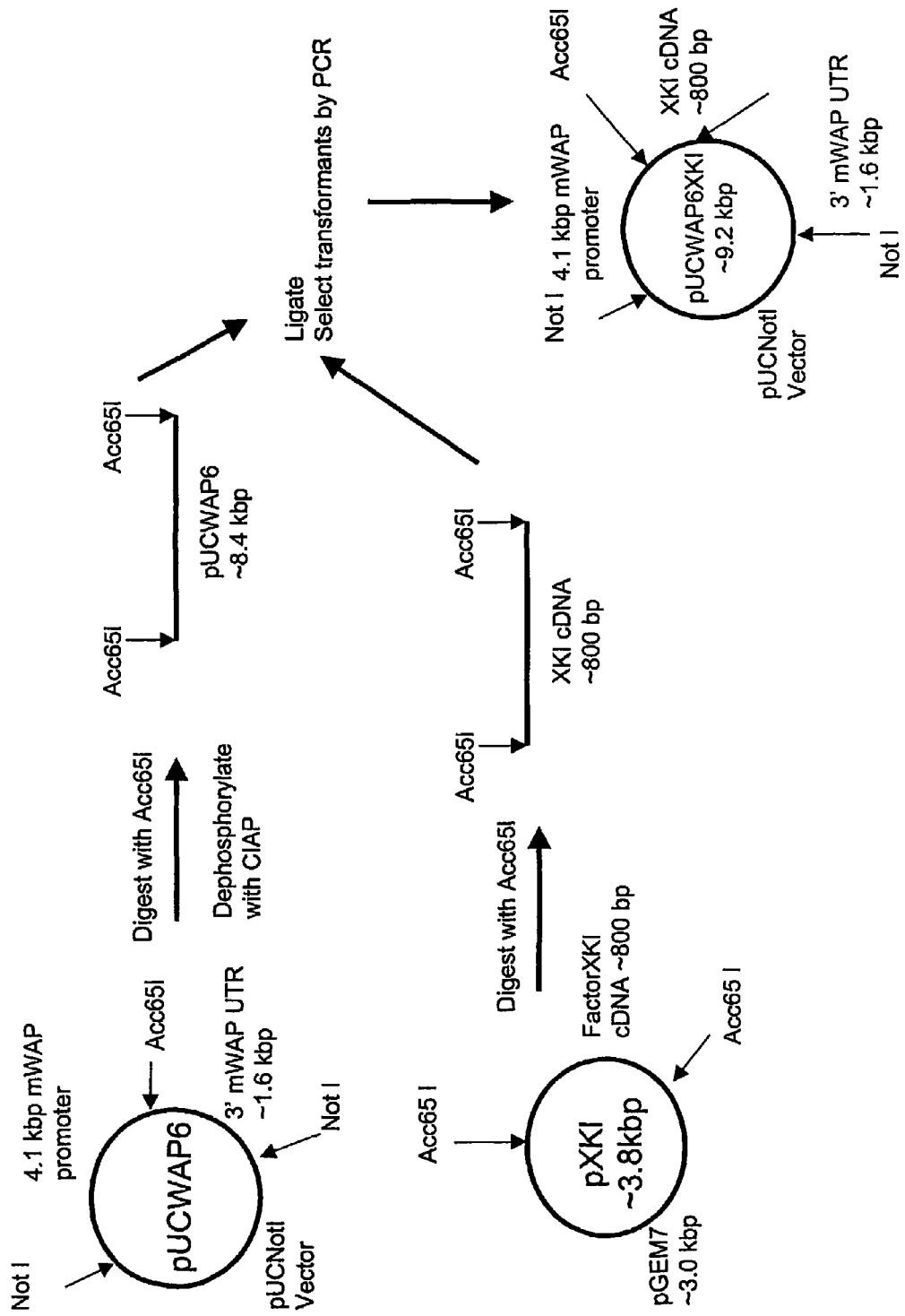
Figure 2. Production of the plasmid pUCWAPFXKI

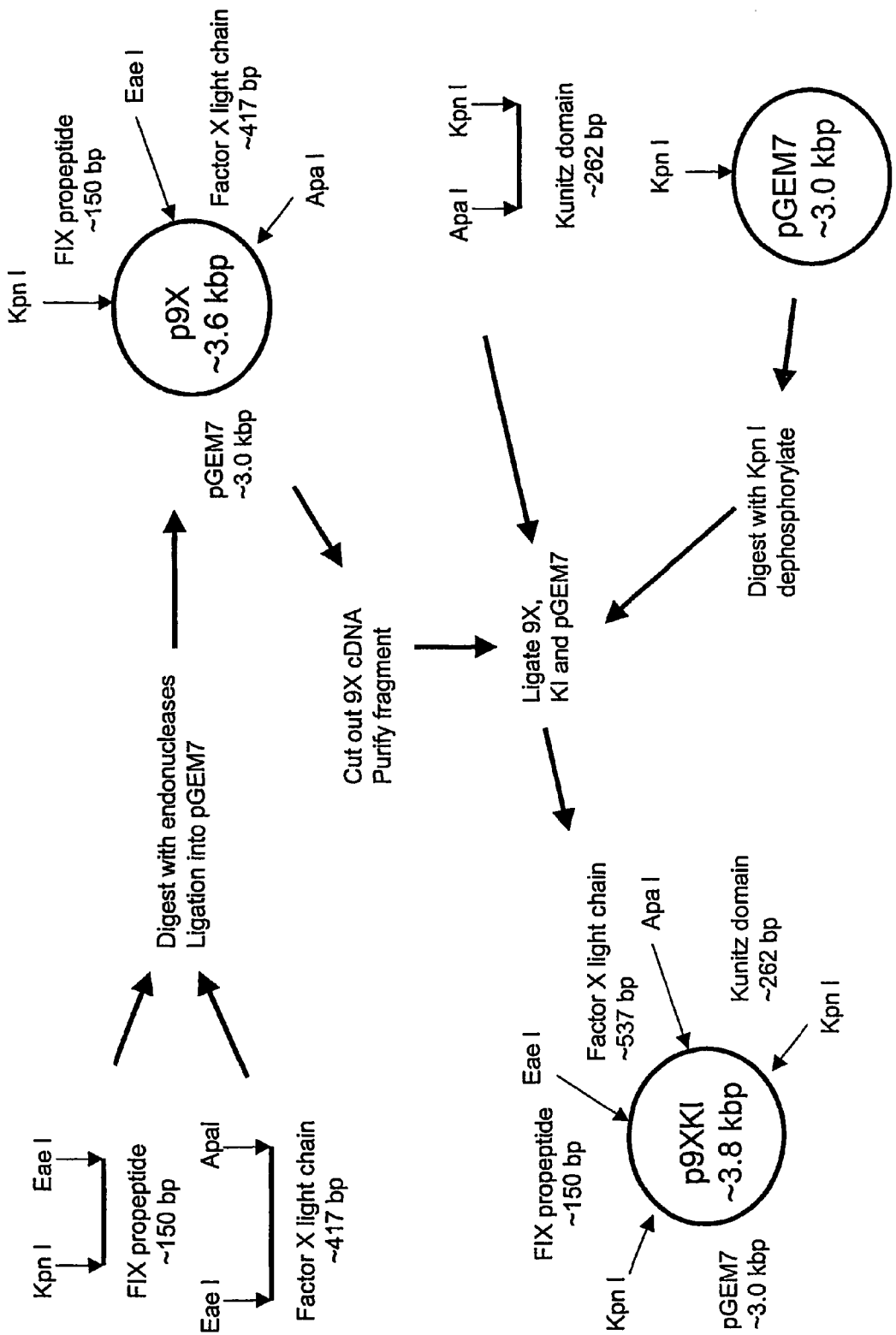
Figure 3. Production of the plasmid p9XKI

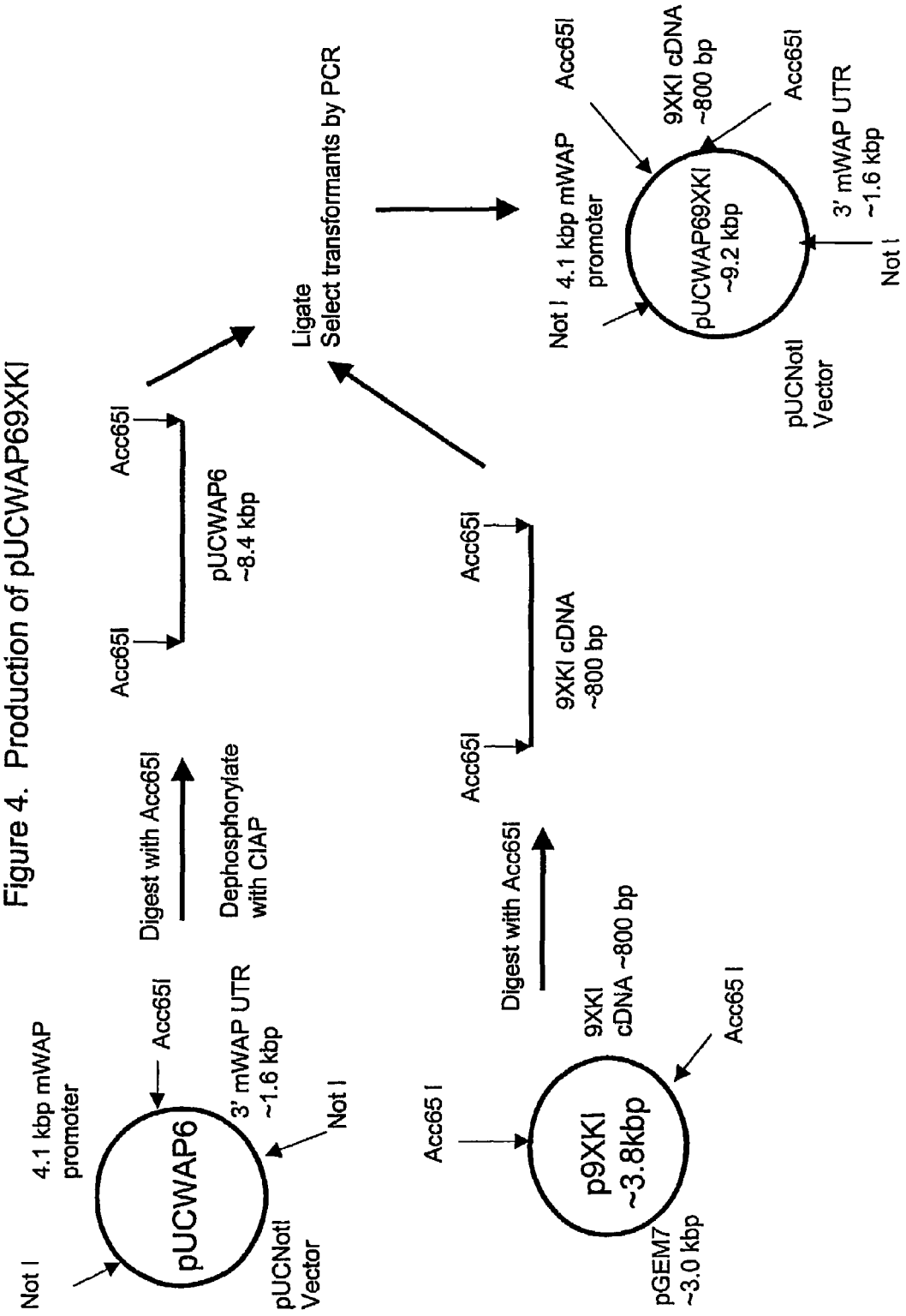

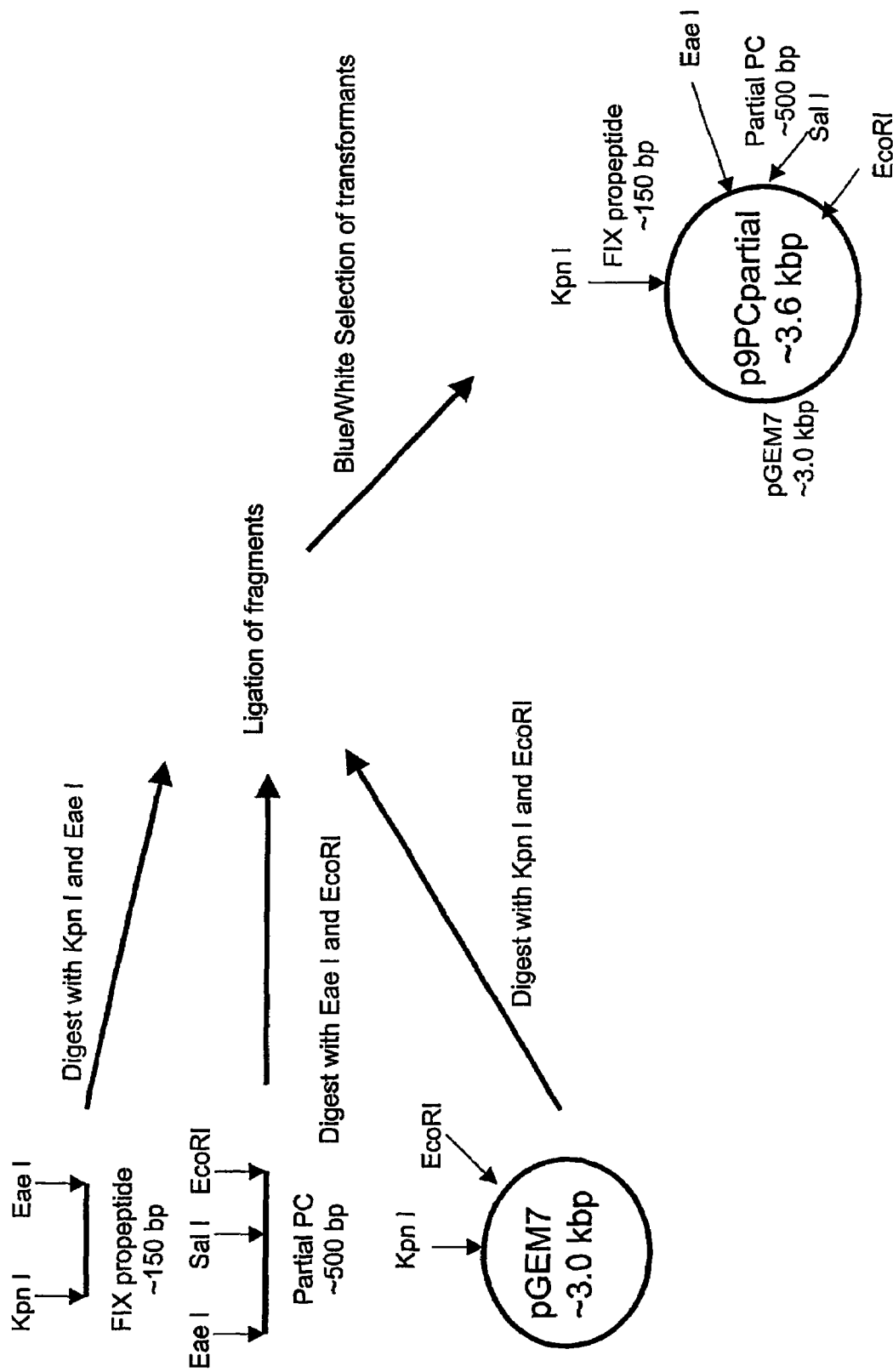
Figure 5. Production of p9PCpartial

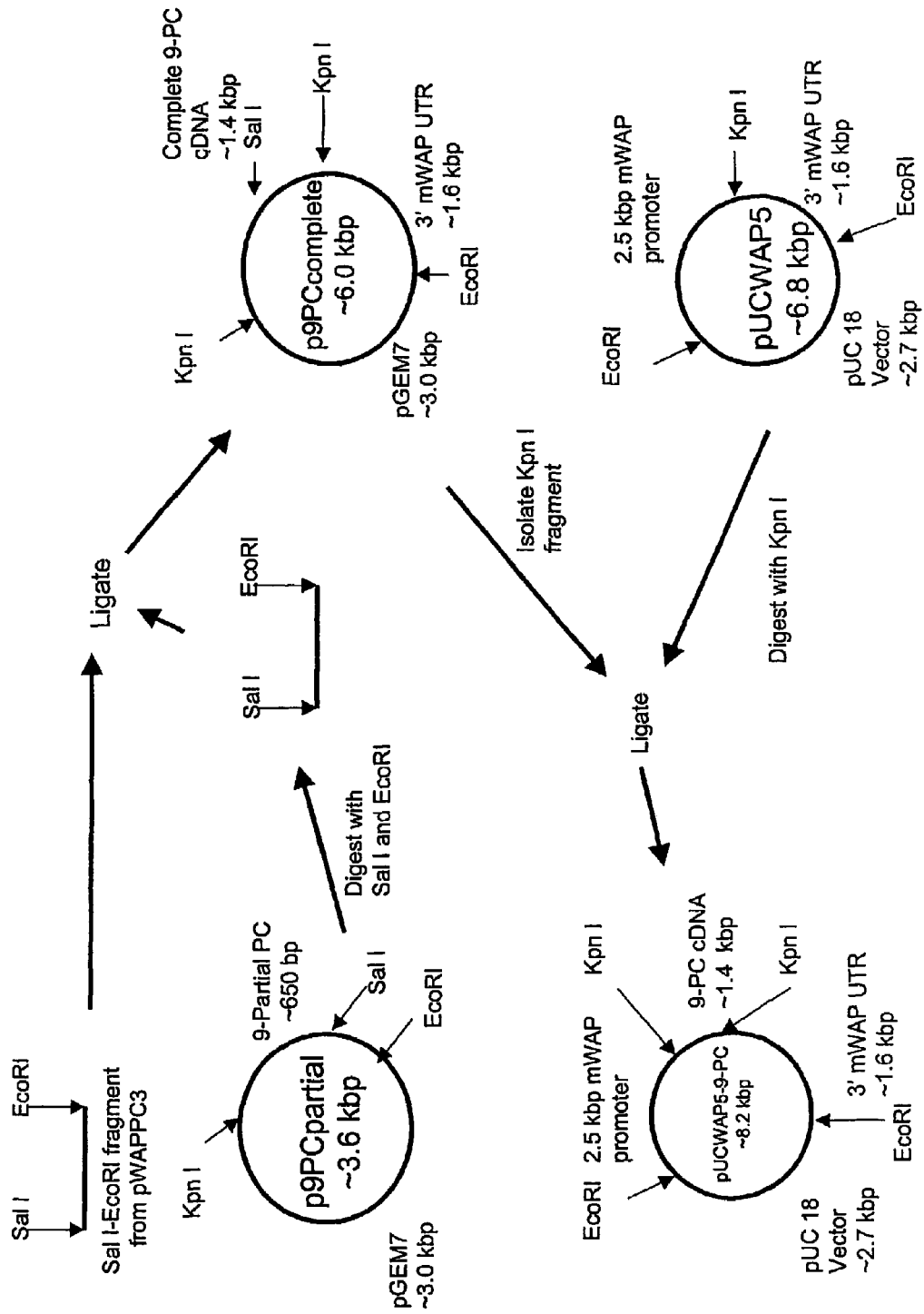
Figure 6. Production of pUCWAP5-9-PC

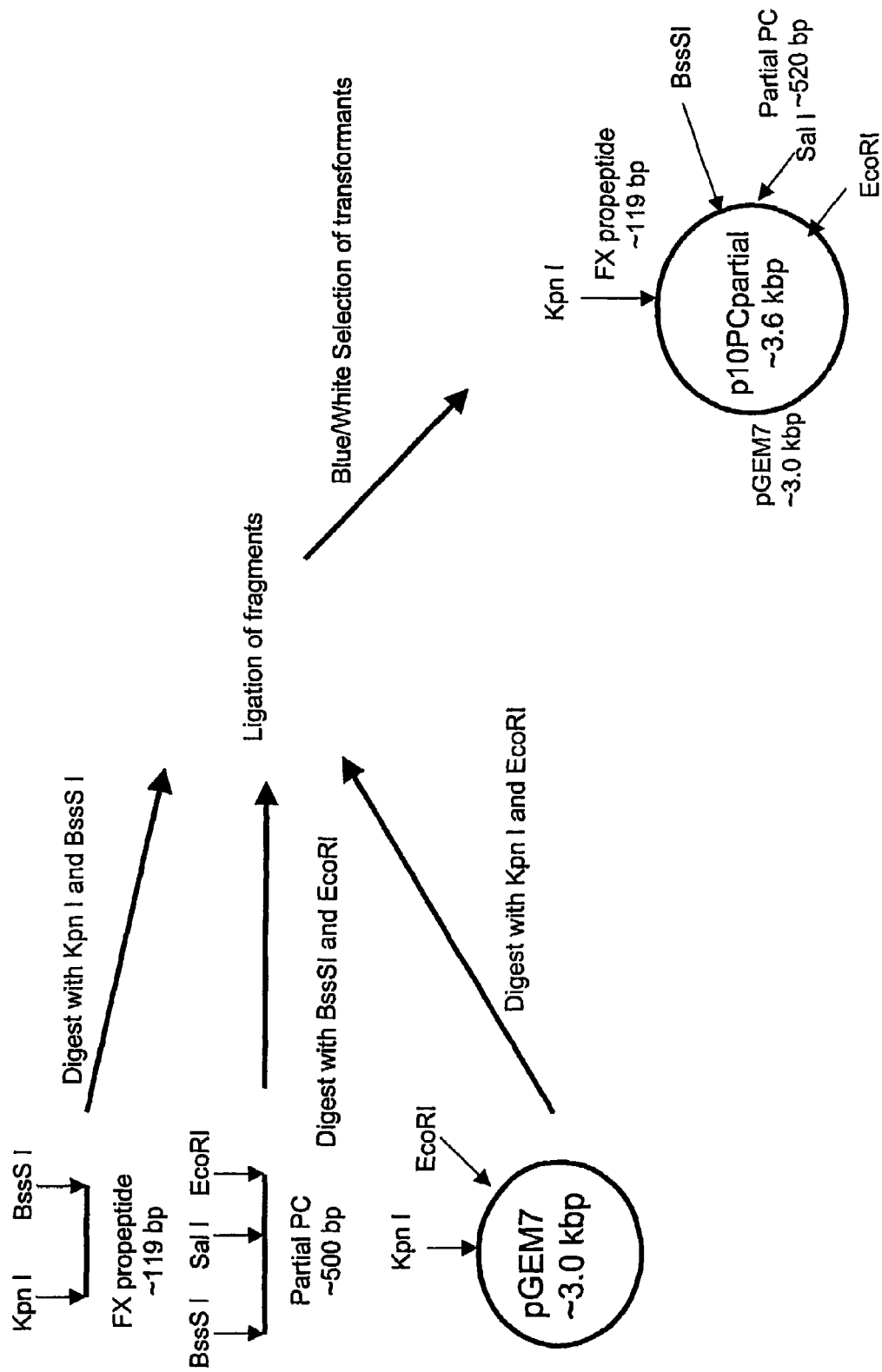
Figure 7. Production of p10PCpartial

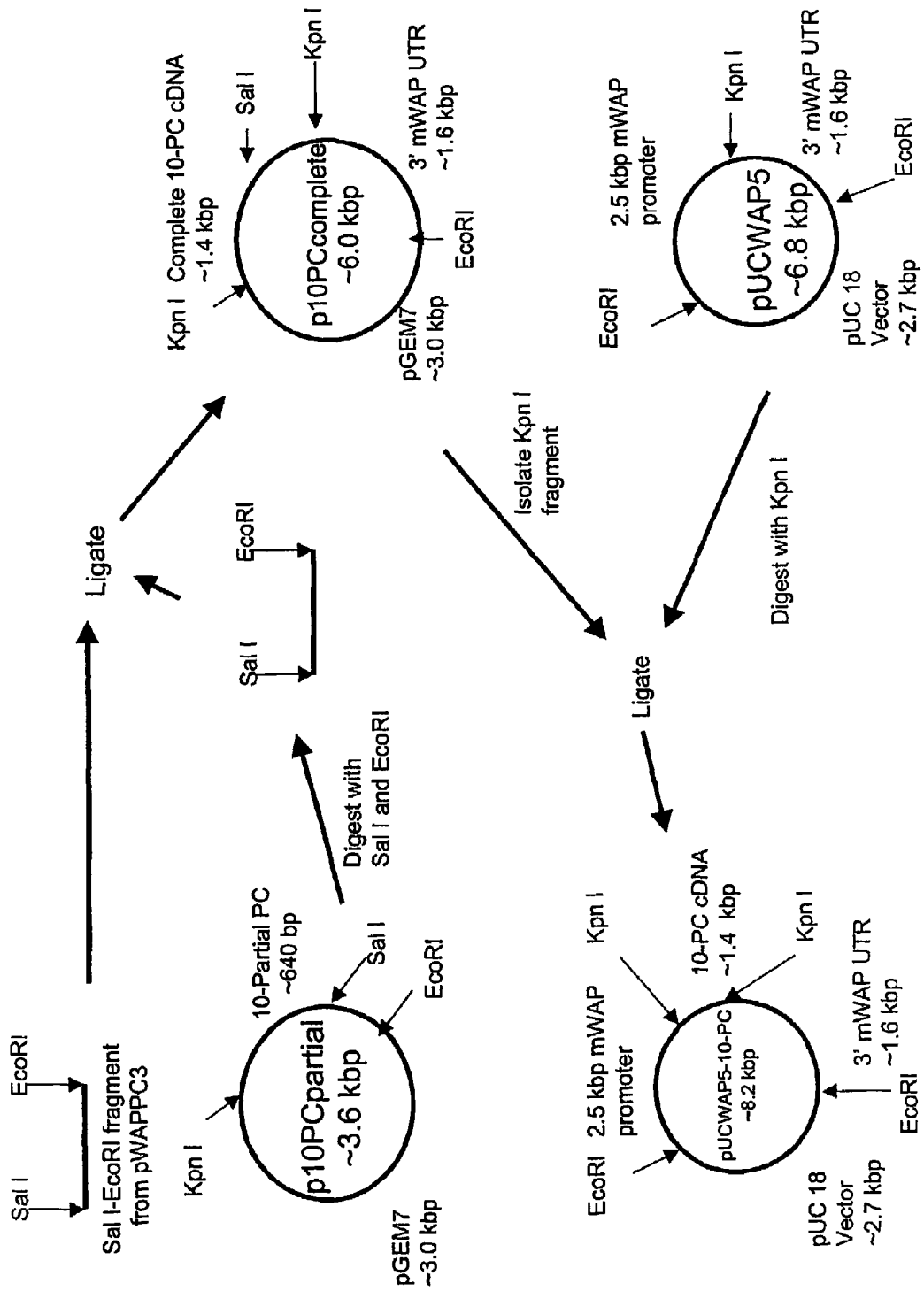
Figure 8. Production of pUCWAP5-10-PC

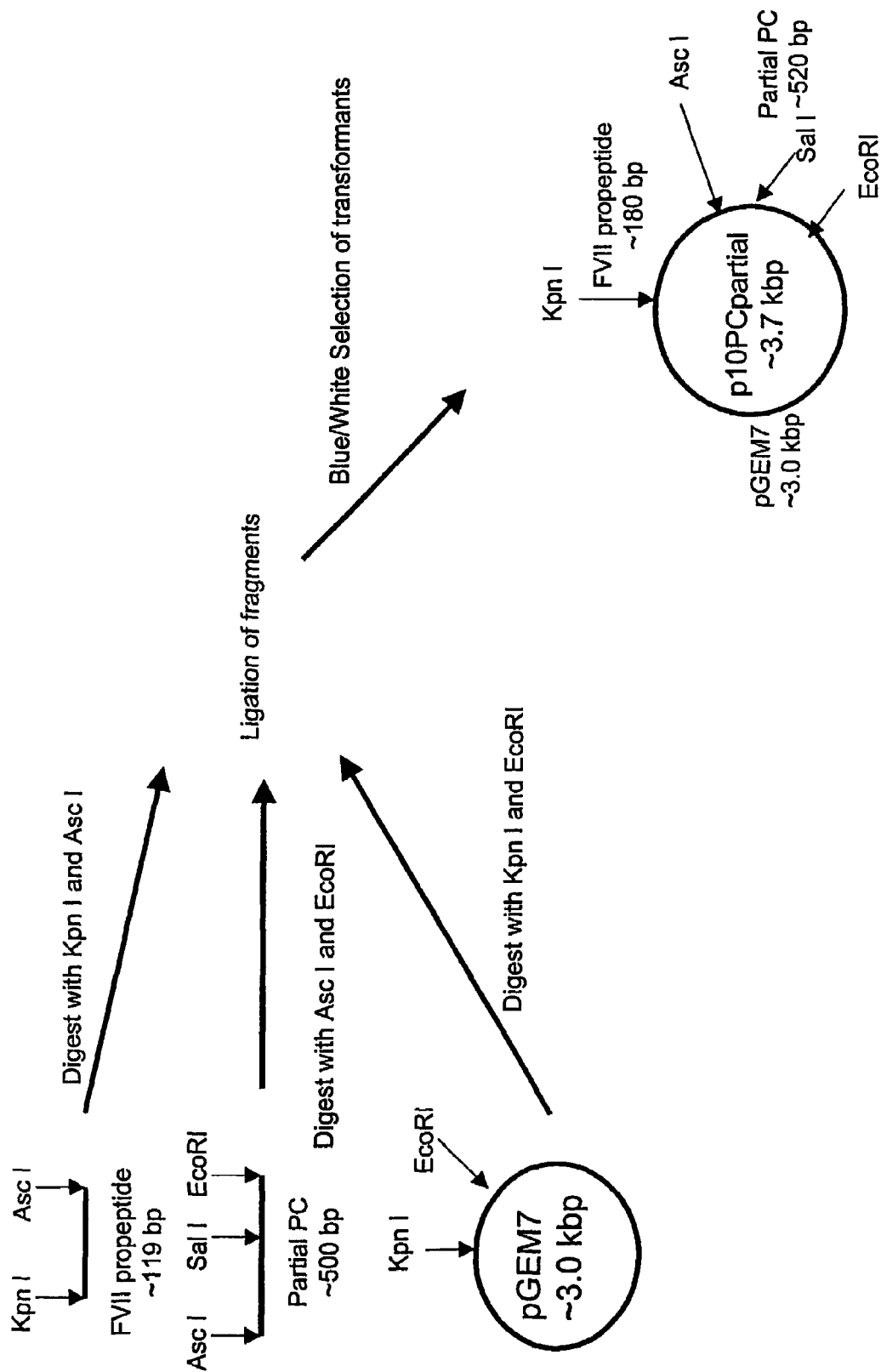

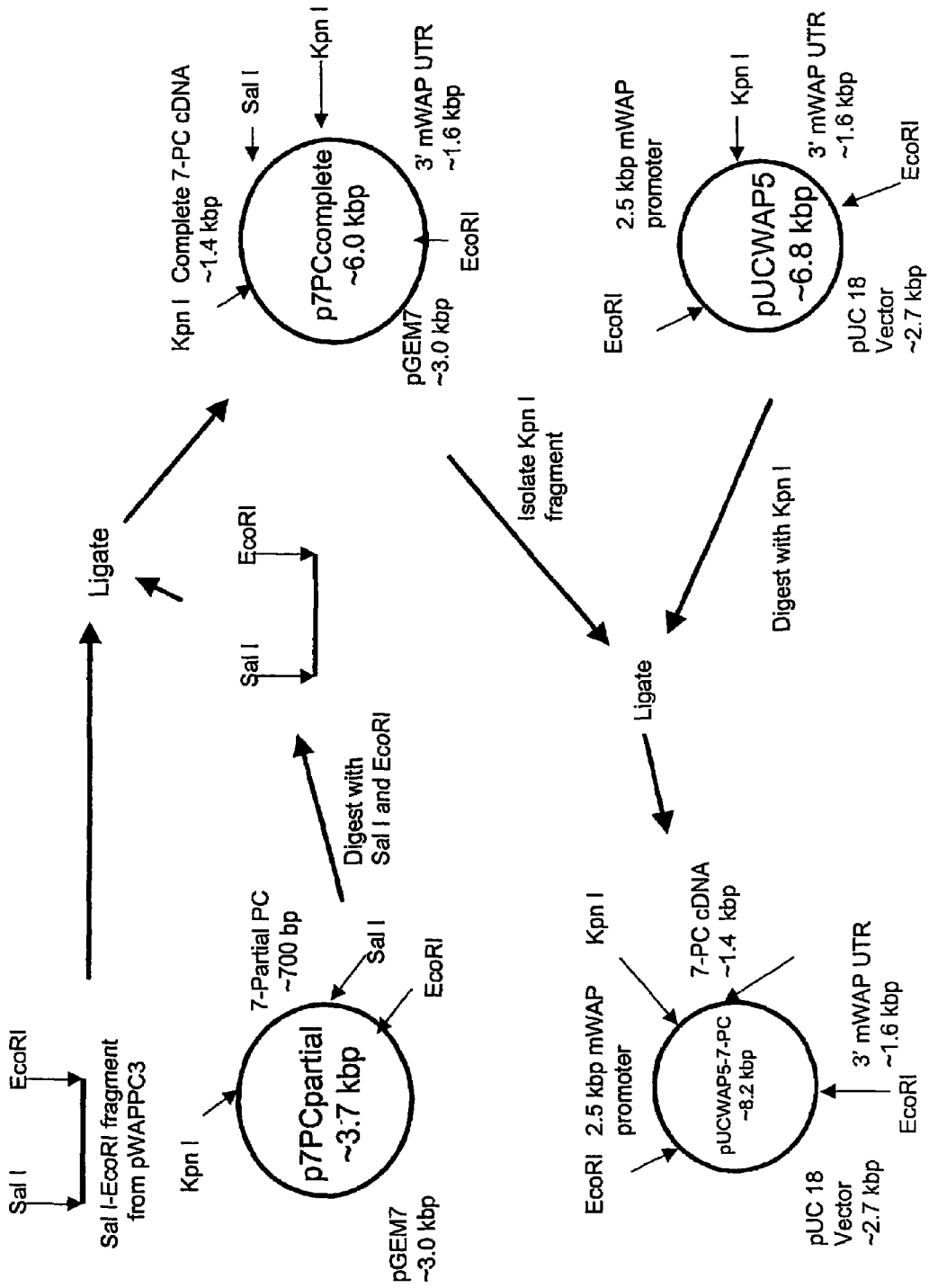
Figure 10. Production of pUCWAP5-7-PC

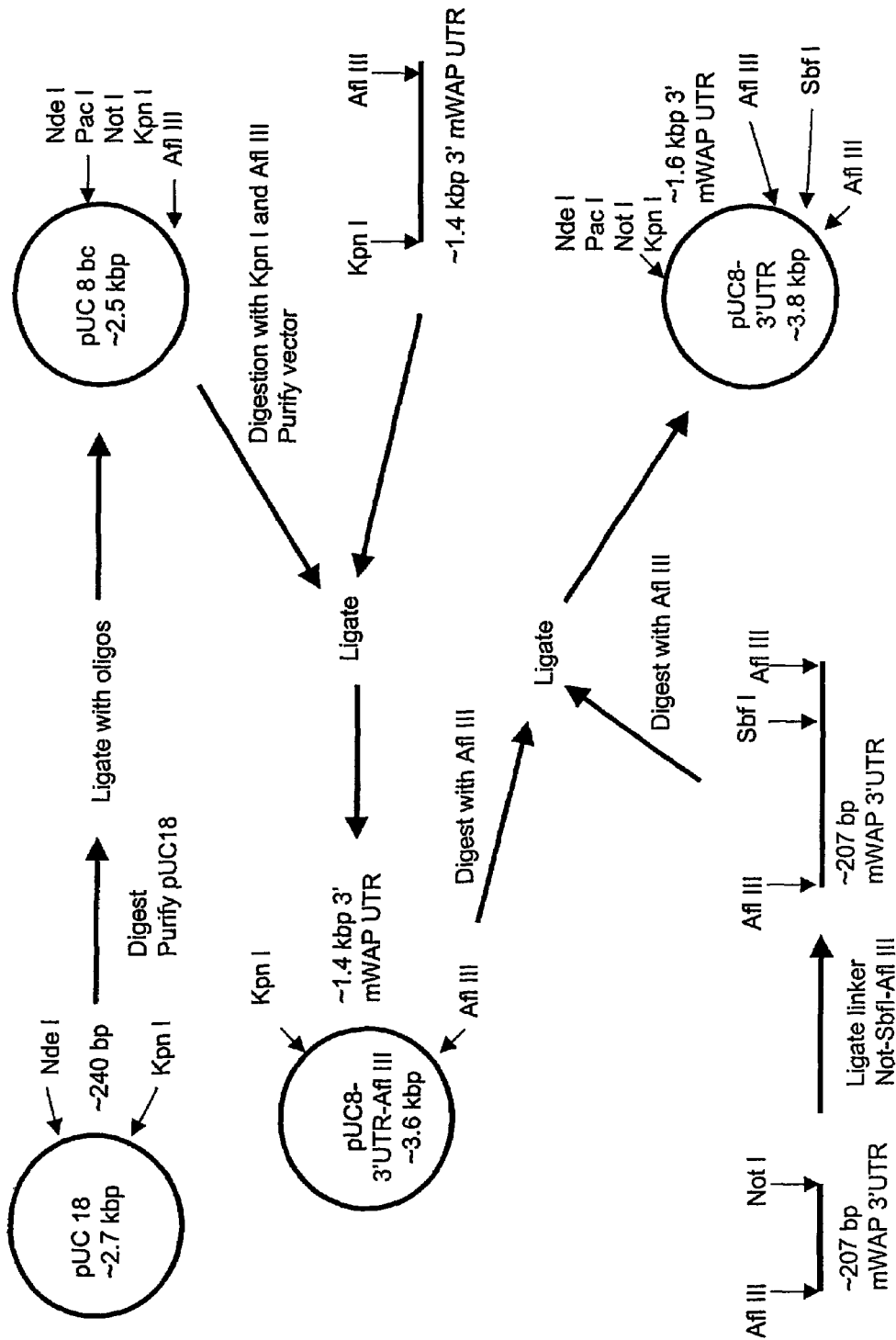
Figure 11. Production of pUC8-3'UTR

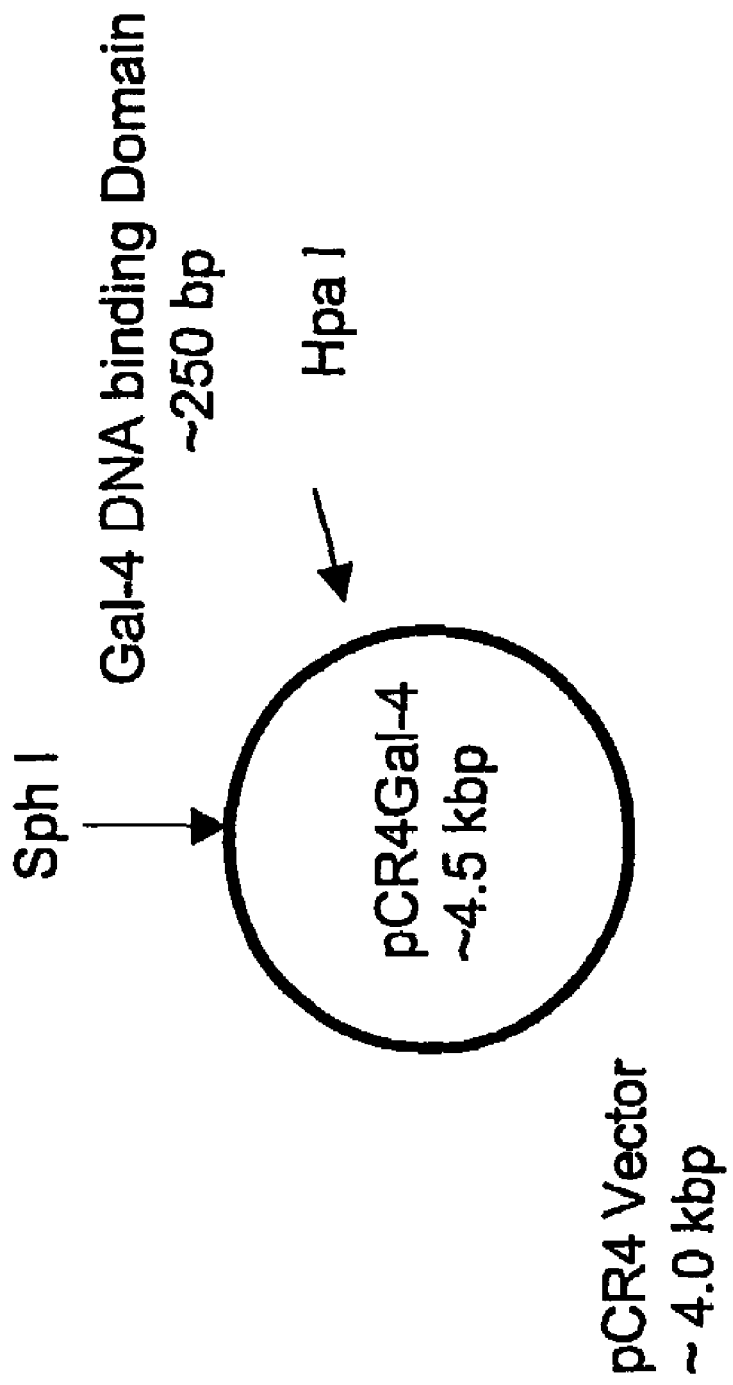
Figure 12. pCR4Gal-4

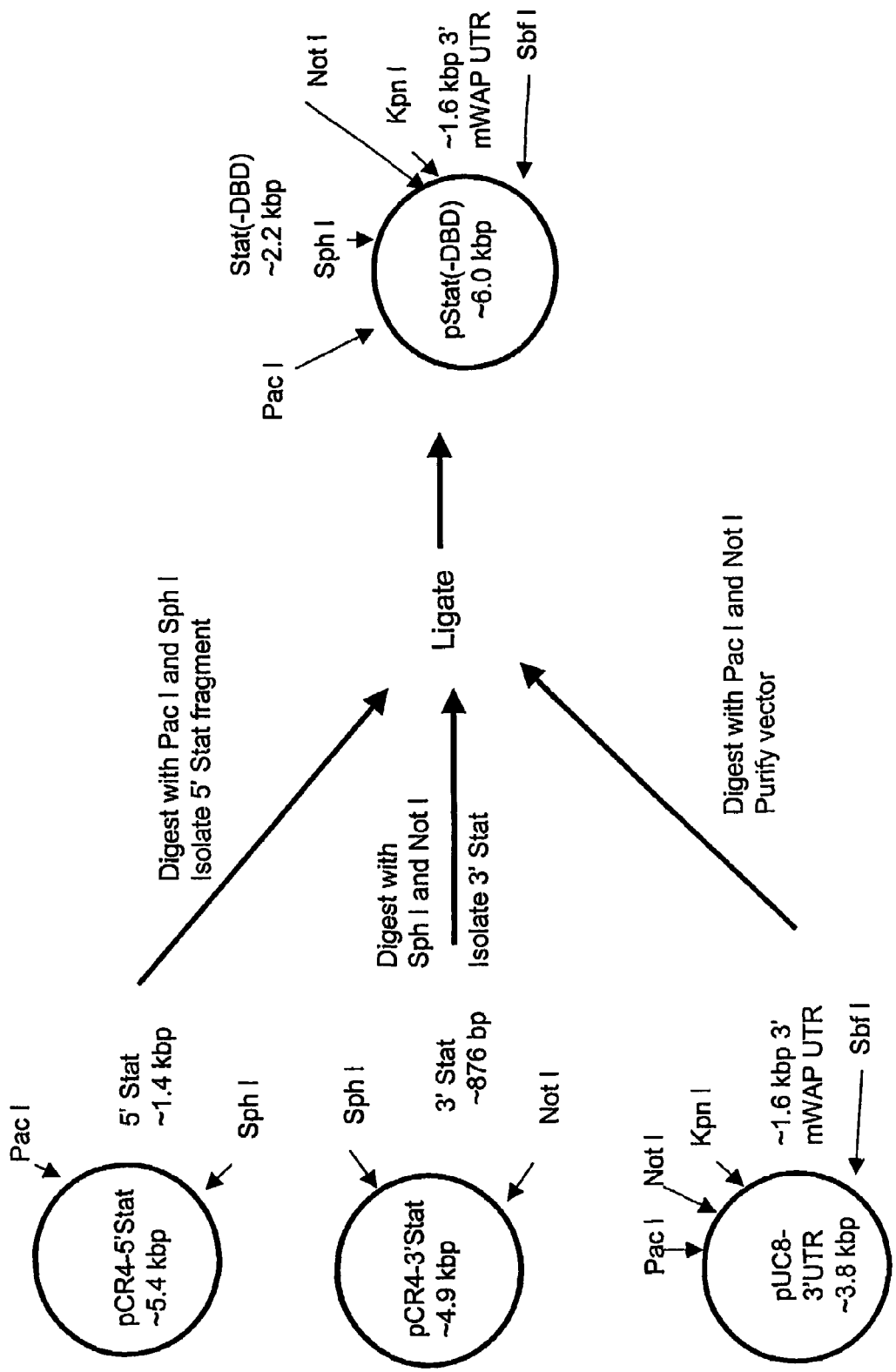
Figure 13. Production of pStat(-DBD)

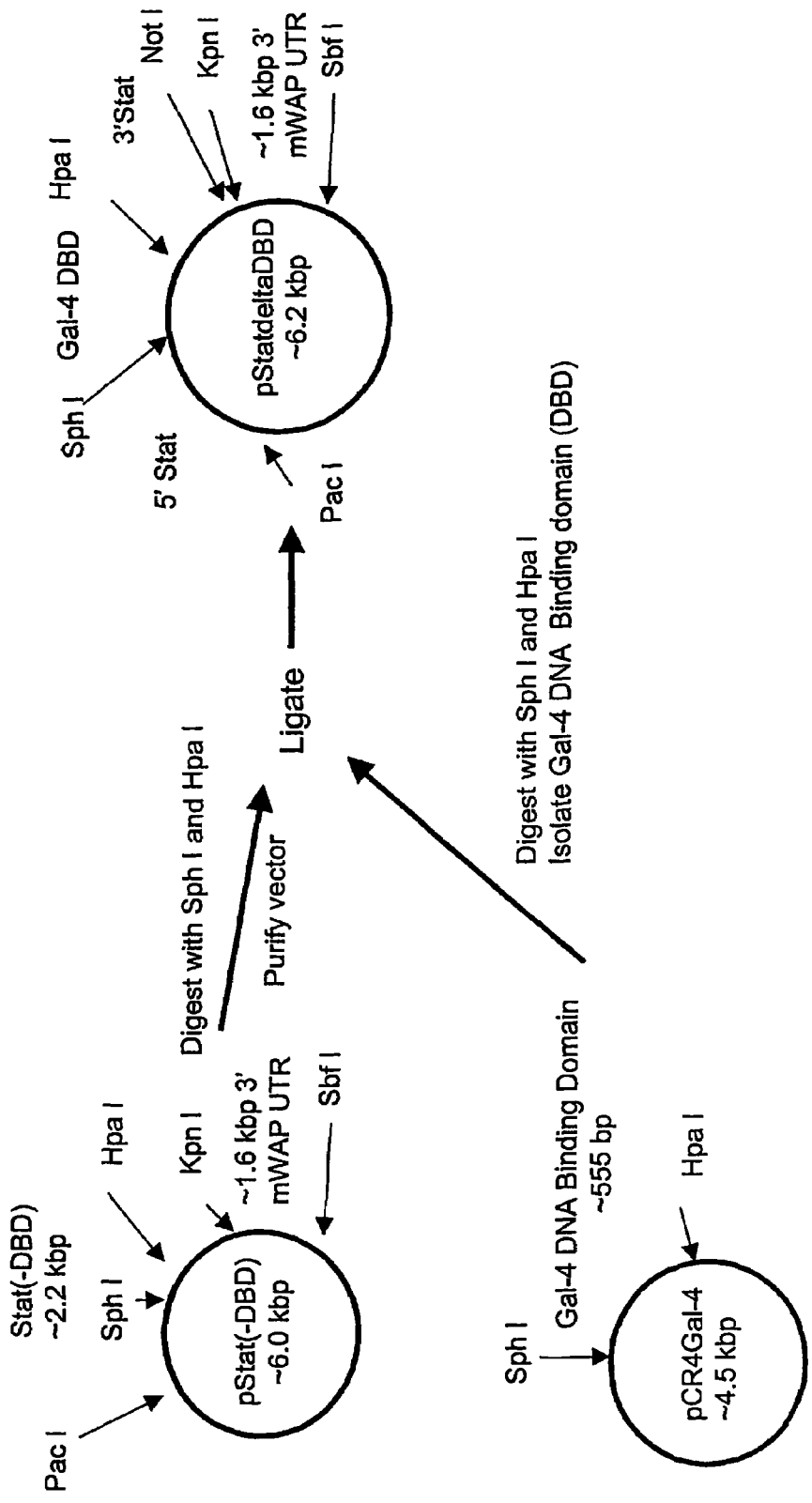
Figure 14. Production of pStatdeltaDBD

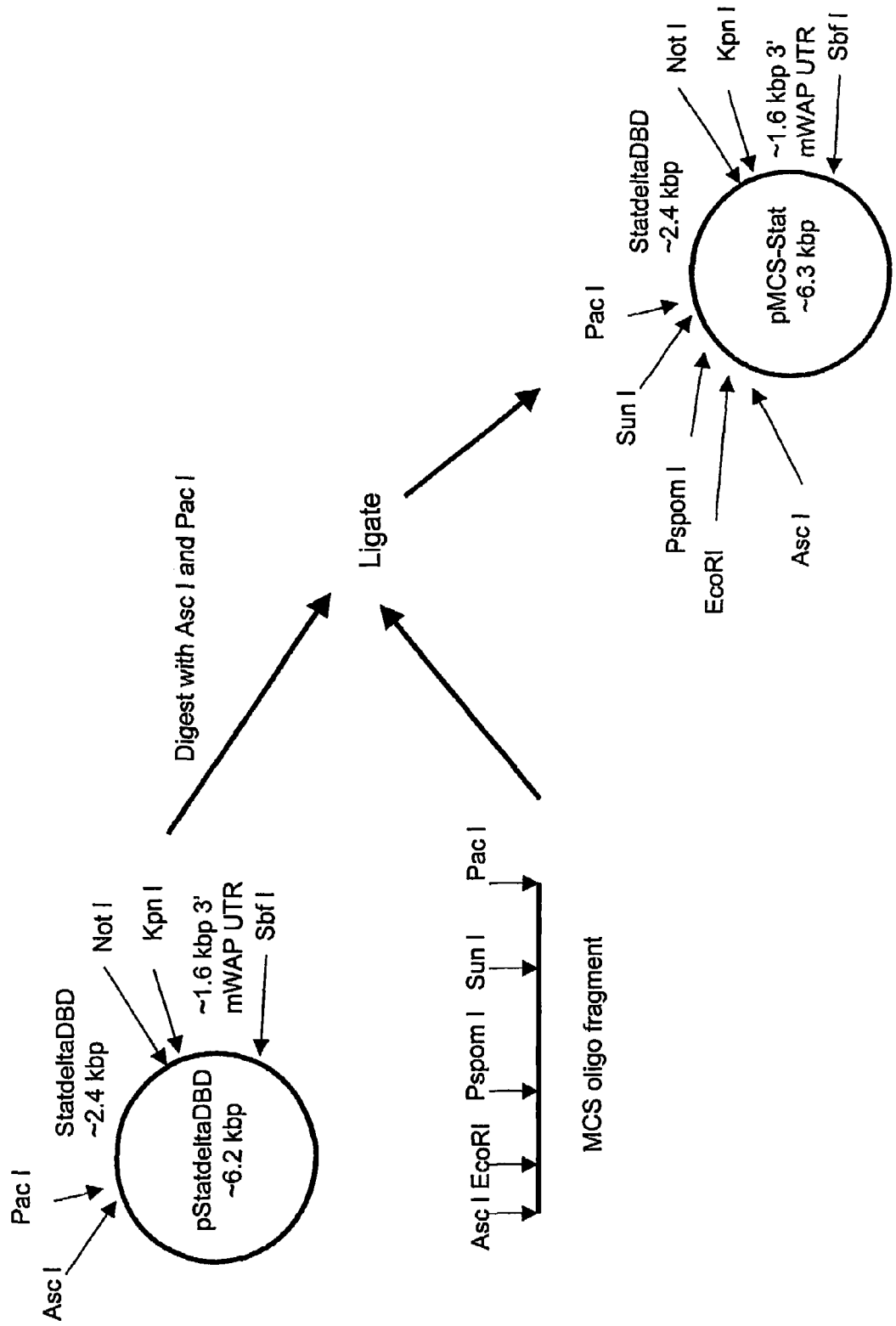
Figure 15. Production of MCS-Stat

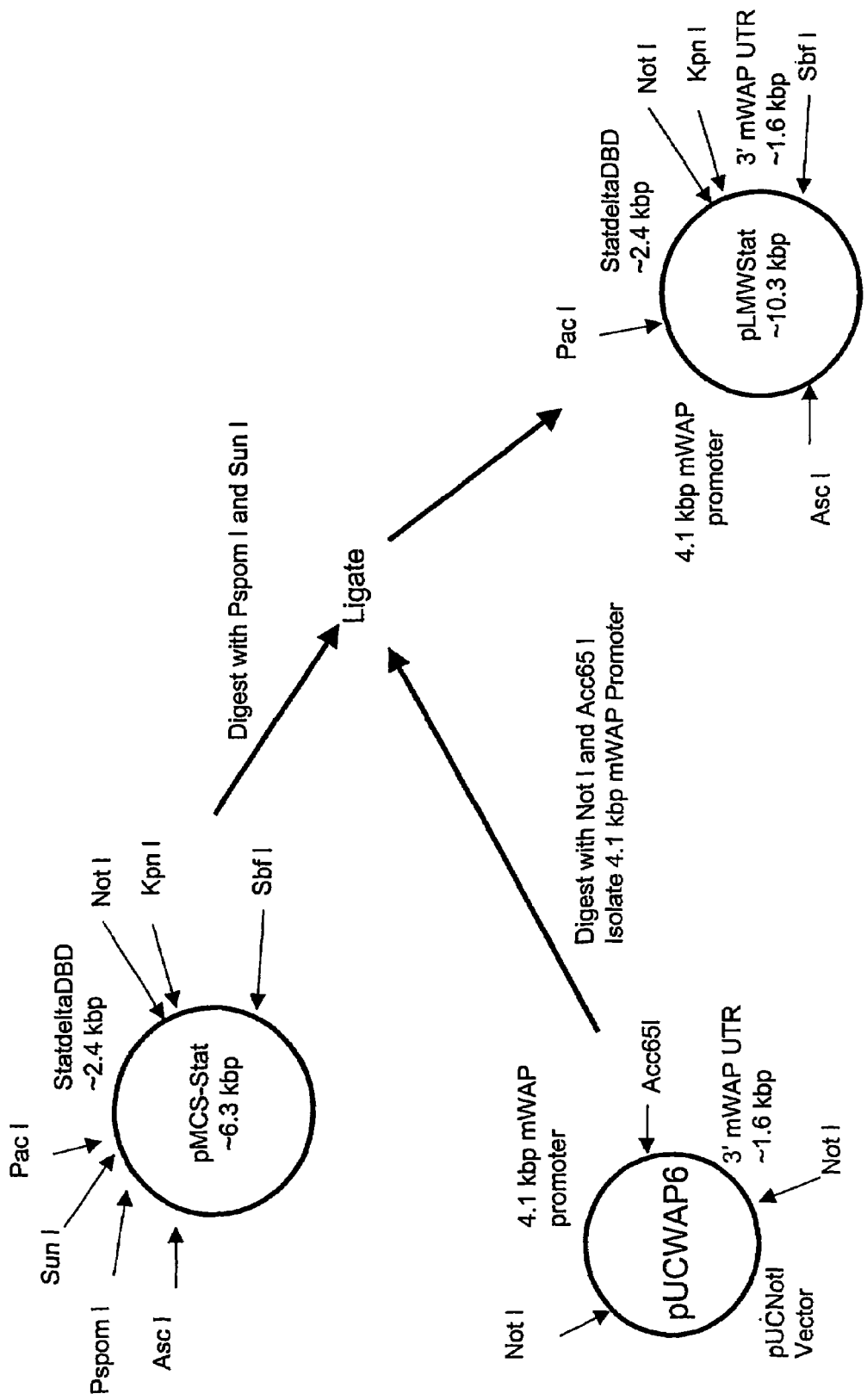
Figure 16. Production of pLMWStat

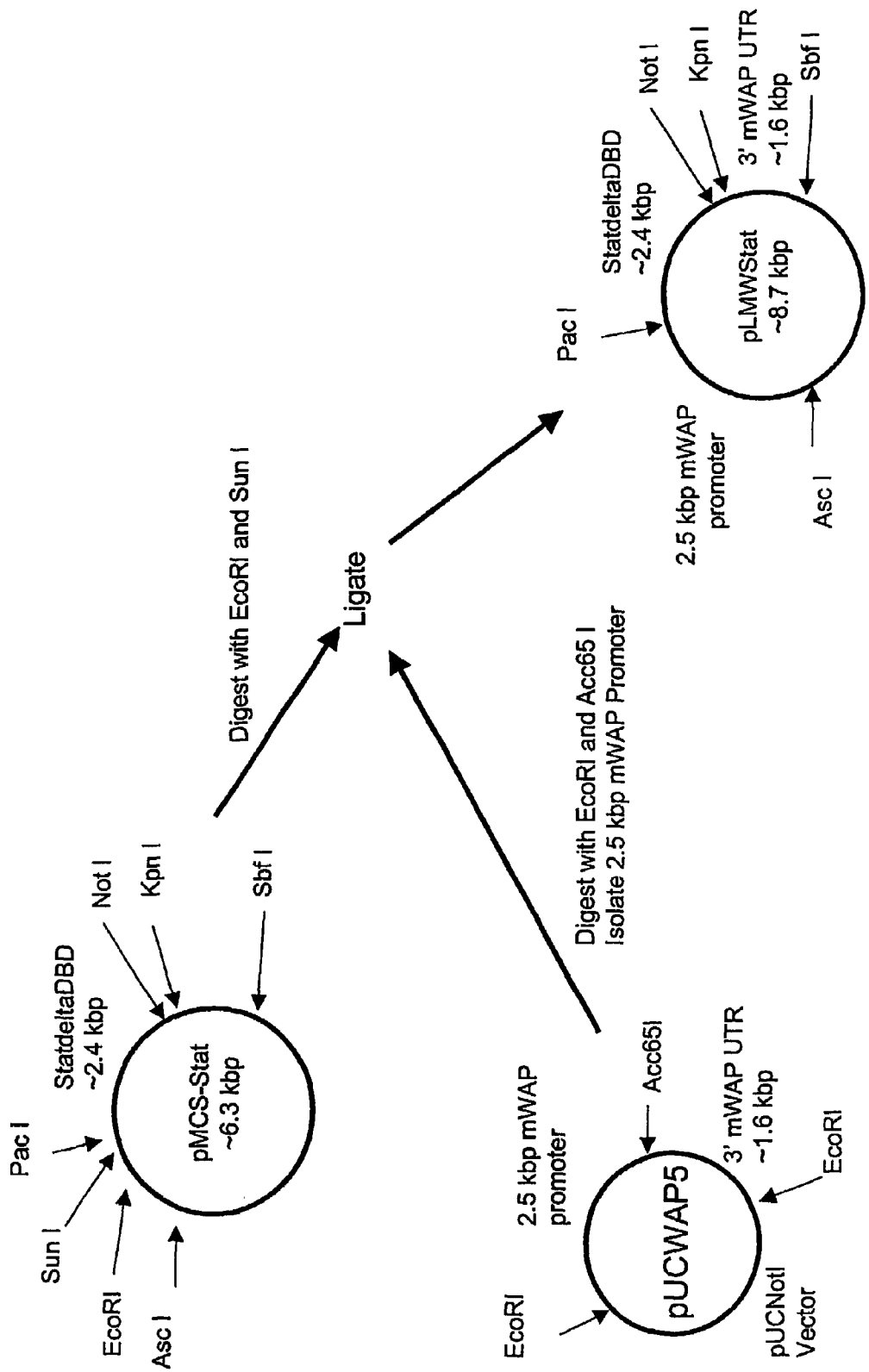
Figure 17. Production of pSMWStat

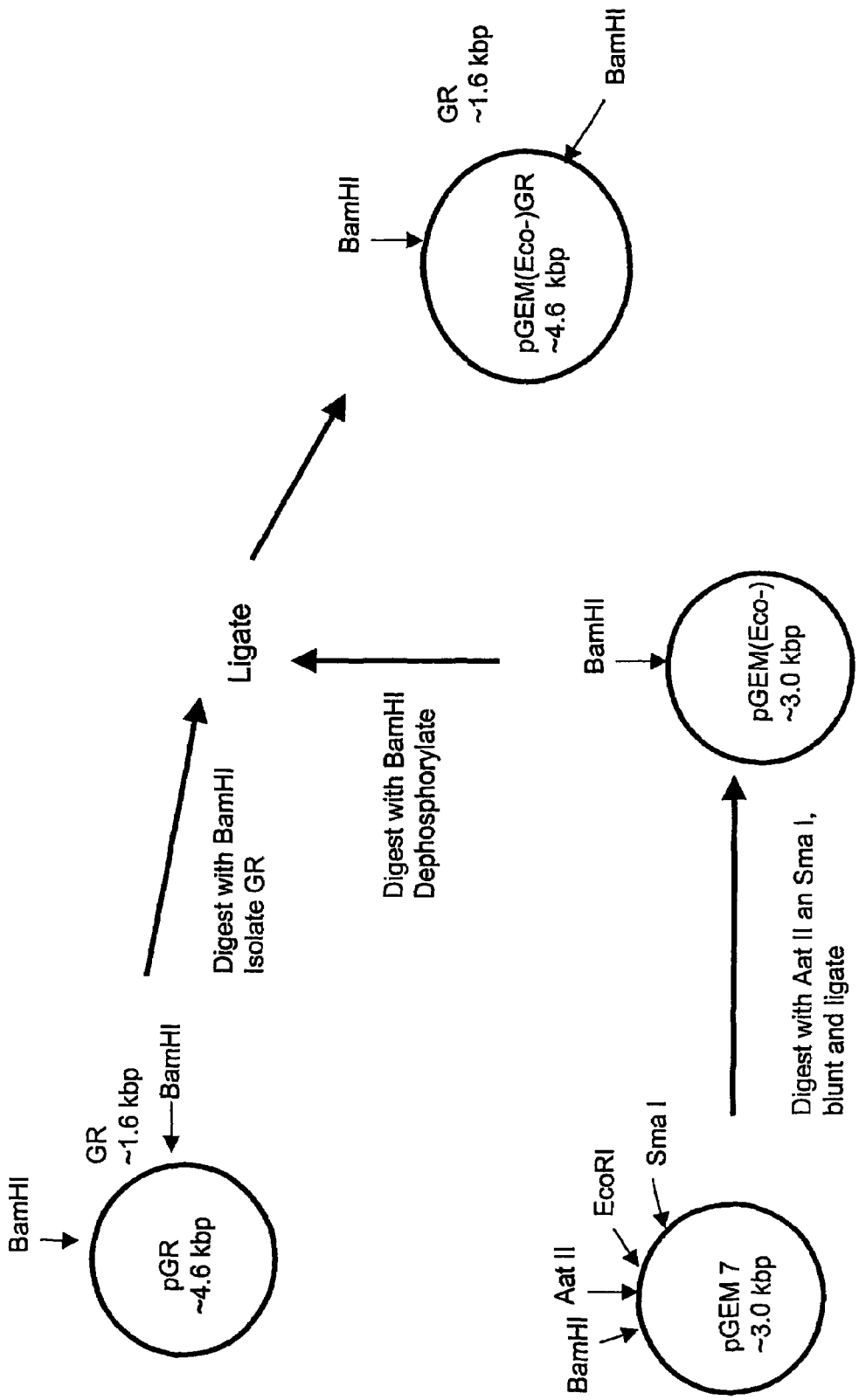
Figure 18. Production of pGem(Eco-)GR

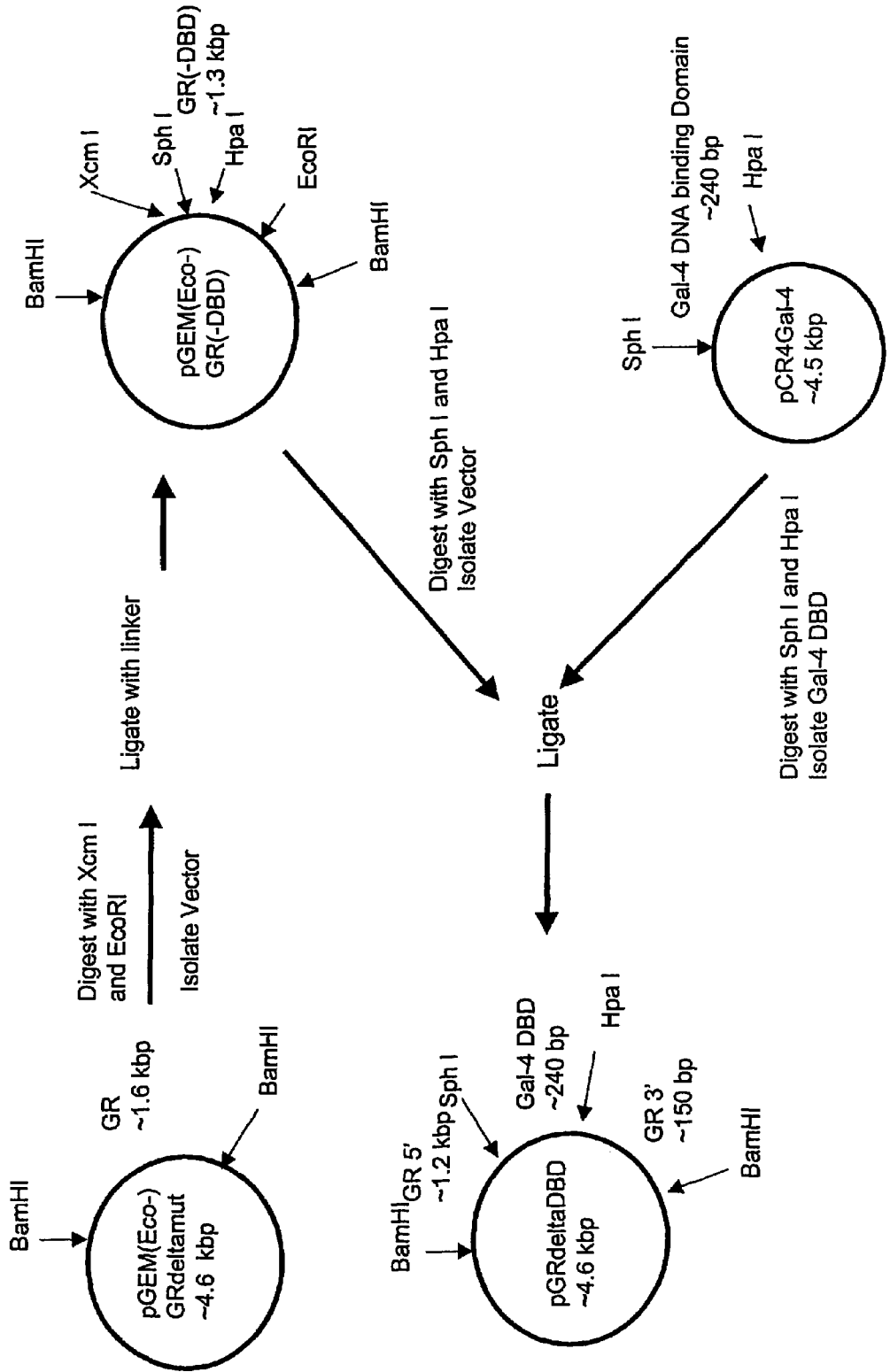
Figure 19. Production of the plasmid pGRdeltaDBD

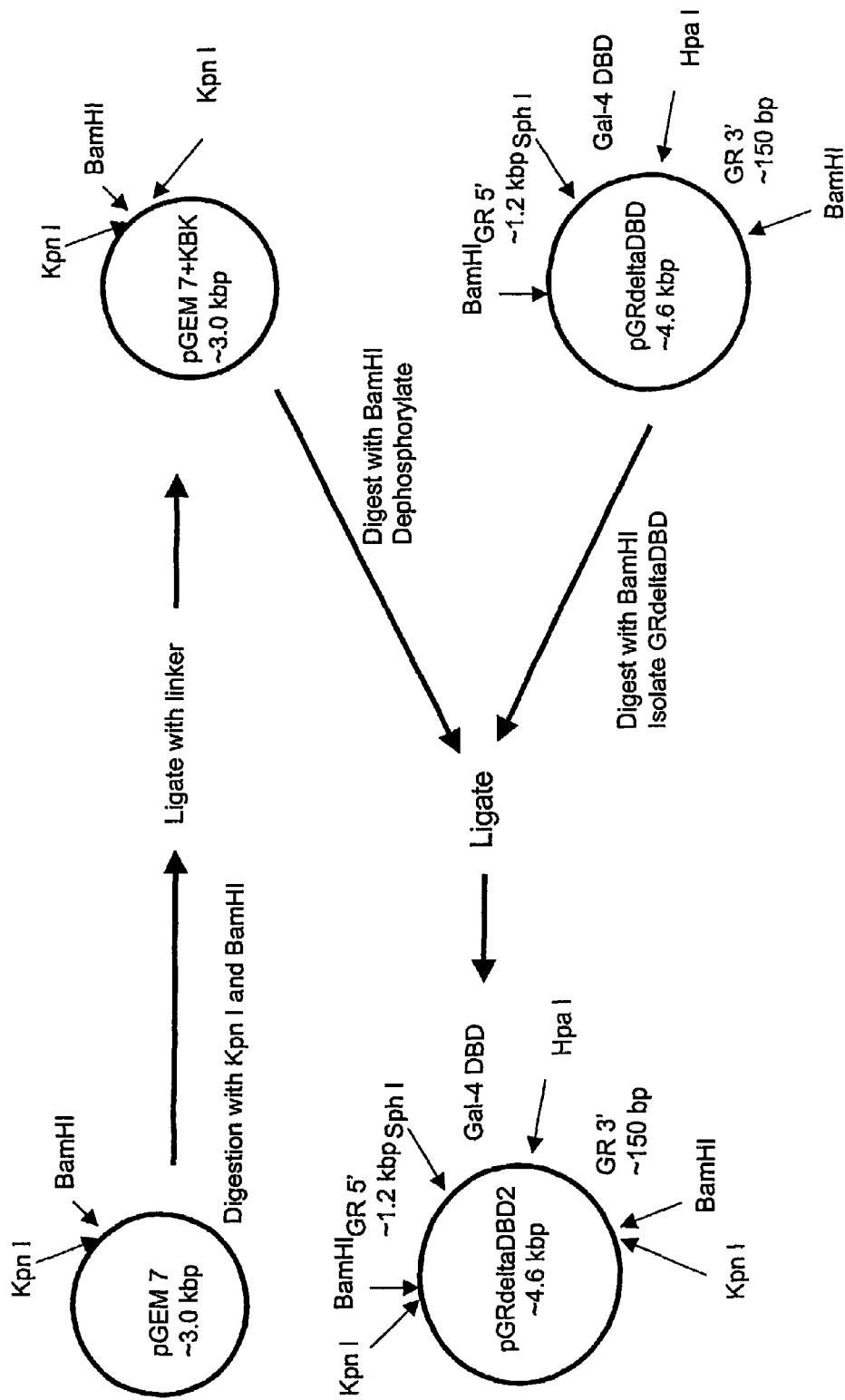

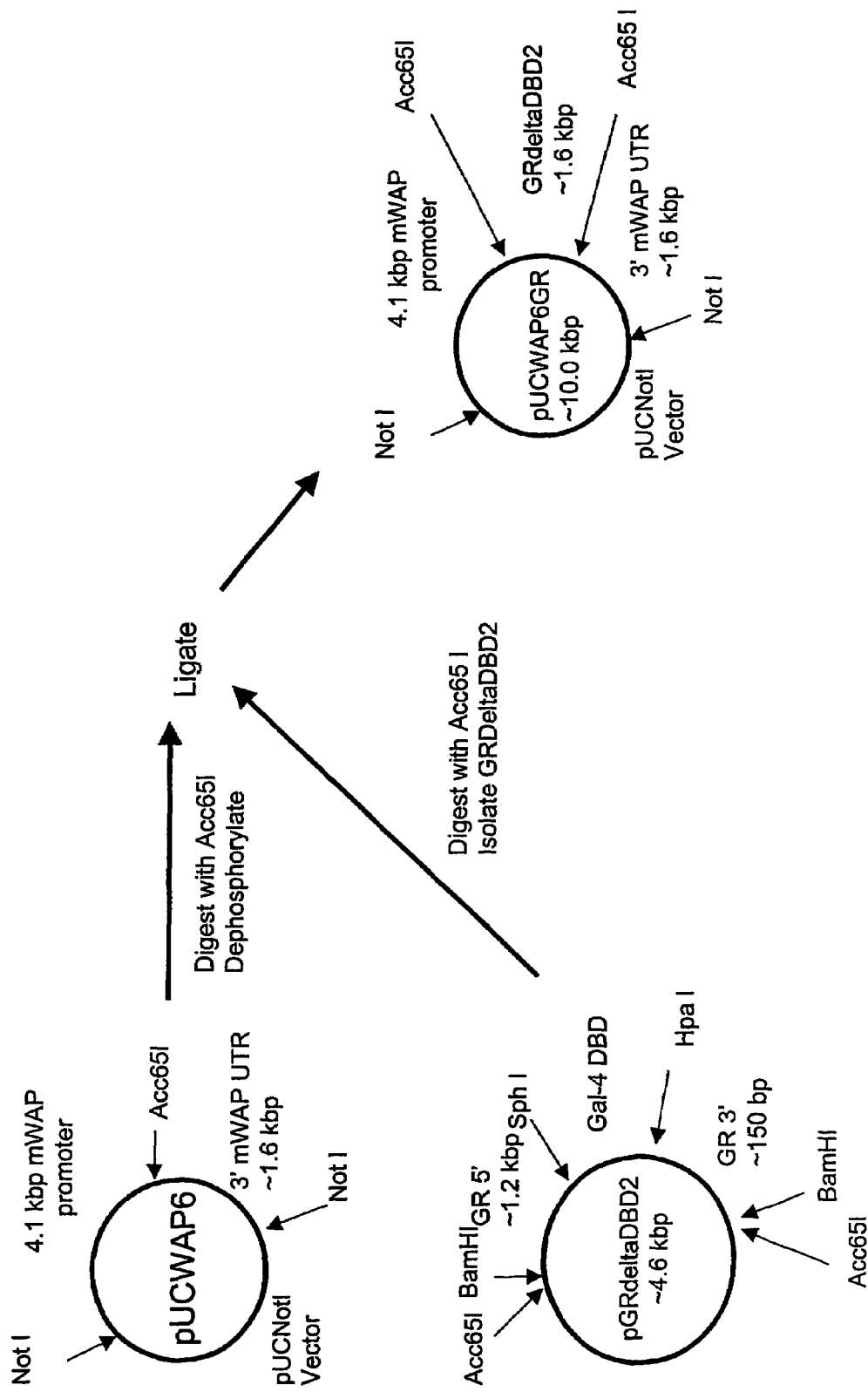
Figure 21. Production of pUCWAP6GR

Figure 22. Production of the minimum promoter cassette vector pMPC

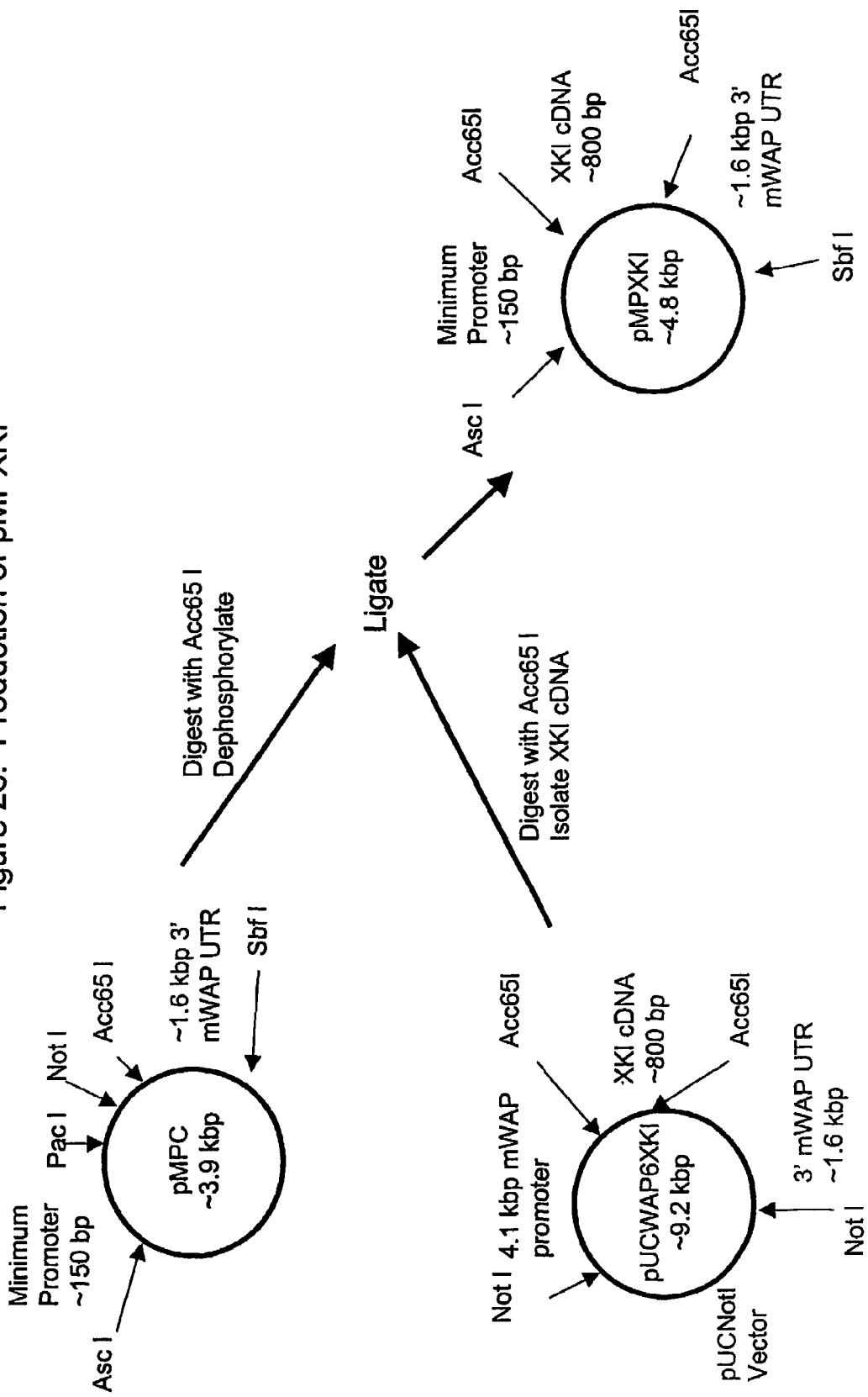
Figure 23. Production of pMPXKI

TRANSGENIC PROTEINS FROM MULTI-GENE SYSTEMS, METHODS, COMPOSITIONS, USES AND THE LIKE RELATING THERETO

RELATED APPLICATIONS

This application is a 35 U.S.C. 371 application of PCT/US02/072024 filed on Mar. 11, 2002, which claims benefit of U.S. Ser. No. 60/274,983 filed on Mar. 12, 2001. Both of these applications are incorporated in their entirety by reference for all purposes.

FIELD OF THE INVENTION

The invention provides, among other things, a system for producing transgenic proteins, compositions comprising transgenic proteins, transgenic organisms for making proteins, for modifying transgenic proteins in vivo. Illustrative embodiments of the invention particularly provide transgenic animals that express an exogenous gene for vitamin K-dependent proteins, protease inhibitors, blood clotting proteins and mammalian relaxins. In a highly particular illustrative embodiment in this regard the invention provides transgenic female pigs that express these same proteins in their milk in a temporally controlled manner during lactation using a multi-gene inducible system. In this regard, the invention relates particularly to female pigs having stably incorporated in their genomes non-endogenous DNA comprising a region that encodes these same proteins operably linked to a multi-gene system containing at least two different promoters in separate DNA constructs, where one of these promoters is a non-mammary gland specific promoter. Further in this regard the invention relates to the milk containing these same proteins and corresponding compositions derived from the milk. And it also relates to, among other things, uses of these proteins in wellness and therapeutic applications.

BACKGROUND

The concept of producing important pharmaceutical and nutriceutical proteins in transgenic animals is now firmly established (Van Cott, K. E. and Velander, W. H., Exp. Opin. Invest. Drugs, 7 (10): 1683-1690 (1998)), with three potential products, alpha-1 antitrypsin, antithrombin III and alpha glucosidase in the late stages of clinical trials. These proteins, and nearly all other transgenic polypeptides being developed commercially, were produced from a single DNA construct designed to produce a single polypeptide. In general terms, this "classical" design incorporates three distinct regions of DNA, which are all joined or operably linked in one contiguous strand.

The first region of DNA is a tissue specific promoter, in the above mentioned examples a milk protein promoter, which directs expression of the gene to a target organ, the mammary gland, which is regulated by lactogenic hormones, growth factors, cell-cell and cell-substratum interactions. The second region of DNA is the coding region, which may consist of complimentary DNA (cDNA, containing no introns), genomic DNA (gDNA) or a combination of both in a format called a mini-gene. It is important to note that cDNAs, and perhaps also minigenes, have a silencing effect (failure to express or poor expression levels) on adjacent transgenes (Clark, A. J., et al., NAR, 25 (5), 1009-1014, 1997). Therefore, a method of overcoming this silencing effect using non-genomic DNA sequences is highly desirable. The coding region contains the information needed to produce a specific protein, including any processing and secretory signals. The third region, the 3' region, contains further regulatory sequences and may influence the quantity of polypeptide that is produced from that construct. Non-genomic DNA sequences are inherently smaller than gDNA sequences and are therefore, much easier to manipulate in classical transgene formats.

Although this classical design has been successful in producing commercially viable quantities of certain proteins, there are two areas in which this system is not optimal. First, it is generally accepted that using cDNAs or minigenes in a classically designed construct, is less efficient for protein production than using a corresponding gDNA coding region. Indeed, this is such a problem that methods have been developed to address this issue (Clark, A. J. et al, Biotechnology 10, 1450-1454, 1992). Whilst these methods can improve the efficiency and level of expression of cDNAs and minigenes to some extent, they do not improve expression to the same level as is typically obtained using gDNA. A higher level would be ideal for commercial protein production.

The second area in which the classical single gene DNA construct design is suboptimal is in the production of highly biologically active proteins in transgenic animals. Proteins with an extremely high biological activity can be detrimental to the transgenic animal, even if circulatory levels (or other systemic levels) are low (Castro, F. O., et al., Selection of Genes for Expression in Milk: The Case of the Human EPO Gene, in Mammary Gland Transgenesis. Therapeutic Protein Production. Castro and Janne (eds.) Springer-Verlag Berlin New York, 91-106, 1998). This can be due in large part to either ectopic expression (expression of the transgene in organs other than the targeted one) or leakage of the protein product into the blood from the target organ. If the protein product is highly biologically active, expression ideally must be strictly controlled so that the animal is exposed to the product for a short time only, thus reducing the chance of any lasting detrimental effects. This requires an expression system that can be turned on and off very rapidly and precisely.

Regulation of Promoters

The expression of many genes is controlled at the level of transcription, when the DNA sequences are transcribed into RNA, prior to being translated into protein (Latchman, D. S., Eukaryotic Transcription Factors, Academic Press, 1998). The DNA sequence element that controls transcription is the promoter. This generally contains a small core region, which is capable of directing constitutive or basal levels of transcription, and upstream response elements that control spatial and temporal regulation of transcription. These DNA sequences include two types of elements, those which are involved in the basic process of transcription and are found in many genes exhibiting distinct patterns of regulation, and those found only in genes transcribed in a particular tissue or in response to a specific signal. The latter elements likely produce this specific expression pattern. They are binding sites for a wide range of different cellular proteins (transcription factors) whose levels fluctuate in response to stimuli from external or internal sources. Gene expression in a given tissue may be stimulated or inhibited depending on the type and amount of transcription factors that are present in that tissue at any time. Many transcription factors or other proteins that enable transcription factor pathways are largely uncharacterized from the perspective of an exact biochemical analysis, which details their conformationally-dependent interactions with DNA. Overall, the regulation of expression at the DNA level, is a function of which regulatory elements (binding sites) are present in the promoter and how the cell or tissue responds to its environment by changing the relative levels of the different DNA binding transcription factors in the cell.

Another mechanism involved in the precise control of gene expression is transcriptional repression (Maldonado, E., et al, Cell, 99 (5), 455458, 1999). Transcriptional repressor proteins associate with their target genes either directly through a DNA-binding domain or indirectly by interacting with other DNA-bound proteins. The repressor protein can inhibit transcription by masking a transcriptional activation domain, blocking the interaction of an activator with other transcription components or by displacing an activator from the DNA.

Milk protein genes are characterized by a strict tissue specific expression and regulation during the process of functional differentiation. They are coordinately expressed in response to various developmental signals, such as changing levels of lactogenic hormones prolactin, insulin, glucocorticoids, progesterone), local levels of certain growth factors (EGF), cell-cell interactions and interactions with extra-cellular matrix (ECM) components (Rijnkels, M. and Pieper, F. R., Casein Gene-Based Mammary Gland-Specific Transgene Expression, in Mammary Gland Transgenesis. Therapeutic Protein Production. Castro and Janne (eds.) Springer-Verlag, Berlin, New York, 41-64, 1998).

Lactogenic hormones activate latent transcription factors in the cytoplasm of mammary epithelial cells. The steroid hormones progesterone, estrogen, and glucocorticoid regulate the transcription of target genes by binding to specific intracellular receptors. Some models purport that binding of the hormone with its receptor changes the receptor's conformation from a physiologically inactive form to a form which is active and capable of dimerization. The active receptors are then capable of binding specific DNA sites in the regulatory region of the target gene promoters, stimulating gene transcription and thus, protein synthesis. Steroid receptors belong to a superfamily of ligand-inducible transcription factors and it has been well documented that these are modular proteins organized into structurally and functionally defined domains. It has also been shown that these domains can be rearranged as independent cassettes within their own molecules or as hybrid molecules with domains from other regulatory peptides. Interestingly, the transactivation domains of the glucocorticoid receptor can be duplicated in tandem and show positional independence in a "super receptor" with 3-4 times the activity of the wild type protein. (Hollenberg, S. M. and Evans, R. M., Cell, 55, 899-906, 1988; Fuller, P. J., FASEB J., 5, 3092-3099, 1991; U.S. Pat. No. 5,364,791; U.S. Pat. No. 5,935,934; Whitfield, G. K., et al, J. Cell. Biochem., suppl. 32-33, 110-122, 1999; Braselmann, S., et al, PNAS, 90, 1657-1666, 1993). The structure and function of the steroid receptor superfamily is well conserved. Generally there are three main domains and several sub-domains or regions. The NH2-terminal domain is the least conserved in size and sequence and contains one of the two, transactivation sequences of the receptor. The central DNA binding domain of about 70 amino acids is highly conserved, as is the COOH-terminal ligand binding domain. This latter domain also contains sub-domains responsible for dimerization, heat shock protein (hsp) 90 binding, nuclear localization and transactivation.

Prolactin plays the essential role in milk protein gene expression and exerts its effect through binding to the extracellular domain of the prolactin receptor and through receptor dimerization. This activates a protein tyrosine kinase (JAK2) which is non-covalently associated with the cytoplasmic domain of the prolactin receptor (Gouilleux, F., et al, EMBO J., 13 (18), 4361-4369, 1994; Imada, K and Leonard, W. J., Mol. Immunol., 37 (1-2), 1-11, 2000). The activated JAK2 phosphorylates the signal transducer and transcription activator, Stat 5, causing it to dimerize and subsequently, translocate to the nucleus. Once in the nucleus, Stat5 specifically binds to sequence elements in the promoter regions of milk protein genes (Liu, X., et al, PNAS, 92, 8831-8835, 1995; Cella, N., et al, Mol. Cell. Biol., 18 (4), 1783-1792, 1998; Mayr, S., et al, Eur. J. Biochem., 258 (2), 784-793, 1998). In an analysis of 28 milk protein gene promoters (Malewski, T., BioSystems, 45, 29-44, 1998) there were 4 transcription factor binding sites that were present in every promoter, C/EBP, CTF/NF1, MAF and MGF (Stat 5). Although steroid hormone receptors and Stat factors comprise two distinct families of inducible transcription factors their basic structure is similar. Stat proteins are modular with an amino terminus that regulates nuclear translocation and mediates the interaction between Stat dimers (Callus, B. A. and Mathey-Prevot, B., J. Biol. Chem., 275 (22), 16954-16962, 2000). There is a central DNA binding domain and a carboxy terminal region, which contains the phosphorylation site and a transactivation domain.

Egg white genes seem to be regulated in a similarly complex manner. It is known that the progesterone-dependent activation of the egg white genes in the chicken oviduct is mediated through the progesterone receptor (Dobson, A. D. W., et al, J. Biol. Chem., 264 (7), 4207-4211, 1989). In addition, the chicken ovalbumin upstream promoter-transcription factor (COUP-TF) is a high affinity and specific DNA binding protein, which interacts as a dimer with the distal promoter sequence of the ovalbumin gene and promotes initiation of transcription of this gene by RNA polymerase (O'Malley, B. W. and Tsai, M-J., Biol. Reprod., 46, 163-167, 1992). COUP-TFs are orphan members (no binding ligand has as yet been determined for these receptors) of the nuclear receptor superfamily, and have been shown to play a key role in the regulation of organogenesis, neurogenesis, metabolic enzyme production and cellular differentiation during embryogenic development, via transcriptional repression and activation (Sugiyama, T., et al, J. Biol. Chem., 5 (5), 3446-3454, 2000).

A protein expression method based on the inducible Tet repressor system has been developed (Furth, P. A., et al, PNAS, 91, 9302-9306, 1994), but the levels of basal expression without induction are too high to be useful in transgenic animals (Soulier S. et al, Eur. J. Biochem. 260, 533-539, 1999). Another inducible system based on the use of the ecdysone receptor has been reported (No, D., et al, PNAS, 93, 3346-3351, 1996; PCT 97/38117, PCT 99158155) and has recently given encouraging results in transgenic mice (Albanese, C., et al, FASEB J., 14, 877-884, 2000). However, this system required the delivery of an exogenous ligand to the mice for the full lactation period. Such a ligand would be costly and difficult to procure for regular administration in a production environment.

A new multi-gene system for protein production in transgenic animals would improve commercial levels of production from cDNA constructs by amplifying specifically tailored transcription factors which need not naturally occur in the tissue targeted for expression, but would be transgenically expressed specifically in that tissue. Unlike classical gene expression formats for recombinant proteins, the tissue specific promoter would not be linked to the protein to be expressed, but would be used to drive expression of transcription factors which do not have a signal sequence and so are not secreted. In addition, the added control that a doubly inducible multi-gene system would provide, which is inexpensive and easily applied, could enable the production of highly biologically active proteins in transgenic animals in a pulsatile fashion so as to avoid longterm detrimental effects.

Proteins for Transgenic Production

A multi-gene system, as described below, can be used to direct expression of any protein, particularly any secreted protein, which can be expressed in a transgenic organism in useful quantities, either for research or commercial development. Particular proteins of interest with respect to production by multi-gene expression systems include relaxin and other hormones with cross-species activity such as growth factors, erythropoietin (EPO) and other blood cell growth stimulating factors. For these proteins, the expression may be problematic in terms of harming the host animal as is known to happen when EPO is expressed for an extended period of time. It is noted that tissue specific expression of transgenes is not an absolute phenomenon and promiscuous expression or systemic transport of the expressed recombinant protein within the animal almost always occurs with any expression system in any animal, albeit at very low levels. However, even at low levels of expression of EPO, when the EPO is expressed over an extended period of time, the hematocrit of the host animal can rise to a fatal level. Thus a temporal control which can enable pulse expression using an external inducer molecule could overcome the problems of continuous and extended expression (ie., as could occur if expression occurs over an entire lactation period). Pulse or truncated expression would be useful in preventing an adverse, systemic physiologic effect by recombinant molecules like EPO, which can cause these effects at very low levels.

Relaxin is widely known as a hormone of pregnancy and parturition and typically circulates at less than 50 pg/ml in the blood of women. However, it is now emerging that the peptide has a far wider biological function than was at first thought. There are receptor sites for relaxin in striated muscle, smooth muscle, cardiac muscle, connective tissue, the autonomic and the central nervous systems. Human relaxin has been demonstrated to inhibit excessive connective tissue build-up and is in Phase II trials for the treatment of Scleroderma Porcine relaxin was available commercially in the 1950-60s and was used extensively for such conditions as cervical ripening, scleroderma, premature labour, PMS, decubital ulcers and glaucoma. Relaxin is known to adversely affect the lactation of different mammalian species but does not seem to affect the pig in a similar manner. Therefore, the pig is perfectly suited for production of relaxin in milk.

Other examples of proteins which it would be desirable to produce in transgenic organisms, are proteins that are protease inhibitors. Some examples of protease inhibitors are Alpha 1-antitrypsin, Alpha 2 Macroglobulin, and serum leukocyte protease inhibitor. These proteins are serine protease inhibitors that show antiviral, non-steroidal anti-inflammatory and wound healing properties. These proteins are useful in veterinary, cosmetic and nutriceutical applications.

Alpha 1-antitrypsin (AAT) is a naturally occurring glycoprotein produced by the liver. Improperly glycosylated recombinant AAT such as made by yeast, does not have a sufficient circulation half-life to be used as a parenterally administered therapeutic. Congenital deficiency results in the condition emphysema and in 1985 Bayer Pharmaceuticals began marketing a plasma derived AAT product, Prolastin. Unfortunately, due to shortages of Asafe@ plasma and frequent recalls, supplies of Prolastin are often very limited. AAT has also been used to treat psoriasis, atopic dermatitis, ear inflammation, cystic fibrosis and emphysema, and to assist in wound healing. It has been estimated that over 10 million people in the US alone may benefit from AAT therapies.

Alpha 2 macroglobulin (A2M) is a very large, complex glycoprotein with a published cDNA sequence containing 1451 amino acids. The mature protein is a tetrameric molecule composed of four 180 kDa subunits and thus has a molecular weight which is over 720 kDa. Its complexity makes it most suited for production in mammalian systems but few mammalian systems will likely make A2M at commercially viable levels. A2M is indicated for treatment of asthma, bronchial inflammation and eczema and acts as a protease inhibitor to both endogenous and exogenous proteases that cause inflammation. A2M is necessarily more potent than alpha 1-antitrypsin due to its irreversible binding of target proteases. A2M is also useful in inhibiting proteases frequently found in (thermal) burn wounds from yeast and other infections. The high specific activity of these types of proteases allows for smaller doses during treatment. Thus, A2M=s complexity and specific activity make it ideally suited for production in transgenic pig mammary glands.

Vitamin K-Dependent Proteins

Vitamin K-dependent (VKD) proteins such as those proteins associated with haemostasis have complex functions which are largely directed by their primary amino acid structure. In particular, the post-translational modification of glutamic acids in the amino terminal portion of these molecules is essential for proper biological activity. This includes biological activity of both pro-coagulation and anti-coagulation. This particular domain found in VKD-proteins is called the "gla domain". For example, the Gla domain is an essential recognition sequence in tissue factor (TF) mediated pro-coagulation pathways. The anti-coagulation of this pathway depends upon the lipoprotein-associated coagulation inhibitor, termed LACI, which is a non-VKD protein. LACI forms a complex with the Gla domain of factor Xa, factor VIIa, and TF. Specifically, the Gla domain of factor Xa (FXa) is needed for this procoagulation inhibitory activity. It has been shown that recombinant chimeric molecules having LACI inhibitor (Kunitz type) regions and the Gla domain of FXa can be inhibitory of the TF pathway.

TABLE 1

| VKD proteins. | | |
|---|---|---|
| Protein C | Factor X (FX) | Bone Gla protein (Osteocalcin) |
| Protein S | Prothrombin | |
| Protein Z | Factor VII | |
| Factor IX | | |

Gamma-carboxylation is required for calcium-dependent membrane binding. All of the proteins listed in Table 1 have multiple Gla-residues in a concentrated domain. The Gla-domains of these proteins mediate interaction and the formation of multi-protein coagulation protein complexes. Mammalian coagulation (here collectively meaning both pro-coagulation and anti-coagulation pathways and mechanisms) physiology requires that nearly complete-carboxylation of VKD-proteins occurs within the respective Gla domain for each of these proteins to be maximally functional. Notably, in the context of recombinant synthesis of any protein containing Gla-domains, the extent of gamma-carboxylation of VKD-proteins varies from one mammalian cell source to another, including differences between species and tissue within a species.

VKD-proteins of interest with respect to production by single or multi gene expression systems include those in Table 1, particularly blood clotting factor IX, Protein C and chimeric hybrid vitamin K-dependent proteins. Factor IX is an essential blood clotting protein. Haemophilia B is a genetic disorder in which the production of active Factor IX is defective. It is an inherited disorder that primarily affects males, at the rate of approximately 1 in 30,000. The consequent inability to produce sufficient active Factor IX can lead to profuse bleeding, both internally and externally, either spontaneously or from relatively minor injuries.

In spite of techniques available to amplify recombinant synthesis of VKD proteins such as Protein C and Factor IX, biologically functional recombinant versions of these proteins are difficult to produce and are made typically at levels less than about 0.1 grams per liter per 24 hours in recombinant cell culture media (Grinnell, B. W., et al, in Protein C and Related Anticoagulants. Bruley, D. F. and Drohan, W. N. (eds.), Houston, Tex.; Gulf Publishing Company, 29-63, 1990), or less than 0.22 gm per liter per hour in the milk of transgenic livestock (Van Cott, K. E., et al., Genetic Analysis: Biomolecular Eng., 15, 155-160, 1999). The expression of high levels of FIX using a cDNA construct is difficult. However, the gDNA of FIX, at 33 kbp, is rather large and difficult to manipulate, particularly when compared to the FIX cDNA, which is only 1.4 kbp.

Most VKD-blood plasma proteins are also glycosylated. The extent and types of glycosylation observed is heterogeneous and varies considerably in all species and cell types within a species. Examples of the heterogeneity, structure function relationships of glycosylation are cited by Degen, Seminars in Thrombosis and Hemostasis, 18 (2), 230-242, 1992; Prothrombin and Other Vitamin K Proteins, Vols I and II, Seegers and Walz, Eds., CRC Press, Boca Raton, Fla., 1986.

Glycosylation is a complex post translational modification that occurs on many therapeutic proteins. The process of glycosylation attaches polymeric sugar compounds to the backbone of a protein. These sugar-based structures impart not only an immunologically specific signature upon the protein, but also can change the specific level of activity that the protein has with relation to how long it can reside in the bloodstream of a patient, or how active the protein is in its basic function. All three of these facets can make or break the protein in its role as a therapeutic or wellness product. For example, genetically engineered yeast can impart glycosylation that results in an immunologically adverse signature, which can stimulate the body to make antibodies and essentially reject the protein. In fact, that is part of the reason why yeast vaccines are effective; they easily induce an immune response. The mammary gland of ruminants produces a substantial fraction of glycosylation on milk proteins, which resemble the primitive sugars found in yeast. Thus, applications that result in the long term, repeated exposure of proteins containing yeast or yeast-like signatures, to human tissue are intensely scrutinized with respect to the potential of adverse immune reactions. This structure is also apt to cause dysfunction with respect to the protein=s natural activity and may also contribute to a shortened residence time in blood. In contrast, the mammary gland of pigs gives a glycosylation signature that more closely resembles that found in normal human blood proteins, helping to assure biochemical function and a long circulatory half-life.

The complex post-translational modifications of therapeutic proteins, such as those discussed above that are necessary for physiological activities, pose a difficult obstacle to the production of active vitamin K dependent proteins in cells using cloned genes. Moreover, attempts to culture genetically altered cells to produce VKD polypeptides have produced uneconomically low yields and, generally, preparations of low specific activity. Apparently, the post-translational modification systems in the host cells could not keep pace with production of exogenously encoded protein, reducing specific activity. Therefore, cell culture production methods have not provided the hoped for advantages for producing highly complex proteins reliably and economically.

An attractive alternative is to produce these complex proteins in transgenic organisms. However, it is likely that only mammals and perhaps birds will be able to carry out all the post-translational modifications necessary for their physiological function. It has not been possible, as yet, to produce commercially viable levels of certain complex polypeptides from a controlled source in a highly active form with a good yield, and there exists a need for better methods to produce such proteins.

An interesting new class of proteins, which is likely to be difficult to produce in commercial quantities in cell culture, is the genetically engineered fusion, chimeric and hybrid molecules that are now being developed. These proteins are designed and produced by combining various domains or regions from different natural proteins, either wild type or mutated, which can confer the properties of each domain or region to the final hybrid molecule. An example of this is $X_{LC}LACI_{K1}$ (Girard, T. J., et al., Science 248, 1421-1424, 1990) which is a hybrid protein made up of domains from factor X and lipoprotein-associated coagulation inhibitor (LACI). LACI appears to inhibit tissue factor (TF)-induced blood coagulation by forming a quaternary inhibitory complex containing FXa, LACI, FVIIa and TF. $X_{LC}LACI_{K1}$ directly inhibits the activity of the factor VIIa-TF (tissue factor) catalytic complex, but is not dependent on FXa Gamma-carboxylation of the FX portion of the hybrid protein is required for inhibitory activity. In order for efficient carboxylation to occur at high levels, it is likely that the propeptide of the recombinant VKD-protein must be properly matched to the endogenous carboxylase system (Stanley, T. B., et al, J. Biol. Chem., 274 (24), 16940-16944, 1999). This is probably true for all VKD-polypeptides including chimeric ones such as $X_{LC}LACI_{K1}$. It appears that the endogenous carboxylase systems of any given species or tissue within that species, most of which are not identified or characterized, will differ in their compatibility to any given pro-peptide sequence. Also it is frequently desirable to have the propeptide cleaved from the nascent VKD protein, such as a $X_{LC}LACI_{K1}$ polypeptide, once gamma-carboxylation has been completed on the polypeptide's gla domain. It is therefore, also important to find a propeptide sequence that will be efficiently cleaved within the specific species and tissue in which it is being recombinantly produced. These factors render it problematic to find an expression system, which can produce desirable amounts of biologically active VKD-proteins such as $X_{LC}LACI_{K1}$ chimeric proteins. In spite of being known as a potent coagulation inhibitor since the early 1990s, $X_{LC}LACI_{K1}$ chimeric molecules have not been made in large amounts in a commercially viable manner (ie., greater than 0.1 gm per liter per 24 hours) in recombinant mammalian cell culture. One way to improve expression of this protein in a transgenic system, particularly in transgenic pigs, may be to substitute the FIX propeptide sequence for the FX propeptide sequence, such a protein would be termed 9XKI.

New therapeutic molecules are being designed to have increased activity, decreased inactivation, increased half-life or specific activity and reduced immunogenicity and/or immunoreactivity to existing circulating antibodies in patients' bloodstreams. This has been demonstrated in genetically engineered Factor VIII proteins (U.S. Pat. No. 5,364, 771, U.S. Pat. No. 5,583,209, U.S. Pat. No. 5,888,974, U.S. Pat. No. 5,004,803, U.S. Pat. No. 5,422,260, U.S. Pat. No. 5,451,521, U.S. Pat. No. 5,563,045). Mutations include deletion of the B domain (Lind, P., et al., Eur. J. Biochem. 232, 19-27, 1995), domain substitution or deletion, covalent linkage of domains, site-specific replacement of amino acids and mutation of certain cleavage sites. In particular, a genetically engineered inactivation-resistant factor VIII (IR8) has been developed to help in the treatment of hemophilia A (Pipe, S. W. and Kaufman, R. J., PNAS 94, 11851-11856, 1997). The introduction of specific sequences from porcine factor VIII can also be useful in the formation of a recombinant FVIII which is used to treat hemophiliacs with improved properties as stated above. These molecules can also be designed for improved expression. It is widely known that FVIII has restrictions in intracellular trafficking which lead to low levels of secretion. Modification of the domains associated with intracellular interactions with immunoglobulin binding protein (Bip) or calnexin would be examples of modifications used to improve secretory processing efficiency (Kaufman, R. J., Abstract S1-8, $10^{th}$ Int. Biotech. Symp., Sydney, Australia, 25-$30^{th}$ Aug., 1996). Factor VIII gDNA is another example of an extremely large and unwieldy DNA sequence (~110 kbp), whereas the cDNA is only 7 kbp, making it much more manageable.

Whey acidic protein (referred to as "WAP") is a major whey protein in the milk of mice, rats, rabbits and camels. The regulatory elements of the mouse WAP gene are entered in GenBank (U38816) and cloned WAP gene DNAs are available from the ATCC. The WAP promoter has been used successfully to direct the expression of many different heterologous proteins in transgenic animals for a number a years (EP0264166, Bayna, E. M. and Rosen, J. M., NAR, 18 (10), 2977-2985, 1990). Lubon et al (U.S. Pat. No. 5,831,141) have used a long mouse WAP promoter (up to 4.2 kbp) to produce Protein C in transgenic animals. However, the longest rat WAP promoter that has been used is 949 bp (Dale, T. C., et al., Mol. Cell. Biol., 12 (3), 905-914, 1992).

SUMMARY

The present invention is directed to producing transgenic proteins, compositions comprising transgenic proteins, transgenic organisms for making proteins, for modifying transgenic proteins in vivo, and to addressing the previously-discussed issues, e.g., as characterized in connection with the above-cited references each of which is incorporated by reference generally and more specifically as such teachings relate to methodology for related transgenic protein production and applications of such proteins.

In one embodiment of the present invention there is provided a multi-gene system for regulating the expression of a protein in a transgenic non-human mammal.

In another embodiment of the present invention there is provided one or more plasmids containing multi-gene system DNA sequences.

In yet another embodiment of the present invention, there is provided a process for the production of one or more polypeptides, comprising the steps of (1) providing a transgenic non-human mammal characterized by multiple exogenous DNA sequences stably integrated in its genome, wherein the exogenous DNA sequences comprise a multi-gene system, being effective in directing the secretion of the polypeptide(s) into the milk of said transgenic non-human mammal, (2) producing the milk from the transgenic non-human mammal; (3) collecting the milk and purifying the polypeptide(s) from the milk. In one preferred embodiment, the transgenic non-human mammal is a mouse, rat, rabbit, pig, sheep, cow or goat. In an especially preferred embodiment the transgenic non-human mammal is a pig.

In yet another embodiment of the present invention there are provided transgenic non-human transgenic mammals containing the multi-gene system sequences directing the expression of a protein product(s).

And in still yet other embodiments of the present invention there is the production of a functional genetically engineered fusion, chimeric or hybrid protein molecule in a transgenic non-human mammal.

And in still yet other embodiments of the present invention there are multi-gene system sequences encoding gamma-carboxylated polypeptides as the desired products, so as to engender production of the gamma-carboxylated proteins.

And in still yet other embodiments of the present invention there are the multi-gene system sequences encoding a genetically engineered gamma-carboxylated polypeptide so as to engender production of the genetically engineered gamma-carboxylated protein.

And in still yet other embodiments of the present invention there is the production of a genetically engineered gamma-carboxylated protein, in a transgenic non-human mammal.

And in still yet other embodiments of the present invention there are single-gene and multi-gene system sequences encoding a genetically engineered Protein C so as to engender more efficient production of the Protein C protein.

And in still yet other embodiments of the present invention there is a transgenic non-human mammal as above where the introduced genetic construct comprises the single-gene and multi-gene system sequences encoding Protein C, so as to engender more efficient production of the Protein C protein.

And in still yet other embodiments of the present invention there is the production of a functional mutated fusion gamma-carboxylated protein, such as $X_{LC}LACI_{K1}$ (also known as XKI), in a transgenic non-human mammal.

And in still yet other embodiments of the present invention there is the production of a functional mutated fusion gamma-carboxylated protein, such as 9XKI, in a transgenic non-human mammal.

And in still yet other embodiments of the present invention there is a composition comprising $X_{LC}LACI_{K1}$ produced in a transgenic non-human mammal as above described.

And in still yet other embodiments of the present invention there is a composition for treating coagulopathy associated with sepsis comprising a genetically engineered fusion protein, such as $X_{LC}LACI_{K1}$ or 9XKI, derived from the milk of a transgenic non-human mammal as described above.

And in still yet other embodiments of the present invention there is a composition for treating various diseases or conditions that require an anticoagulant protein comprising Protein C derived from the milk of a transgenic non-human mammal as described above.

And in still yet other embodiments of the present invention there is a composition for treating various diseases or conditions that require an anticoagulant protein comprising a genetically engineered fusion protein, such as XKI or 9XKI, derived from the milk of a transgenic non-human mammal as described above.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention may be more completely understood in consideration of the detailed description of various embodiments of the invention in connection with the accompanying drawings, in which:

FIG. 1 is assembly of the plasmid pXKI, according to an example embodiment of the present invention;

FIG. 2. assembly of the plasmid pUCWAP6XKI, according to another example embodiment of the present invention;

FIG. 3 is assembly of the plasmid p9XKI; according to yet another example embodiment of the present invention;

FIG. 4 is assembly of the plasmid pUCWAP69XKI; according to yet another example embodiment of the present invention;

FIG. 5. is assembly of plasmid p9Pcpartial; according to yet another example embodiment of the present invention;

FIG. 6 is production of the plasmid pUCWAP5-9-PC; according to yet another example embodiment of the present invention;

FIG. 7 is production of plasmid p10Pcpartial; according to yet another example embodiment of the present invention;

FIG. 8 is assembly of plasmid pUCWAP5-10-PC; according to yet another example embodiment of the present invention;

FIG. 9 is production of plasmid p7Pcpartial; according to yet another example embodiment of the present invention;

FIG. 10 is assembly of plasmid pUCWAP5-7-PC; according to yet another example embodiment of the present invention;

FIG. 11 is production of plasmid pUC8-3'UTR; according to yet another example embodiment of the present invention;

FIG. 12 is a diagram of plasmid pCR4Gal-4; according to yet another example embodiment of the present invention;

FIG. 13 is production of plasmid pStat(-DBD); according to yet another example embodiment of the present invention;

FIG. 14 is production of plasmid pStatdeltaDBD; according to yet another example embodiment of the present invention;

FIG. 15 is production of plasmid pMCS-Stat; according to yet another example embodiment of the present invention;

FIG. 16 is assembly of plasmid pLMWStat; according to yet another example embodiment of the present invention;

FIG. 17 is assembly of plasmid pSMWStat; according to yet another example embodiment of the present invention;

FIG. 18 is production of the plasmid pGem(Eco-)GR; according to yet another example embodiment of the present invention;

FIG. 19 is production of the plasmid pGRdeltaDBD; according to yet another example embodiment of the present invention;

FIG. 20 is production of the plasmid pGRdeltaD2; according to yet another example embodiment of the present invention;

FIG. 21 is assembly of plasmid pUCWAP6GR; according to yet another example embodiment of the present invention;

FIG. 22 is assembly of the minimum promoter cassette vector pMPC; according to yet another example embodiment of the present invention;

FIG. 23 is assembly of plasmid pMPXKI; according to yet another example embodiment of the present invention;

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention as defined by the appended claims.

DETAILED DESCRIPTION

The present invention also provides amongst other things, methods for regulating the expression of a protein in a transgenic organism, methods for obtaining polypeptides from transgenic organisms, compositions comprising transgenically produced polypeptides, and uses thereof, as described in greater detail below.

Methods for Making Transgenic Organisms

Transgenic organisms may be produced in accordance with the invention as described herein using a wide variety of well-known techniques, such as those described in Perry, M. M. and Sang, H. M., Transgenic Res. 2, 125-133; Ho Hong, Y. et al., Transgenic Res. 7 (4), 247-252, 1998; Genetic Engineering Of Animals, Ed. A. Puhler, VCH Publishers, New York (1993) and in more detail in Volume 18 in Methods in Molecular Biology: Transgenesis Techniques, Eds. D. Murphy and D. A. Carter, Humana Press, Totowa, N. J. (1993); all of which are incorporated herein by reference in their entireties, particularly as to the foregoing in parts pertinent to methods for making transgenic organisms that express polypeptides. See also for instance Lubon et al., Transfusion Medicine Reviews X(2): 131-141 (1996) and Pursel, V. G., et al., 480 in the proceedings of $11^{th}$ International Congress on Animal Reproduction and Artificial Insemination, Dublin, Ireland, 1988, which are incorporated herein by reference in their entirety, particularly as to the foregoing in parts pertinent to methods for making transgenic organisms.

In particular, transgenic mammals, such as mice and pigs, that express polypeptides in accordance with certain preferred embodiments of the invention, can be produced using methods described in among others Manipulating The Mouse Embryo, Hogan et al., Cold Spring Harbor Press (1986); Krimpenfort et al., Bio/Technology 9: 844 et seq. (1991); Palmiter et al., Cell 42: 343 et seq. (1985); Genetic Manipulation of the Early Mammalian Embryo, Kraemer et al., Cold Spring Harbor Press, Cold Spring Harbor, N.Y. (1985); Hammer et al., Nature 315: 680 et seq. (1985); U.S. Pat. No. 4,873,191 of Wagner et al for Genetic Transformation of Zygotes, and U.S. Pat. No. 5,175,384 of Krimpenfort et al. for Transgenic Mice Depleted in Mature T-Cells and Methods for Making Transgenic Mice, each of which is incorporated herein by reference in its entirety, particularly as to the foregoing in parts pertinent to producing transgenic mammals by introducing DNA or DNA:RNA constructs for polypeptide expression into cells or embryos For example, transgenic organisms of the present invention can be produced by introducing into eggs, or developing embryos, one or more genetic constructs that engender expression of polypeptides as described herein. In certain preferred embodiments of the invention, DNAs that comprise cis-acting transcription controls for expressing a polypeptide operably linked to a region encoding the polypeptide are highly preferred. In other preferred embodiments a multi-gene system directing expression of a polypeptide and containing the DNA sequences coding for such a polypeptide, are highly preferred. Also highly preferred in this regard are single and or multi-gene constructs as described herein, that engender expression of genetically engineered genes for polypeptides. Constructs that comprise operable signal sequences that effectuate transport of the polypeptide product into a targeted compartment of an organism, such as a tissue or fluid, are further preferred in certain embodiments in this regard. Also especially preferred in this regard are constructs that are stably incorporated in the genome of germ line cells of the mature organism and inherited in normal, Mendelian fashion upon reproduction. One or more DNA or RNA:DNA hybrids or the like may be used alone or together to make transgenic organisms useful in the invention as described further below.

Standard, as well as unusual and new techniques for making transgenic organisms generally can be used to make transgenic organisms in accordance with the invention. Useful techniques in this regard include, but are not limited to, those that introduce genetic constructs by injection, infection, transfection—such as calcium phosphate transfection, using cation reagents, using sperm or sperm heads or the like—lipofection, liposome fusion, electroporation, and ballistic bombardment. Useful techniques include both those that involve homologous recombination, which can be employed to achieve targeted integration, and those that do not, such as those disclosed below.

Constructs can be introduced using these and other methods into differentiated cells, such as fibroblast cells, which are capable of being reprogrammed and then cloned, pluripotent cells, totipotent cells, germ line cells, eggs, embryos at the one cell stage, and embryos at several cell stages, among others, to make transgenic organisms of the invention. In these regards, among others, they may be introduced by such methods into pronuclear, nuclear, cytoplasmic or other cell compartments or into extracellular compartments of multicellular systems to make transgenic organisms of the invention.

In a preferred method, developing embryos can be infected with retroviral vectors and transgenic animals can be formed from the infected embryos. In a particularly preferred method DNAs in accordance with the invention are injected into embryos, at the single-cell or several cell stage. In some particularly preferred embodiments in this regard, DNA is injected into the pronucleus of a one-cell embryo. In other preferred embodiments in this regard, DNA is injected into the cytoplasm of a one-cell embryo. In yet another particularly preferred embodiment in this regard, DNA is injected into an early stage embryo containing several cells.

Certain aspects of the invention relate to the introduction into organisms of genetic constructs that engender expression of a polypeptide. Among those that are useful in some aspects of the invention in this regard are polynucleotide constructs that provide a DNA sequence encoding a polypeptide of the invention operably linked to cis-acting signals necessary for expression in a transgenic organism and, in certain preferred embodiments, for transport of a translation product encoded by the construct into a particular compartment of the organism. Among particularly preferred embodiments in this regard are DNA polynucleotides.

The constructs may comprise a multi-gene system as described below, or be a single polynucleotide or several polynucleotides in the classical single gene system, when introduced into a cell or embryo or the like to form a transgenic organism in accordance with the invention. Particularly preferred are single chain, double-stranded DNA polynucleotides in this regard. Also preferred are DNA-RNA hybrid polynucleotides. When more than one polynucleotide is used in this regard, they generally combine with one another and or with endogenous genetic elements of the host organism, as a result of in vitro or in vivo processes, to form a construct that then engenders transgenic expression of the polypeptide in the host organism.

Double Inducible—Multi-Gene System 1

In multi-gene system 1, when the type A gene construct promoter is switched on by the appropriate transcription factors in the targeted tissue, the protein it produces is an inducible transactivation factor. This needs to be activated by suitable endogenous factors before it can bind to the minimal promoter(s) of the type B gene construct(s), and initiate expression of the type B construct(s), resulting in production of the final polypeptide product(s).

Type A Gene Construct:

The first, type A gene construct has a tissue-specific promoter to direct expression to the tissue of choice, and this drives the production of a mutated, endogenously inducible transcription factor, which can be a mutated steroid hormone receptor or another mutated, inducible transcription factor. Suitable 3' sequences are included for efficient expression in the tissue of choice. The encoded protein from the type A gene construct will be expressed, but not secreted, and can bind to the promoter of the type B construct(s), transcriptionally activating the type B gene construct(s), and causing the expression and production of the final protein product(s). However, this will only occur in the desired tissue or cells when other relevant transcription factors and ligands are present to bind to the mutated inducible transcription factor. By having all of the genes of the multi-gene system controlled by the required presence of endogenous factors in the correct tissue, this should reduce the chance of ectopic expression of the product protein, while at the same time, increasing levels of correct expression.

The tissue-specific promoter gives spatial and temporal control over the expression of the mutated transcription factor. An appropriately sized tissue specific promoter, in terms of its length and capacity to direct expression, must be used to ensure optimum expression of the transactivation factor, and ultimately, the final protein product. Representative examples of such promoters (Lubon, H., et al., Transfusion Med. Rev., X(2), 131-143, 1996) include liver specific, muscle specific, nerve cell specific, blood cell specific, blood plasma specific, bone cell specific, skin cell specific, kidney specific, intestinal specific, urine specific, seminal fluid specific, connective tissue specific, and any of the milk protein gene promoters, such as whey acidic protein (WAP), lactoferrin, alpha lactalbumin, betalactoglobulin, alpha S1 casein, alpha S2 casein, kappa casein and beta casein. Examples of egg white protein promoters include ovalbumin, conalbumin and lysozyme.

The protein coding region of the type A gene construct can be a modified inducible transcription factor, which is capable of being activated by endogenous. Alternatively, a suitable construct can be produced, by combining all of the necessary modules from different sources. An appropriate DNA binding domain is included so as to ensure the modified transcription factor only binds to, and activates transcription of, the desired gene(s); in this case, the type B construct(s). Sometimes, more than one polypeptide is required to produce the final protein product, such as fibrinogen. In this case the modified inducible transcription factor from the type A gene construct can be used to activate transcription of several type B constructs, providing they all have the same DNA binding site. Examples of suitable DNA binding sites (DBS) include the Gal-4 DBS, other yeast DBS, a viral DBS, insect DBS, bacterial DBS and other non-mammalian DBS.

Examples of modified inducible transcription factors that are activated by an endogenous ligand include Stat5a, Stat5b, glucocorticoid receptor, estrogen receptors alpha and beta, progesterone receptor and chicken ovalbumin upstream promoter-transcription factor (COUP-TF). Examples of modified inducible transcription factors that are activated by an exogenous ligand include the progesterone receptor and ecdysone receptor.

The inducible transcription factor can be modified by replacing its own DNA binding site with one of those mentioned above, whilst otherwise leaving its structure unchanged. Alternatively, one domain of the transcription factor's own transactivation domains can be duplicated within the protein, or a transactivation domain from another source can be added. Examples of transactivation domains that can be used include VP-16, TAF-1, TAF-2, TAU-1, TAU-2 and NFκB-p65.

Type B Gene Construct(s):

The type B gene construct(s) has a modular structure comprising a DNA binding site attached to a minimal promoter capable of directing expression of the product protein(s). In one embodiment the minimal promoter of the type B gene construct(s) contains only the TATA box region and transcription initiation site. In a further embodiment the minimal promoter may also contain other upstream responsive elements, such as the CCAAT, or CACCC box regions. The latter may give higher levels of expression but could lead to some low levels of constitutive expression. By altering the number of responsive elements on the type B minimal promoter(s), multiple type B constructs can be expressed at different levels. Alternatively, when producing the transgenic organism, the volume ratio of construct DNAs can be adjusted to give different copy numbers of each type B gene. In this way, the expression levels of separate polypeptides in a product protein such as fibrinogen, which contains three polypeptides, can be controlled somewhat independently.

The coding sequence for any desired protein can be placed downstream of the minimal promoter. Suitable 3' sequences are included for efficient expression in the tissue of choice.

Single Inducible—Multi-Gene System 2

In the multi-gene system 2, when the type A gene construct promoter is induced to direct expression by the appropriate tissue factors, the protein it produces is a transactivation factor which, in this case, does not need to be activated by any other factors. Because it contains a DNA binding domain that targets sequences found in the type B minimal promoter, it binds to the minimal promoter and constitutively drives expression of the type B construct(s), resulting in production of the final polypeptide product(s).

Type A Gene Construct:

The type A gene construct has a tissue specific promoter to direct expression to the tissue of choice, and this drives the production of a mutated non-inducible transcription factor, which could be a mutated steroid hormone receptor or another mutated transcription factor. Suitable 3' sequences are included for efficient expression in the tissue of choice. The encoded protein from the type A gene construct will be expressed, but not secreted, and can bind to the promoter of the type B construct(s), transcriptionally activating the type B gene construct(s), and causing the expression and production of the final protein product(s). In this case, the protein expressed from the type A construct is a constitutive transactivator and is not inducible. If the type A construct is driven by a strong inducible promoter, then a considerable level of amplification can be achieved in production of the protein(s) from the type B gene construct(s).

The tissue specific promoter gives spatial and temporal control over the expression of the mutated transcription factor. Representative examples of such promoters (Lubon, H., et al., Transfusion Med. Rev., X(2), 131-143, 1996) include liver specific, muscle specific, nerve cell specific, blood cell specific, blood plasma specific, bone cell specific, skin cell specific, kidney specific, intestinal specific, urine specific, seminal fluid specific, connective tissue specific, and any of the milk protein gene promoters, such as whey acidic protein (WAP), lactoferrin, alpha lactalbumin, betalactoglobulin, alpha S1 casein, alpha S2 casein, kappa casein and beta casein. Examples of egg white protein promoters include ovalbumin, conalbumin and lysozyme.

The protein coding region of the type A gene construct can be a modified non-inducible transcription factor. Alternatively, a suitable construct can be produced, by combining all of the necessary modules from different sources. An appropriate DNA binding domain is included so as to ensure the modified transcription factor only binds to, and constitutively activates transcription of, the desired gene(s); in this case, the type B construct(s). Sometimes, more than one polypeptide is required to produce the final protein product, such as fibrinogen. In this case the modified non-inducible transcription factor from the type A gene construct can be used to constitutively activate transcription of several type B constructs, providing they all have the same DNA binding site. Examples of suitable DNA binding sites (DBS) include the Gal-4 DBS, other yeast DBS, a virus DBS, insect DBS, bacterial DBS and other non-mammalian DBS.

Examples of modified transcription factors that can be used include Stat5a, Stat5b, glucocorticoid receptor, estrogen receptors alpha and beta, progesterone receptor, chicken ovalbumin upstream promoter-transcription factor (COUP-TF), and the ecdysone receptor.

The mutated non-inducible transcription factor can be modified by replacing its own DNA recognition and binding domain with one of those mentioned above, and deleting the region of the protein that binds to any sort of inducing ligand or factor. In the steroid hormone transcription factors the ligand binding site is in the carboxy terminus. By deleting this region the transcription factor is no longer inducible and activates transcription in a constitutive manner (Hollenberg, S. M. and Evans, R. M., Cell 55, 899-906, 1988). In addition, one of the transcription factor's own transactivation domains can be duplicated within the protein, or a transactivation domain from another source can be added. Examples of transactivation domains that can be used include VP-16, TAF-1, TAF-2, TAU-1, TAU-2 and NFκB-p65.

Type B Gene Construct:

The type B gene construct(s) in this case will have an identical design to that described earlier for the double inducible multi-gene system 1.

The coding sequence for any desired protein can be placed downstream of the minimal promoter. Suitable 3' sequences are included for efficient expression in the tissue of choice.

In certain preferred embodiments of the invention, preferred constructs provide a polynucleotide sequence encoding any desired polypeptide. In particularly preferred embodiments of the invention, preferred constructs provide a polynucleotide sequence encoding $X_{LC}LACI_{K1}$, 9XKI, 7PC, 9PC and 10PC polypeptides of the invention in a multi- or single-gene system. In the single-gene system the polynucleotide sequence encoding a polypeptide is operably linked to the cis-acting signals necessary for expression in the desired tissue or bodily fluid of the transgenic organism. In the type A construct of the multi-gene system, cis-acting signals necessary for expression in the desired tissue of the transgenic organism are operably linked to a polynucleotide sequence encoding a mutated transcription factor. Particularly highly preferred in this regard are cis-acting signals that provide efficient expression in mammary glands with little or no expression elsewhere in the organism, as described in greater detail elsewhere herein. DNA polynucleotides are especially preferred.

Polypeptides

In a particular aspect the invention provides any polypeptide that can be expressed in a transgenic organism under the control of a multi-gene system. Particularly preferred embodiments in this regard provide $X_{LC}LACI_{K1}$, 9XKI and protein C polypeptides that provide therapeutic activity.

DNAs Encoding Polypeptides

Genetic constructs that encode polypeptides for use in making transgenic organisms in accordance with the invention can be obtained using standard molecular biology techniques, including but not limited to techniques for cloning, synthesizing and modifying DNAs, RNAs, and combinations thereof. Genomic DNA, minigenes and cDNAs are particularly preferred in this regard.

Genetic constructs, such as gDNA, minigenes or cDNA constructs, encoding polypeptides derived from a variety of organisms may be used in the invention and most highly preferred are those derived from genes and cDNAs of humans.

Genomic DNA, minigenes and cDNAs are preferred in some embodiments in this regard. Genomic DNAs that encode human polypeptides can be obtained, for instance, from libraries of human genomic DNA using probes based on the published DNA sequence of that human polypeptide and standard library screening and cloning techniques. Human cDNAs encoding polypeptides, for another example, can be obtained from cDNA libraries made from any tissue, such as liver or kidney, using much the same screening techniques and much the same probes as for human genomic DNAs. Minigenes can be constructed from genomic and/or cDNAs.

Genetic constructs that engender production of naturally occurring polypeptides are highly preferred in some aspects and preferred embodiments of the invention. Genetic constructs that engender production of genetically engineered, altered, mutated, and/or modified forms of a polypeptide are highly preferred in other aspects and preferred embodiments of the invention.

Modifications can be introduced into naturally occurring genes and polypeptides encoded thereby by techniques well known to the art, such as the synthesis of modified genes by ligation of overlapping oligonucleotides, substitution and/or deletion of domains or regions, and introduction of mutations directly into cloned genes, as by oligonucleotide mediated mutagenesis (Ausubel, F. M., et al., (eds): Current Protocols in Molecular Biology, 4th edition, Wiley, New York, 1999).

Particularly preferred modifications in this context include but are not limited to those that alter post-translational processing as discussed above, that alter size, that fuse portions of different proteins together, that alter the active site of the polypeptide, that stabilize the polypeptide, that control transport and/or secretion of the polypeptide, that alter, augment, multiply, decrease or eliminate physiological activities of the polypeptide.

Other preferred embodiments in this regard relate to modification that affect proteolytic processing, activation and inactivation of polypeptides by the natural series of proteolytic cleavages that occur during physiological processes, such as alteration to the sites of cleavage by thrombin, Factor Xa and protein C.

Further preferred embodiments in this regard relate to modifications that affect, alter, add to, or eliminate one or more of the post-translational modifications of the polypeptides of the invention. Certain particularly preferred embodiments in this regard relate to modifications that alter physiological functions and provide improved performance, such as improved activity, improved stability, improved properties for purification, and improved physiological persistence, among others.

Certain preferred embodiments in this regard relate to addition, deletion or alteration of sites to change the γ-carboxylation of polypeptides of the invention.

Certain preferred embodiments in this regard relate to addition, deletion or alteration of sites to change glycosylation of polypeptides of the invention.

Particularly preferred embodiments in this regard are those that improve glycosylation-dependent activities of polypeptides of the invention, such as physiological activities, including but not limited to enzymatic activity, substrate preferences, binding to cofactors and other moieties, complex formation, thermal stability, resistance to proteases and physiological persistence.

Cis-Acting Sequences for Transgenic Expression

A wide variety of genes have been expressed in a wide variety of transgenic organisms. Many blood proteins in particular have been expressed in animals. Moreover, transgenic expression of blood proteins has been targeted to specific compartments. The cis-acting controls used in the past to express blood proteins in transgenic organisms also are useful, in many cases, in expressing $X_{LC}LACI_{K1}$, 9XKI and protein C in transgenic organisms in accordance with some aspects of the present invention. Examples in this regard are described in Lubon et al., Transfusion Medicine Reviews X(2): 131-141 (1996) which is incorporated by reference herein in its entirety. Some preferred embodiments relating to expression-regulatory regions for transgenic expression of polypeptides in single or multi gene systems are described in further detail below.

Promoters and Related Sequences for Use in a Single Gene System and the Type A Construct in the Multi-Gene System The cis-acting regulatory regions useful in the invention include the promoter used to drive expression of a gene in a transgenic organism effective for production of polypeptides in the organism of the invention. Preferred in this regard are regulatory regions that engender the production of significant amounts of polypeptides of the invention that can be recovered from the organism, purified and, in preferred embodiments, activated. The term "engender production" refers to the case in which the regulatory regions in the single gene "classical" transgenic system are operably linked to the sequences to be expressed (coding sequences for a protein product) and secreted from a cell, prior to introduction into a cell. The term also encompasses the case in which the regulatory regions of the type A DNA construct, in a multi-gene system, are operably linked to the sequences to be expressed (a mutated transcription factor). This protein then transactivates expression of the type B construct(s), which produces the secreted protein product.

By Asignificant@ it is meant that the polypeptides of the invention can be recovered from the transgenic organism in amounts useful for research and/or for commerce. Preferred concentration ranges of the polypeptides in milk, especially useful for purification for various purposes, extends from approximately 0.01-20 g/L. It is understood, however, that the concentration range useful for purification will depend upon, for example, the protein being expressed and the organism in which it is produced. Accordingly, these ranges are not intended to be limiting but to provide guidance to preferred parameters.

Promoters and methods for producing proteins in milk of transgenic non-human mammals that can be used in accordance with preferred embodiments of the invention in this regard are described in, for instance, U.S. Pat. No. 4,873,316 of Meade et al. on Isolation of Exogenous Recombinant Proteins From The Milk of Transgenic Mammals; U.S. Pat. No. 5,880,327 of Lubon et al. on Transgenic Mammals Expressing Human Coagulation Factor VIII; and U.S. Pat. No. 5,831,141 of Lubon et al. on Expression of a Heterologous Polypeptide in Mammary Tissue of Transgenic Nonhuman Mammals Using a Long Whey Acidic Protein Promoter, each of which is incorporated herein by reference in its entirety regarding the foregoing particularly in parts pertinent to transgenic production of polypeptides in milk of transgenic non-human mammals.

Whey acidic protein (referred to as "WAP") promoters are among the most highly preferred promoters in this regard. Regulatory elements of the murine WAP gene are entered in GenBank (U38816) and cloned WAP gene DNAs are available from the ATCC.

Among the most preferred promoters are those that regulate a whey acidic protein (WAP) gene, particularly, the murine and the rat WAP promoter. In certain preferred embodiments of this invention the long or short mouse or rat WAP promoter is preferred.

Promoters of casein, lactalbumin and lactoglobulin genes also are preferred in certain embodiments of the invention in this regard, including, but not limited to the $\alpha$-, $\beta$-, $\kappa$- and $\gamma$-casein promoters and the $\alpha$-lactalbumin, lactoferrin and $\beta$-lactoglobulin promoters, and derivatives thereof.

A wide variety of inducible promoters are known that can be used in this regard, including as well as those above, those that can be induced by hormones, ligands and metals. A variety of such promoters, their inducible elements, and their induction are described in for example, Sambrook, J., et al. Molecular Cloning: A Laboratory Manual, 3rd Ed., Cold Spring Harbor Laboratory Press, Cold Spring Harbor, N.Y. (2000), which is herein incorporated by reference in its entirety in part pertinent to promoters and induction.

Among the sequences that regulate transcription that are useful in the invention, in addition to the promoter sequences discussed above, are enhancers, splice signals, transcription termination signals and polyadenylation sites, among others. Particularly useful regulatory sequences include those that increase the efficiency of expression of polypeptides of the invention in transgenic organisms. Also particularly preferred in this regard are those that increase the specificity of expression of those polypeptides in targeted compartments of a transgenic organism. Among particularly highly preferred regulatory regions in this regard are those that increase the efficiency, the specificity or both the efficiency and the specificity of expression of the polypeptides of the invention in mammary glands and in the milk of transgenic non-human mammals.

3' Untranslated Sequences

Also among regulatory sequences preferred in certain embodiments of the invention are sequences situated in the 3' untranslated portion of genes that increase expression of transgenically-encoded products, particularly in the targeted tissue/bodily fluid, such as eggs and or mammary gland cells of transgenic non-human mammals, especially those that increase the amount of the product secreted into the milk. Among highly preferred particular sequences in this regard are those that apparently stabilize mRNA transcribed from transgenes. Among preferred embodiments in this regard are sequences that comprise a polyadenylation signal. Among preferred regions of this type are those derived from the genes for proteins that are expressed at high levels in mammary gland cells and or encode proteins that are found at high concentrations in milk. Especially preferred in this regard are sequences of the 3' untranslated region of whey acidic protein genes, particularly the mouse and rat whey acidic protein genes.

Trafficking and Translational Signals

Also important to the invention are signal peptide sequences that direct secretion of proteins into the desired compartment of a transgenic organism. In this regard, both endogenous and heterologous signal sequences are useful in the invention. Generally, the signal peptides of proteins normally secreted into the chosen compartment are useful in the invention. The signal sequences of proteins that occur in high concentration in targeted tissues are particularly preferred, such as the signal peptides of the albumins, lysozymes, whey acidic proteins, caseins, lactalbumins, transferrins and lactoglobulins, including, but not limited to the signal peptides of the $\alpha$-, $\beta$ and $\gamma$-caseins and $\alpha$-lactalbumin and $\beta$-lactoglobulin. Also among preferred signal sequences in this regard are the signal peptides of the polypeptides of the invention, secreted anti-coagulation factors.

Also, especially useful in the present invention are sequences that advantageously modulate post-translational modifications of transgenic polypeptides produced in accordance with the invention herein described.

Organisms

A wide variety of hosts can be used for transgenic production of polypeptides in accordance with the present invention. Particularly preferred are those that provide the polypeptides with the post-translational modifications required for physiological activity. Especially preferred in this regard are those that provide high specific activity and those that provide high yields. Most especially preferred in this regard are those that provide high yields of high specific activity polypeptides. Organisms that do not suffer adverse effects of transgenesis and or transgene expression are similarly preferred, as are those that do not suffer adverse effects from production, accumulation or harvesting of transgenically expressed polypeptides.

All non-human mammals are preferred in this regard, particularly preferred mammals in this regard include domesticated livestock mammals. Particularly preferred mammals include mice, rats, rabbits, pigs, sheep, goats and cows. Of these, pigs are especially particularly preferred.

Harvesting and Purification

A wide variety of well known techniques may be employed to isolate and purify polypeptides from transgenic organisms in accordance with the invention. (Degener, A., et al, J. Chrom. A, 799, 125-137, 1998; Van Cott, K. E., et al., J. Mol. Recog. 9, 407-414, 1996)

The polypeptide of the invention contained in bodily fluids such as milk or eggs, can be purified by known means without unduly affecting activity. Generally, it is preferred that transgenic polypeptides in milk produced pursuant to the present invention should be isolated as soon as possible after the milk is obtained from the transgenic mammal, to mitigate any deleterious effect(s) of milk components on the structure or function of the polypeptide. Preferred methods include those that use one or more of centrifugation, cryoprecipitation, ion-induced precipitation, anion exchange, and/or immunochromatography to purify the transgenic polypeptide from milk or whey. For the most part the methods are employed conventionally. Representative methods in this regard are described in, among others, Bringe et al., J. Diary Res. 56: 543 et seq. (1989) which is incorporated herein by reference in parts pertinent to methods that can be used in whole or part to purify transgenic polypeptides from transgenic milk.

There are proteases in milk that may degrade proteins, including transgenically expressed proteins. The main proteases in milk thus far identified are alkaline proteases with tryptic and/or chymotryptic activities, a serine protease, a chymotrypsin-like enzyme, an aminopeptidase and an acid protease. Methods may be employed for isolation and purification of transgenic polypeptides that prevent proteolytic degradation by endogenous milk proteases, such as those noted above. Among preferred methods in this regard are rapid processing of whole milk, the use of low temperatures that inhibit protease activity and/or decrease degradation of transgene products in milk and the use of protease inhibitors. Specific inhibitors that may be useful in this regard are well known to those of skill, and are widely available from commercial reagent suppliers such as Sigma Chemical Company.

Uses

The recombinant polypeptides of this invention have many uses. This includes medically related uses for both non-human and human subjects, which includes clinical applications. Examples include the use of protein C and $X_{LC}$-LACI$_{K1}$ proteins for treating the coagulopathy which is associated with sepsis, and other conditions associated with the need for anti-coagulation.

The present invention is further described by reference to the following, illustrative examples.

Example 1

Construction and Production of the 4.1 kbp Murine Whey Acidic Protein (mWAP) Promoter Driven XKI-cDNA Construct (WAP6XKI) for Microinjection into Embryos to Produce Transgenic Animals The WAP6XKI construct uses the regulator elements of the mouse WAP gene to express coding sequences of the Factor X light chain linked to the Kunitz domain 1 of Tissue Factor Plasminogen Inhibitor. Specifically, the 4.1 kbp long mouse WAP (lmWAP) promoter described in (Paleyanda et al., Transgene Res., 3 (1994) pp. 335-343) is used to direct expression of coding sequences of the Factor X light chain linked to the Kunitz domain 1 of Tissue Factor Plasminogen Inhibitor as referenced in (Girard et al. Science, 248 (1990) pp. 1421-1424) that is followed by the ~1.6 kbp mouse Whey Acidic Protein (mWAP) 3'UTR (C. Russell, dissertation "Improvement of Expression of Recombinant Human Protein C in the Milk of Transgenic Mammal Using a Novel Transgenic Construct," Virginia Polytechnic Institute, Blacksburg, Va. (December 1993)) coding for the polyadenylation signal. Assembly of the WAP6XKI and its purification for microinjection is by routine recombinant DNA techniques known to the skilled artisan that can be found, for example, in Sambrook et al., MOLECULAR CLONING, A LABORATORY MANUAL, Vol. 1-3 (Cold Spring Harbor Press 1989).

Step 1. Production of the Plasmid pXKI

The plasmid pXKI was assembled from the coding segment of factor X light chain (first 179 amino acids) and the Kunitz domain 1 (KI) coding segment of Tissue Factor Plasminogen Inhibitor (TFPI) and placed in the vector pGEM7 (Promega; Madison, Wis.), (FIG. 1). Generation of the Factor X fragment was by PCR of clone CS0DB007YC01 (Research Genetics), Genebank Accession AL521984, with primers that introduced a Kpn I endonuclease recognition site 5' of the prepropeptide coding sequence and produced a fragment that extended through the naturally occurring Apa I endonuclease recognition sequence of the light chain. Primers were KpnIFXS1, 5'caggtaccatggggcgcccactgcac3' and FXA1 5'cgttccagggtctgtttcccac3'. The PCR product of 543 bp in size was gel purified and digested with the endonucleases Kpn I and Apa I. Generation of the KI fragment was by PCR of clone CS0DI021YI01 (Research Genetics), Genebank Accession AL544620 with primers that introduced an Apa I recognition sequence 5' of the Kunitz domain comprising the following peptide sequence:

TDTELPPLKLMHSFCAFKADDGPC-KAIMKRFFFNIFTRQCEEFIYGGCE GNQNRFESLR-RCKKMCTRDNANRIIKTTMH

Followed by a Kpn I recognition sequence 3' of the last Histidine residue. Primers were TFFXadS1 5'-ttcgggccctac-cccacagatacggagttgccacc and TfendA1 5'gcaggtacctagtgeat-tgttgtctataatcctgtt. The resulting PCR product of 262 bp was gel purified and digested with the endonucleases Kpn I and Apa I. The Factor X and KI fragments were then ligated into the vector pGEM7 that was linearized by Kpn I digestion and dephosphorylated using Calf Intestine Alkaline Phosphatase (CLAP, Promega). The ligation mixture was then used to transform competent E. coli cells and transformants were screened. Screening was by Blue/white selection on X-gal plates. White colonies were selected and the presence of the vector verified by cutting with Kpn I and observing the 786 bp band after gel electrophoresis.

Step 2. Production of the Plasmid pUCWAP6XKI

The plasmid pUCWAP6XKI was produced by inserting the XKI coding portion of pXKI into the expression vector pUCWAP6 (FIG. 2). Specifically, the plasmid pUCWAP6 as described in (S. Butler, thesis "Production and Secretion of Recombinant Human Fibrinogen by the Transgenic Murine Mammary Gland", Virginia Polytechnic Institute, Blacksburg, Va. (May, 1997)) containing the 4.1 kbp lmWAP promoter and ~1.6 kbp mWAP 3'UTR was cut with the endonuclease Acc65I and dephosphorylated using CIAP followed by gel purification. This vector was then ligated with the coding portion of XKI that was removed from pXKI by digest with Acc65I and gel purified. The ligation mixture was used to transform competent E. coli cells and transformants were screened. Colonies of transformed E. coli were screened by polymerase chain reaction for the presence of the vector and the insert in the correct orientation by using the following primers: XKIS1, 5' gcatcccagacactcagaca 3' and XKIA1, 5'tggcagaactggtcacagtc3' under the following conditions: 95° C. for 2 min then 40 cycles of annealing 55° C. for 30 sec, denaturation 95° C. for 30 sec and elongation 72° C. for 45 sec. Presence of a 490 bp band indicated correct orientation in the vector. The final construct (WAP6) was verified by DNA sequence analysis.

Step 3. Preparation of WAP6XKI DNA for Microinjection.

The DNA fragment used for microinjection of early stage embryos was prepared by endonuclease digestion of pUCWAP6XKI with the enzyme Not I followed by separation from bacterial elements by agarose gel electrophoresis. The ~6.7 kbp fragment was excised from the gel and purified by using a gel extraction kit (UltraClean 15, MoBio Labs, Solana Beach, Calif.) followed by standard methods of chloroform/phenol extraction and ethanol precipitation. DNA was suspended in TE (10 mM Tris pH 7.4, 1 mM EDTA) and diluted to a concentration of 5 μg/ml.

Example 2

Production of WAP6XKI Transgenic Mice

Step 1. Transgenic mice were produced essentially as described by Hogan et al., *Manipulating the Mouse Embryo*, Cold Spring Harbor Press, (1986), which is hereby incorporated by reference. That is, glass needles for micro-injection were prepared using a micropipet puller and microforge.

Injections were performed using a Nikon microscope having Hoffman Modulation Contrast optics, with Narashigi micromanipulators and a pico-injector driven by $N_2$ (Narashigi). Fertilized mouse embryos were surgically removed from oviducts of superovulated female CD-1 mice and placed into M2 medium. Cumulus cells were removed from the embryos with hyaluronidase at 300 µg/ml. The embryos were then rinsed in new M2 medium, and transferred into M15 medium for storage at 37 degrees centigrade prior to injection. Stock solutions containing about 5 µg/ml of the above described DNA were prepared and microinjected into the mouse embryos. After microinjection, embryos were implanted into avertin-anesthetized CD-1 recipient females made pseudo-pregnant by mating with vasectomized males. About 25-30 microinjected mouse embryos per recipient were transferred into pseudopregnant females.

Step 2. DNA from mice born after embryo transfer was isolated by digesting tail tissue in 50 mM Tris-HCl, 0.15 M NaCl, 1 M $Na_2ClO_4$, 10 mM EDTA, 1% sodium dodecylsulfate, 1% 2-mercaptoethanol, 100 ug/ml proteinase K, pH 8.0. 750 µl of lysate was extracted with 250 µl chloroform/phenol (1:1) followed by precipitation with isopropanol 0.7 volumes, washed in 70% ethanol and dried. DNA was suspended in TE (10 mM Tris-HCl and 10 mM EDTA pH 8.0). Mice produced after embryo transfer of microinjected embryos were screened by Southern analysis. 10 µg of DNA isolated from tail tissue was digested with the endonuclease Pst I and subjected to agarose gel electrophoresis and transferred to a nylon membrane. The membrane was probed with a $^{32}P$ labeled DNA fragment of WAP6XKI consisting of the Bgl II to Kpn I (~1.5 kbp) promoter fragment. Hybridization was carried out at 68° C. for 4 hours using Quick Hyb (Stratagene; LaJolla, Calif.). Following standard washing methods, the membrane was subjected to autoradiography (−70° C.) for a period of 24 hours. Transgenic mice were identified by the presence of a ~2.4 kbp size band.

Step 3. Out of 36 pups born, 3 were shown to be transgenic for WAP6XKI sequences. These animals were matured and at a suitable age, mated.

Example 3

Production and Analysis of Milk from WAP6XKI Transgenic Mice

Step 1. Collection of Mouse Milk from WAP6XKI Mice.

Females were removed from their pups for approximately 1 hour prior to milking to allow for milk accumulation. Females from the three established transgenic lines were anesthetized with 0.4 ml of Avertin (Hogan et al., *Manipulating the Mouse Embryo*, Cold Spring Harbor Press, (1986)) and induced to let down milk by intramuscular administration of 5.0 IU of oxytocin (Vedco Inc., St. Joseph, Mo.). Milk was collected into 1.8 ml screw cap microcentrifuge tubes using capillary tubes (Kimax brand, 2.0 mm i.d.) that were flame-polished to prevent tissue damage. The capillary was partially inserted into a stoppered hand-held receiving chamber containing the microcentrifuge tube. The milk was collected from the capillary directly into the microcentrifuge tube while operating the receiving chamber at 12 cm $H_2O$ vacuum. Upon collection of 150 to 500 µl of milk, the tubes were stored at −40° C. until the final whey preparation stage.

Step 2

Example 4

Production of WAP6XKI Transgenic Pigs

Step 1. Pig embryos are recovered from the oviduct, and placed into a 1.5 ml microcentrifuge tube containing approximately 0.5 ml embryo transfer media (Beltsville Embryo Culture Medium). Embryos are centrifuged for 12 minutes at 16,000×g RCF (13,450 RPM) in a microcentrifuge (Hermle, model Z231). The embryos are then removed from the microcentrifuge tube with a drawn and polished Pasteur pipette and placed into a 35 mm petri dish for examination. Embryos are then placed into a microdrop of media (approximately 100 µl) in the center of the lid of a 100 mm petri dish, and silicone oil is used to cover the microdrop and fill the lid to prevent media from evaporating. The petri dish lid containing the embryos is set onto an inverted microscope (Carl Zeiss) equipped with both a heated stage and Hoffman Modulation Contrast optics (200× final magnification). A finely drawn (Kopf Vertical Pipette Puller, model 720) and polished (Narishige microforge, model MF-35) micropipette is used to stabilize the embryos while about 1-2 picoliters of stock solution (5 µg/ml) of the above described DNA is microinjected into the non-pronuclear stage pig embryos using another finely drawn micropipette. Embryos surviving the microinjection process as judged by morphological observation are loaded into a polypropylene tube (2 mm ID) for transfer into the recipient pig. About 40-50 microinjected embryos are transferred into each hormonally synchronized surrogate mother recipient female pig.

Step 2. Pigs produced after embryo transfer of WAP6XKI microinjected embryos are screened by Southern analysis. 10 µg of DNA isolated from tail tissue (as described above for mice) is digested with the endonuclease Pst I and subjected to agarose gel electrophoresis and transferred to a nylon membrane. The membrane is probed with a $^{32}P$ labeled DNA fragment of WAP6XKI consisting of the Bgl II to Kpn I (~1.5 kbp) promoter fragment. Hybridization is carried out at 68° C. for 4 hours using Quick Hyb (Stratagene; LaJolla, Calif.). Following standard washing methods, the membrane is subjected to autoradiography (−70° C.) for a period of 24 hours. Transgenic pigs are identified by the presence of a ~2.4 kbp size band.

Example 5

Production and Analysis of Milk from WAP6XKI Transgenic Pigs

Step 1. Collection of Pig Milk from WAP6XKI Pigs.

Lactating sows are injected intramuscularly with 30-60 IU of oxytocin (Vedco Inc., St. Joseph, Mo.), to stimulate milk let-down. Letdown occurs two to five minutes after injection. Pigs are milked by hand during the course of this study. Immediately after collection the milk is diluted 1:1 with 200 mM EDTA, pH 7.0 to solubilize the caseins and then frozen. Small aliquots (about one milliliter) of the milk EDTA mixture are taken and centrifuged for approximately 30 minutes at 16000×g at 4° C. The fat layer is separated from the diluted whey fraction, and the diluted whey fraction is used for all further assays.

Step 2. Detection of High Levels of Recombinant XKI in Milk of Transgenic Mice and Pigs by Western Blot Analysis.

Recombinant XKI produced in the milk of transgenic animals is examined using the well known method of Western Blot Analysis. Samples are treated in the same way as those containing recombinant Protein C and thus daily samples of EDTA-diluted whey are prepared as described in Velander et al., Annals of the New York Academy of Sciences, 665 (1992) 391-403. Western Blot analysis is also as described in the same reference and as is well known in the prior art. Briefly, the samples are electrophoresed on 8-16% SDS gels (Novex, San Diego). Approximately 125 ng of XKI containing whey samples, recombinant human Factor X (as determined by polyclonal ELISA) reference standards and human protein C standards derived from plasma are loaded into the gel lanes. A total of 25 µg of total protein from a pool of non-transgenic (NTG) whey is loaded on the gels. After electrophoresis, proteins are transferred overnight to PVDF membranes (Bio Rad). The membranes are washed for 30 minutes in TBST, blocked with TBS/0.05% Tween 20/0.5% Casein (TBST-Casein). The membranes are developed with rabbit anti-Factor X antibody (1: 1000 in TBST-Casein for 45 minutes at 37° C.), followed by anti-rabbit IgG/HRP (Sigma) (1:1000 in TBST-Casein for 45 minutes at 37° C.), and the DAB metal enhanced staining (Pierce). Molecular weight markers are purchased from Bio-Rad. The presence of about greater than 50 ug/ml of properly processed XKI in the milk of transgenic mice and 300 ug/ml in the milk transgenic pigs is detected by the presence of a 30 kDa immunostained band as detected by the Western Blot Analysis method.

Step 3. Purification and Biological Activity of Highly Carboxylated XKI from the Milk of Transgenic Mice and Pigs.

The immunoaffinity chromatographic process well described by Velander et al., Annals of the New York Academy of Sciences, 665 (1992) 391-403 is used to purify those fractions of Protein C from the milk of transgenic mice is also applicable to XKI. The 7D7B10 Monoclonal Antibody is also cross reactive with the gla domain of XKI and this is well discussed in Orthner et al., J Biological Chemistry, 264 (1989) 18781-18788. This monoclonal antibody is used to isolate those XKI fractions that are properly gamma-carboxylated. The biological activity of the XKI fractions that are properly carboxylated and purified by the 7D7B10 monoclonal antibody described in the above reference is assessed by inhibition of factor VIIIa-TF complex as is well described in T. J. Girard et al., Thromb. Res. 46 (1987) p37 and in Girard et al., Science 248 (1990) 1421-1424. More that 50 ug/ml of properly carboxylated and active XKI is detected in the material from the milk of mice and more than 300 ug/ml of properly carboxylated XKI and active XKI is detected in the milk of transgenic pigs by the above procedure.

Example 6

Construction and Production of the 4.1 kbp mWAP Driven 9XKI-cDNA Construct (WAP69XKI) for Microinjection into Embryos to Produce Transgenic Animals The expression vector WAP69XKI contains coding segments of the Factor IX prepropeptide linked to Factor X light chain (minus its prepropeptide) linked to the Kunitz domain 1 of Tissue Factor Plasminogen Inhibitor placed under expression control of the long form of the murine Whey Acidic Protein (lmWAP) promoter.

Step 1. Production of the Plasmid p9XKI.

The plasmid p9XKI is a compilation of sequences coding for the propeptide of Factor IX linked to Factor X light chain (with out propeptide) linked to the Kunitz domain 1 (KI) of TFPI (FIG. 3). The plasmid was assembled in three phases. First, the propeptide of Factor IX was obtained by PCR of the plasmid pUCWAPFIX (Van Cott et al., Genetic Analysis, 15 (1999) pp. 155-160) from the Kpn I site to the Eae I in the Factor IX cDNA. PCR primers were: KpnFIXs1, 5' ctggtac-catgcagcgcgtgaacatg and FIX A1, 5'-ctatggcccctcttttggccgat-tcag-3'. The 150 bp PCR product was then cut with the endonucleases Kpn I and Eae I. The second phase was to PCR the Factor X gene using clone CS0DB007YC01 (Research Genetics), Genebank Accession AL521984 as template to generate an Eae I site 5' of the mature protein coding sequence (amino acid arginine at position 40 of unprocessed Factor X) and going through the naturally occurring Apa I endonuclease site. PCR primers are FXEaeS2, 5'-cggccaaagagggccaattc-ctttcttg-3' and FXA1 5'cgttccagggtctgtttcccac3'. This was followed by digesting the PCR fragment with Eae I and Apa I. The two PCR fragments, Factor IX propeptide and Factor X for 9XKI were ligated into the pGEM7 vector after dual digest with Kpn I and Apa I resulting in the vector p9X. The third phase involved cloning the KI fragment of TFPI and ligating it with the 9X fragment. Generation of the KI fragment was by PCR of clone CS0DI021YI01 (Research Genetics), Genebank Accession AL544620 with primers that introduced an Apa I recognition sequence 5' of the Kunitz domain comprising of the following peptide sequence:

TDTELPPLKLMHSFCAFKADDGPC-KAIMKRFFFNIFTRQCEEFTYGGCE GNQNRFESLR-RCKKMCTRDNANRIIKTTMH

Followed by a Kpn I recognition sequence 3' of the last Histidine residue. Primers were TFFXadS1 5'-ttcgggccctac-cccacagatacggagttgccacc and TfendA1 5'gcaggtacctagtgcat-tgttgtctttataatcctgtt. The resulting PCR product of 262 bp was gel purified and digested with the endonucleases Kpn I and Apa I. The KI fragment was ligated to the 9X fragment cut out of p9X with the endonucleases Kpn I and Apa I and gel purified. Added to the ligation of these fragments was pGEM that was digested with Kpn I and dephosphorylated. The ligation mixture was used to transform competent E. coli cells and transformants were screened. Screening was by Blue/white selection on X-gal plates. White colonies were selected and the presence of the insert verified by cutting with Kpn I and observing the 798 bp band after gel electrophoresis.

Step 2. Production of the Plasmid pUCWAP69XKI.

The plasmid pUCWAP69XKI was produced by inserting the 9XKI coding portion of p9XKI into the expression vector pUCWAP6 (FIG. 4). Specifically the plasmid pUCWAP6 was cut with the endonuclease Acc65I and dephosphorylated using CIAP followed by gel purification. This vector was then ligated with the coding portion of 9XKI that was removed from p9XKI by digestion with Acc65I and gel purified. The ligation mixture was used to transform competent E. coli cells and transformants were screened. Colonies of transformed E. coli were screen by polymerase chain reaction for the presence of the vector and the insert in the correct orientation by using the following primers: XKIS1, 5' gcatcccagacactcagaca 3'and XKIA1, 5'tggcagaactggtcacagtc3' under the following conditions: 95° C. for 2 min then 40 cycles of annealing 55° C. for 30 sec, denaturation 95° C. for 30 sec and elongation 72° C. for 45 sec. Presence of a 490 bp band indicated correct orientation in the vector. The plasmid pUCWAP69XKI was verified by DNA sequence analysis.

Step 3. Preparation of WAP69XKI DNA for Microinjection.

The DNA fragment suitable for microinjection of early stage embryos is prepared by endonuclease digestion of pUCWAP69XKI with the enzyme Not I followed by separation from bacterial elements by agarose gel electrophoresis. The ~6.7 kbp fragment is excised from the gel and purified by using a gel extraction kit (UltraClean 15, MoBio Labs, Solana Beach, Calif.) followed by chloroform/phenol extraction, ethanol precipitation and suspension in TE (10 mM Tris pH 7.4, 1 mM EDTA). The fragment is further purified by subjecting the fragment to ultracentrifugation through a standard NaCl gradient. DNA is diluted to a concentration of 5 μg/ml for microinjection.

Example 7

Production of WAP69XKI Transgenic Mice

Step 1. Transgenic mice are produced essentially as described by Hogan et al., *Manipulating the Mouse Embryo*, Cold Spring Harbor Press, (1986), which is hereby incorporated by reference. That is, glass needles for microinjection are prepared using a micropipet puller and microforge. Injections are performed using a Nikon microscope having Hoffman Modulation Contrast optics, with Narashigi micromanipulators and a pico-injector driven by $N_2$ (Narashigi). Fertilized mouse embryos are surgically removed from oviducts of superovulated female CD-1 mice and placed into M2 medium. Cumulus cells are removed from the embryos with hyaluronidase at 300 μg/ml. The embryos are then rinsed in new M2 medium, and transferred into M15 medium for storage at 37 degrees centigrade prior to injection. Stock solutions containing about 5 μg/ml of the above described DNA are prepared and microinjected into the mouse embryos. After microinjection, embryos are implanted into avertin-anesthetized CD-1 recipient females made pseudo-pregnant by mating with vasectomized males. About 25-30 microinjected mouse embryos per recipient are transferred into pseudopregnant females.

Step 2. DNA from mice born after embryo transfer is isolated by digesting tail tissue in (50 mM Tris-HCl, 0.15 M NaCl, 1 M $Na_2ClO_4$, 10 mM EDTA, 1% sodium dodecylsulfate, 1% 2-mercaptoethanol, 100 ug/ml proteinase K, pH 8.0). 750 μl of lysate is extracted with 250 μl chloroform/phenol (1:1) followed by precipitation with isopropanol 0.7 volumes, washed in 70% ethanol and dried. DNA is suspended in TE (10 mM Tris-HCl and 1 mM EDTA pH 8.0). Mice produced after embryo transfer of microinjected embryos are screened by Southern analysis. 10 μg of DNA isolated from tail tissue is digested with the endonuclease Pst I and subjected to agarose gel electrophoresis and transferred to a nylon membrane. The membrane is probed with a $^{32}P$ labeled DNA fragment of WAP69XKI consisting of the Bgl II to Kpn I (~1.5 kbp) promoter fragment. Hybridization is carried out at 68° C. for 4 hours using Quick Hyb (Stratagene; LaJolla, Calif.). Following standard washing methods, the membrane is subjected to autoradiography (−70° C.) for a period of 24 hours. Transgenic mice are identified by the presence of a ~2.4 kbp size band.

Example 8

Production of WAP69XKI Transgenic Pigs

Step 1. Pig embryos are recovered from the oviduct, and placed into a 1.5 ml microcentrifuge tube containing approximately 0.5 ml embryo transfer media (Beltsville Embryo Culture Medium). Embryos are centrifuged for 12 minutes at 16,000×g RCF (13,450 RPM) in a microcentrifuge (Hermle, model Z231). The embryos are then removed from the microcentrifuge tube with a drawn and polished Pasteur pipette and placed into a 35 mm petri dish for examination. Embryos are then placed into a microdrop of media (approximately 100 μl) in the center of the lid of a 100 mm petri dish, and silicone oil is used to cover the microdrop and fill the lid to prevent media from evaporating. The petri dish lid containing the embryos is set onto an inverted microscope (Carl Zeiss) equipped with both a heated stage and Hoffman Modulation Contrast optics (200× final magnification). A finely drawn (Kopf Vertical Pipette Puller, model 720) and polished (Narishige microforge, model MF-35) micropipette is used to stabilize the embryos while about 1-2 picoliters of stock solution (5 μg/ml) of the above described DNA is microinjected into the non-pronuclear stage pig embryos using another finely drawn micropipette. Embryos surviving the microinjection process as judged by morphological observation are loaded into a polypropylene tube (2 mm D) for transfer into the recipient pig. About 40-50 microinjected embryos are transferred into each hormonally synchronized surrogate mother recipient female pig.

Step 2. Pigs produced after embryo transfer of WAP69XKI microinjected embryos are screened by Southern analysis. 10 μg of DNA isolated from tail tissue (as described above for mice) is digested with the endonuclease Pst I and subjected to agarose gel electrophoresis and transferred to a nylon membrane. The membrane is probed with a $^{32}P$ labeled DNA fragment of WAP69XKI consisting of the Bgl II to Kpn I (~1.5 kbp) promoter fragment. Hybridization is carried out at 68° C. for 4 hours using Quick Hyb (Stratagene; LaJolla, Calif.). Following standard washing methods, the membrane is subjected to autoradiography (−70° C.) for a period of 24 hours. Transgenic pigs are identified by the presence of a ~2.4 kbp size band.

Example 9

Construction and Production of the 2.5 kbp mWAP Driven FIX-Protein C-cDNA (WAP5-9-PC) Construct for Microinjection into Embryos to Produce Transgenic Animals The expression vector WAP5-9-PC contains coding sequences of the prepropeptide of human FIX linked to sequences of the mature Protein C peptide placed under expression control of the short form of the murine Whey Acidic Protein (smWAP) promoter. Specifically, the 2.5 kbp smWAP promoter described in (Van Cott et al., *Genetic Analysis*, 15 (1999) pp. 155-160) is used to direct expression of coding sequences of the Factor IX propeptide linked to coding sequences for the mature Protein C peptide (Foster and Davie, PNAS, 81 (1984) pp. 4766-4770) that is followed by ~1.6 kbp of mouse Whey Acidic Protein (mWAP) 3'UTR (C. Russell, dissertation "Improvement of Expression of Recombinant Human Protein C in the Milk of Transgenic Mammal Using a Novel Transgenic Construct," Virginia Polytechnic Institute, Blacksburg, Va. (December 1993)) coding for the polyadenylation signal. Assembly of the WAP5-9-PC and its purification for microinjection is by routine recombinant DNA techniques known to the skilled artisan that can be found, for example, in Sambrook et al., MOLECULAR CLONING, A LABORATORY MANUAL, Vol. 1-3 (Cold Spring Harbor Press 1989).

Step 1. Production of the Plasmid pUCWAP5-9-PC

The hybrid protein, 9-Protein C contains the prepropeptide of human FIX linked to the mature Protein C peptide. The propeptide of Factor IX is obtained by PCR of the plasmid WAPFIX (Van Cott et al., *Genetic Analysis*, 15 (1999) pp. 155-160) from the Kpn I site to the Eae I in the Factor IX cDNA. PCR primers are: KpnFIXs1, 5' ctggtaccatgcagcgcgt-gaacatg and FIX A1, 5'-ctatggccctctttggccgattcag-3'. The 150 bp PCR product is cut with the endonucleases Kpn I and Eae I. Then the 5' fragment of mature Protein C is obtained by PCR using primers that will introduce endonuclease sites of EaeI on the 5' end of the PCR product and EcoRI on the 3' end. PCR primers are: PCEaeS1 (5'-atacggccaaagagggccaactcct-tcctgg) and PCEcoA1 (5'-ctagaattcgatctacttggtctt) that produce a 526 bp fragment spanning across a unique Sal I endonuclease site located ~150 bp into the mature Protein C coding sequence. After cutting with Eae I and EcoRI, this fragment along with that coding for the prepropeptide of FIX is inserted (ligated) into the vector pGem7 that is digested with Kpn I and EcoRI (FIG. 5). Competent *E. coli* are transformed with the ligation mixture and transformants screened by blue/white selection with X-gal. White transformants are then verified by digesting the corresponding plasmids with Kpn I and EcoRI and observing the 526 bp fragment after agarose gel electrophoresis. The resulting plasmid is digested with Sal I and EcoRI endonucleases, and the vector fragment containing the hFIX prepropeptide linked to the Protein C Sal I fragment, is gel purified. This vector fragment is then the acceptor for the Sal I to EcoRI fragment cut from pWAPPC3 3'UTR (C. Russell, dissertation "Improvement of Expression of Recombinant Human Protein C in the Milk of Transgenic Mammal Using a Novel Transgenic Construct," Virginia Polytechnic Institute, Blacksburg, Va. (December 1993)) that contains the mature peptide for Protein C from the Sal I site linked through the mWAP 3'UTR to the EcoRI end (FIG. 6). Competent *E. coli* are transformed with the ligation mixture and transformants screened by digestion with Kpn I, with observance of the ~1.4 kbp band after gel electrophoresis. The new construct coding for the hFIX prepropeptide linked to the mature Protein C peptide is removed by Kpn I digestion and ligated into the expression cassette pUCWAP5 that has been digested with Kpn I and treated with CLAP. Competent *E. coli* are transformed with the ligation mixture and transformants screened by PCR using the primers lmWAP for (5'-atgcatccagacactcaga) and PCEcoA1 (5'-ctagaattcgatctact-tggtctt). Observance of a ~700 bp band indicates presence of the insert in the correct orientation. Final verification is by DNA sequence analysis.

Step 3. Preparation of WAP5-9-PC DNA for Microinjection.

The DNA fragment suitable for microinjection of early stage embryos is prepared by endonuclease digestion of pUCWAP5-9-PC with the endonuclease EcoRI followed by separation from bacterial elements by agarose gel electrophoresis. The ~5.5 kbp fragment is excised from the gel and purified, followed by ethanol precipitation and suspension in TE (10 mM Tris pH 7.4, 1 mM EDTA). The fragment is further purified by subjecting the fragment to ultracentrifugation through a standard NaCl gradient. DNA concentration is determined by agarose gel electrophoresis by staining with ethidium bromide and comparing the fluorescent intensity of an aliquot of the DNA with the intensity of standards. Samples are then adjusted to 5 μg/ml.

Example 10

Production of WAP5-9-PC Transgenic Mice

Step 1. Mice, transgenic for the construct WAP5-9-PC are produced essentially as described in Example 7.

Step 2. DNA from mice born after embryo transfer is isolated by digesting tail tissue in (50 mM Tris-HCl, 0.15 M NaCl, 1 M $Na_2ClO_4$, 10 mM EDTA, 1% sodium dodecylsulfate, 1% 2-mercaptoethanol, 100 ug/ml proteinase K, pH 8.0). 750 μl of lysate is extracted with 250 μl chloroform/phenol (1:1) followed by precipitation with isopropanol 0.7 volumes, washed in 70% ethanol and dried. DNA is suspended in TE (10 mM Tris-HCl and 1 mM EDTA pH 8.0). Mice produced after embryo transfer of microinjected embryos are screened by Southern analysis. To confirm the presence of the WAP5-9-PC transgene, 10 μg of DNA isolated from tail tissue is digested with the endonuclease Kpn I and subjected to agarose gel electrophoresis and transferred to a nylon membrane. The membrane is probed with a $^{32}P$ labeled DNA fragment consisting of the 9-PC cDNA (~1.4 kbp). Hybridization is carried out at 68° C. for 4 hours using Quick Hyb (Stratagene; LaJolla, Calif.). Following standard washing methods, the membrane is subjected to autoradiography (–70° C.) for a period of 24 hours. Observance of a ~1.4 kbp band indicates the presence of the transgene.

Step 3. Mice transgenic for WAP5-9-PC are matured and mated. Milk is collected as described in Example 3.

Step 4. Detection of high levels of recombinant variant human Protein C in milk of transgenic mice and pigs by Western Blot Analysis.

Recombinant human Protein C produced from a Protein C mutant having a Factor IX propeptide is examined using Western Blot Analysis. Daily samples of EDTA-diluted whey are prepared as described in Velander et al., Annals of the New York Academy of Sciences, 665 (1992) 391-403. Western Blot analysis is also as described in the same reference and as is well known in the prior art. Briefly, the samples are electrophoresed on 8-16% SDS gels (Novex, San Diego). Approximately 125 ng of recombinant human Factor IX (as determined by polyclonal ELISA) and human protein C standard derived from plasma are loaded into the gel lanes. A total of 25 μg of total protein from a pool of non-transgenic (NTG) whey is loaded on the gels. After electrophoresis, proteins are transferred overnight to PVDF membranes (Bio Rad). The membranes are washed for 30 minutes in TBST, blocked with TBS/0.05% Tween 20/0.5% Casein (TBST-Casein). The membranes are developed with rabbit anti-Protein C antibody (1:1000 in TBST-Casein for 45 minutes at 37° C.), followed by anti-rabbit IgG/HRP (Sigma) (1:1000 in TBST-Casein for 45 minutes at 37° C.), and the DAB metal enhanced staining (Pierce). Molecular weight markers are purchased from Bio-Rad. The presence of about greater than 50 ug/ml of properly processed Protein C in the milk of transgenic mice and 300 ug/ml in the milk of transgenic pigs is detected by the Western Blot Analysis method.

Step 5. Purification and biological activity by APTT of highly carboxylated Protein C from the milk of transgenic mice and pigs having a chimeric protein C with a FIX propeptide.

The immunoaffinity chromatographic process well described by Velander et al., Annals of the New York Academy of Sciences, 665 (1992) 391-403 is used to purify those fractions of Protein C that are properly gamma-carboxylated. The biological activity of the fractions that are properly carboxylated and purified by the 7D7B10 monoclonal antibody described in the above reference is assessed by activated partial thromboplastin time (APTT). More than 50 μg/ml of properly carboxylated and active Protein C is detected from the milk of mice and 300 μg/ml of properly carboxylated and active Protein C is detected in the milk of pigs by the above procedure.

Example 11

Production of WAP5-9-PC Transgenic Pigs

Step 1. Pigs transgenic for WAP5-9-PC are produced essentially as described in Example 8.

Step 2. Pigs produced after embryo transfer of microinjected embryos are screened by Southern analysis. To confirm the presence of the WAP5-9-PC transgene, 10 μg of DNA isolated from tail tissue (as described for mouse tail tissue) is digested with the endonuclease Kpn I and subjected to agarose gel electrophoresis and transferred to a nylon membrane. The membrane is probed with a $^{32}$P labeled DNA fragment consisting of the 9-PC cDNA (~1.4 kbp). Hybridization is carried out at 68° C. for 4 hours using Quick Hyb (Stratagene; LaJolla, Calif.). Following standard washing methods, the membrane is subjected to autoradiography (−70° C.) for a period of 24 hours. Observance of a ~1.4 kbp band indicates the presence of the transgene.

Step 3. Transgenic pigs are matured, mated and milked as described in Example 5.

Example 12

Construction and Production of the 2.5 kbp mWAP Driven Factor10-Protein C-cDNA (WAP5-10-PC) Construct for Microinjection into Embryos to Produce Transgenic Animals The expression vector WAP5-10-PC contains coding segments of the prepropeptide of human FX linked to the mature Protein C peptide placed under expression control of the short form of the murine Whey Acidic Protein (smWAP) promoter. Specifically, The 2.5 kbp smWAP promoter described in (Van Cott et al., *Genetic Analysis*, 15 (1999) pp. 155-160) is used to direct expression of coding sequences of the Factor X propeptide linked to coding sequences for the mature Protein C peptide (Foster and Davie, PNAS, 81 (1984) pp. 4766-4770) that is followed by ~1.6 kbp of mouse Whey Acidic Protein (mWAP) 3'UTR (C. Russell, dissertation "Improvement of Expression of Recombinant Human Protein C in the Milk of Transgenic Mammal Using a Novel Transgenic Construct," Virginia Polytechnic Institute, Blacksburg, Va. (December 1993)) coding for the polyadenylation signal. Assembly of the WAP5-10-PC and its purification for microinjection is by routine recombinant DNA techniques known to the skilled artisan that can be found, for example, in Sambrook et al., MOLECULAR CLONING, A LABORATORY MANUAL, Vol. 1-3 (Cold Spring Harbor Press 1989).

Step 1. Production of the Plasmid pUCWAP5-10-PC

The hybrid protein, 10-Protein C, contains the prepropeptide of human FX linked to the mature Protein C peptide. The propeptide of Factor X is obtained by endonuclease digestion of pXKI (Example 1) with Kpn I and BssSI and gel purifying the 119 bp fragment. Then the 5' fragment of mature Protein C is obtained by PCR using primers that will introduce endonuclease sites of BssSI on the 5' end of the PCR product and EcoRI on the 3' end. PCR primers are: PCBssS1 (5'-ggtcacgagggccaactccttcctgg) and PCEcoA1 (5'-ctagaattcgatctacttggtctt) that produces a ~520 bp fragment spanning across a unique Sal I endonuclease site located ~150 bp into the mature Protein C coding sequence. After cutting with BssSI and EcoRI, this fragment along with that coding for the prepropeptide of FX is inserted (ligated) into the vector pGem7 that has been digested with Kpn I and EcoRI. Competent *E. coli* are transformed with the ligation mixture and transformants screened by blue/white selection with X-gal. White transformants are verified by digesting the corresponding plasmids with Kpn I and EcoRI and observing the 526 bp fragment after agarose gel electrophoresis. The resulting plasmid is digested with Sal I and EcoRI endonucleases and the vector fragment containing the hFX prepropeptide linked to the Protein C Sal I fragment is gel purified (FIG. 7). This fragment is then the acceptor for the Sal I to EcoRI fragment cut from pWAPPC3 (C. Russell, dissertation "Improvement of Expression of Recombinant Human Protein C in the Milk of Transgenic Mammal Using a Novel Transgenic Construct," Virginia Polytechnic Institute, Blacksburg, Va. (December 1993)) that contains the mature peptide for Protein C from the Sal I site linked through the mWAP 3'UTR to the EcoRI end. Competent *E. coli* are transformed with the ligation mixture and transformants screened by digestion with Kpn I, with observance of the ~1.4 kbp band after gel electrophoresis. The new construct coding for the hFX prepropeptide linked to Protein C is removed by Kpn I digestion and ligated into the expression cassette pUCWAP5 (Van Cott et al., *Genetic Analysis*, 15 (1999) pp. 155-160) that is digested with Kpn I and treated with CLAP (FIG. 8). Competent *E. coli* are transformed with the ligation mixture and transformants screened by PCR using the primers lmWAPfor (5'-atgcatccagacactcaga) and PCEcoA1 (5'-ctagaattcgatctacttggtctt). Observance of a ~700 bp band would indicate presence of the insert in the correct orientation. The vector with the correct insert is verified by sequence analysis and designated pUCWAP5-10-PC.

Step 2. Preparation of WAP5-10-PC DNA for Microinjection.

The DNA fragment suitable for microinjection of early stage embryos is prepared by endonuclease digestion of pUCWAP5-10-PC with the endonuclease EcoRI followed by separation from bacterial elements by agarose gel electrophoresis. The ~5.5 kbp fragment is excised from the gel and purified, followed by ethanol precipitation and suspension in TE (10 mM Tris pH 7.4, 1 mM EDTA). The fragment is further purified by subjecting the fragment to ultracentrifugation through a standard NaCl gradient. DNA concentration is determined by agarose gel electrophoresis by staining with ethidium bromide and comparing the fluorescent intensity of an aliquot of the DNA with the intensity of standards. Samples are then adjusted to 5 μg/ml.

Example 13

Production of WAP5-10-PC Transgenic Mice

Step 1. Mice, Transgenic for the Construct WAP5-10-PC are Produced Essentially as Described in Example 7.

Step 2. DNA from mice born after embryo transfer is isolated by digesting tissue in (50 mM Tris-HCl, 0.15 M NaCl, 1 M Na$_2$CO$_4$, 10 mM EDTA, 1% sodium dodecylsulfate, 1% 2-mercaptoethanol, 100 ug/ml proteinase K, pH 8.0). 750 l of lysate is extracted with 250 l chloroform/phenol (1:1) followed by precipitation with isopropanol 0.7 volumes, washed in 70% ethanol and dried. DNA is suspended in TE (10 mM Tris-HCl and 1 mM EDTA pH 8.0). Mice produced after embryo transfer of microinjected embryos are screened by Southern analysis. To confirm the presence of the WAP5-10-PC transgene, 10 μg of DNA isolated from tail tissue is digested with the endonuclease Kpn I and subjected to agarose gel electrophoresis and transferred to a nylon membrane. The membrane is probed with a $^{32}$P labeled DNA fragment consisting of the 10-PC cDNA (~1.4 kbp). Hybridization is carried out at 68° C. for 4 hours using Quick Hyb (Stratagene; LaJolla, Calif.). Following standard washing methods, the membrane is subjected to autoradiography (−70° C.) for a period of 24 hours. Observance of a ~1.4 kbp band indicates the presence of the transgene.

Example 14

Production of WAP5-10-PC Transgenic Pigs

Step 1. Pigs transgenic for WAP5-10-PC are produced essentially as described in Example 8.

Step 2. Pigs produced after embryo transfer of microinjected embryos are screened by Southern analysis. To confirm the presence of the WAP5-10-PC transgene, 10 μg of DNA isolated from tail tissue (as described above for mouse tail tissue) is digested with the endonuclease Kpn I and subjected to agarose gel electrophoresis and transferred to a nylon membrane. The membrane is probed with a $^{32}$P labeled DNA fragment consisting of the 10-PC cDNA (~1.4 kbp). Hybridization is carried out at 68° C. for 4 hours using Quick Hyb (Stratagene; LaJolla, Calif.). Following standard washing methods, the membrane is subjected to autoradiography (−70° C.) for a period of 24 hours. Observance of a ~1.4 kbp band indicates the presence of the transgene.

Example 15

Construction and Production of the 2.5 kbp mWAP Driven Factor 7-Protein C-cDNA (WAP5-7-PC) Construct for Microinjection into Embryos to Produce Transgenic Animals The expression vector WAP5-7-PC contains coding segments of the prepropeptide of human FVII linked to the mature Protein C peptide placed under expression control of the short form of the murine Whey Acidic Protein (smWAP) promoter. Specifically, The 2.5 kbp smWAP promoter described in (Van Cott et al., *Genetic Analysis*, 15 (1999) pp. 155-160) is used to direct expression of coding sequences of the Factor VII propeptide (Hagen et al., *PNAS*, 83 (8), (1986) pp. 2412-2416) linked to coding sequences for the mature Protein C peptide (Foster and Davie, PNAS, 81 (1984) pp. 4766-4770) that is followed by ~1.6 kbp of mouse Whey Acidic Protein (mWAP) 3'UTR (C. Russell, dissertation "Improvement of Expression of Recombinant Human Protein C in the Milk of Transgenic Mammal Using a Novel Transgenic Construct," Virginia Polytechnic Institute, Blacksburg, Va. (December 1993)) coding for the polyadenylation signal. Assembly of the WAP5-7-PC and its purification for microinjection is by routine recombinant DNA techniques known to the skilled artisan that can be found, for example, in Sambrook et al., MOLECULAR CLONING, A LABORATORY MANUAL, Vol. 1-3 (Cold Spring Harbor Press 1989).

Step 1. Production of the Plasmid pUCWAP5-7-PC

The hybrid protein, 7-Protein C contains the prepropeptide of human FVII linked to the mature Protein C peptide. The propeptide of Factor VII is obtained by PCR of the Factor VII cDNA plasmid referred in (Hagen et al., *PNAS*, 83 (8), (1986) pp. 2412-2416) from the ATG start sequence to the Asc I site in the Factor VII cDNA. PCR primers are: KpnFVIIs1, 5'-tcaccatggtctcccaggccctcag) that introduces a unique Kpn I on the 5' end of the fragment and AscFVII A1, 5'-ttggcgcgc-cggcgccggtgc). The 180 bp PCR product is then digested with the endonucleases Kpn I and Asc I. Then the 5' fragment of mature Protein C is obtained by PCR using primers that introduce endonuclease sites of Asc I on the 5' end of the PCR product and EcoRI on the 3' end. PCR primers are: PCAscS1 (5'-gcgccggcgcgccaactccttcctgg) and PCEcoA1 (5'-ctagaat-tcgatctacttggtctt) that would produce a ~520 bp fragment spanning across a unique Sal I endonuclease site located ~150 bp into the mature Protein C coding sequence. After cutting with Asc I and EcoRI, this fragment along with that coding for the prepropeptide of FVII can be inserted (ligated) into the vector pGem7 that has been digested with Kpn I and EcoRI (FIG. 9). Competent *E. coli* are transformed with the ligation mixture and transformants screened by blue/white selection with X-gal. White transformants are verified by digesting the corresponding plasmids with Kpn I and EcoRI and observing the ~520 bp fragment after agarose gel electrophoresis. The resulting plasmid is digested with Sal I and EcoRI endonucleases and the vector fragment containing the hFVII prepropeptide linked to the Protein C Sal I fragment is gel purified. This fragment is then the acceptor for the Sal I to EcoRI fragment cut from pWAPPC3 (C. Russell, dissertation "Improvement of Expression of Recombinant Human Protein C in the Milk of Transgenic Mammal Using a Novel Transgenic Construct," Virginia Polytechnic Institute, Blacksburg, Va. (December 1993)) that contains the mature peptide for Protein C from the Sal I site linked through the mWAP 3'UTR to the EcoRI end. Competent *E. coli* can be transformed with the ligation mixture and transformants screened by digestion with Kpn I, with observance of the ~1.4 kbp band after gel electrophoresis. The new construct coding for the hFVII prepropeptide linked to the mature Protein C peptide is removed by Kpn I digestion and ligated into the expression cassette pUCWAP5 that is digested with Kpn I and treated with CIAP (FIG. 10). Competent *E. coli* are transformed with the ligation mixture and transformants screened by PCR using the primers lmWAP for (5'-atgcatccagacactcaga) and PCEcoA1 (5'-ctagaattcgatctacttggtctt). Observance of a ~700 bp band indicates the presence of the insert in the correct orientation. The vector with the correct insert is verified by DNA sequence analysis and designated pUCWAP5-7-PC.

Step 22. Preparation of WAP5-7-PC DNA for Microinjection.

The DNA fragment suitable for microinjection of early stage embryos is prepared by endonuclease digestion of pUCWAP5-7-PC with the endonuclease EcoRI followed by separation from bacterial elements by agarose gel electrophoresis. The ~5.5 kbp fragment is excised from the gel and purified, followed by ethanol precipitation and suspension in TE (10 mM Tris pH 7.4, 1 mM EDTA). The fragment is further purified by subjecting the fragment to ultracentrifugation through a standard NaCl gradient. DNA concentration is determined by agarose gel electrophoresis by staining with ethidium bromide and comparing the fluorescent intensity of an aliquot of the DNA with the intensity of standards. Samples are then adjusted to 5 μg/ml.

Example 16

Production of WAP5-7-PC Transgenic Mice

Step 1. Mice, transgenic for the construct WAP5-7-PC are produced essentially as described in Example 7.

Step 2. DNA from mice born after embryo transfer is isolated by digesting tissue in (50 mM Tris-HCl, 0.15 M NaCl, 1 M Na$_2$ClO$_4$, 110 mM EDTA, 1% sodium dodecyl-sulfate, 1% 2-mercaptoethanol, 100 ug/ml proteinase K, pH 8.0). 750 l of lysate is extracted with 250 l chloroform/phenol (1:1) followed by precipitation with isopropanol 0.7 volumes, washed in 70% ethanol and dried. DNA is suspended in TE (10 mM Tris-HCl and 1 mM EDTA pH 8.0). Mice produced after embryo transfer of microinjected embryos are screened by Southern analysis. To confirm the presence of the WAP5-

7-PC transgene, 10 μg of DNA isolated from tail tissue is digested with the endonuclease Kpn I and subjected to agarose gel electrophoresis and transferred to a nylon membrane. The membrane is probed with a $^{32}$P labeled DNA fragment consisting of the 7-PC cDNA (~1.4 kbp). Hybridization is carried out at 68° C. for 4 hours using Quick Hyb (Stratagene; LaJolla, Calif.). Following standard washing methods, the membrane is subjected to autoradiography (−70° C.) for a period of 24 hours. Observance of a ~1.4 kbp band indicates the presence of the transgene.

Example 17

Production of WAP5-7-PC Transgenic Pigs

Step 1. Pigs transgenic for WAP5-7-PC are produced essentially as described in Example 8.

Step 2. Pigs produced after embryo transfer of microinjected embryos are screened by Southern analysis. To confirm the presence of the WAP5-7-PC transgene, 10 μg of DNA isolated from tail tissue (prepared as described above for mouse tail tissue) is digested with the endonuclease Kpn I and subjected to agarose gel electrophoresis and transferred to a nylon membrane. The membrane is probed with a $^{32}$P labeled DNA fragment consisting of the 7-PC cDNA (~1.4 kbp). Hybridization is carried out at 68° C. for 4 hours using Quick Hyb (Stratagene; LaJolla, Calif.). Following standard washing methods, the membrane is subjected to autoradiography (−70° C.) for a period of 24 hours. Observance of a −1.4 kbp band indicates the presence of the transgene.

Multi Gene System

The following Examples describe the design and production of the multi gene expression system for directing production of proteins. Generally, the system has two functional parts, the first DNA sequence uses a tissue specific promoter to direct expression of a modified transactivation factor inside the cell. This is referred to as a Type A gene or Type A sequence. This modified transactivation factor has been changed from its naturally occurring form by removing its DNA binding domain and inserting in its place the DNA binding domain of the yeast GAL-4 transcription factor. This gives the modified transactivation factor specificity for GAL-4 DNA binding sites. In the multi gene system the modified transactivation factor will bind repetitive GAL-4 recognition sequences that are upstream of the minimum promoter of the second gene. This second gene, containing the minimum promoter, is referred to as a Type B gene or Type B sequence. The Type B gene is described as having a promoter made up of GAL-4 binding sites placed before the eukaryotic polymerase "TATA box" recognition site used to express a gene of interest when activated by the modified transactivation factor produced by the Type A gene. Flanking the protein coding regions in Type A and B genes is a sequence corresponding to the murine WAP 3' untranslated region coding for the polyadenylation signal as described in Example 1.

Example 18

Construction and Preparation of Long Mouse WAPStat (LMWStat—a Type A Gene) for Microinjection into Embryos to Produce Transgenic Animals Generally, for constructing the LMWStat expression construct several sub cloning steps are involved including the assembly of plasmids to facilitate the removal of the endogenous DNA binding domain and its replacement with the Gal-4 binding domain. Assembly of the LMWStat and its purification for microinjection is by routine recombinant DNA techniques known to the skilled artisan that can be found, for example, in Sambrook et al., MOLECULAR CLONING, A LABORATORY MANUAL, Vol. 1-3 (Cold Spring Harbor Press 1989).

Step 1. Production of the Plasmid pUC8-3' UTR.

The plasmid pUC8-3' UTR, used as an intermediate plasmid for the assembly of elements of the modified Stat gene, was assembled in three phases (FIG. 11). The plasmid pUC18 (Invitrogen; Carlsbad, Calif.) was digested with the endonucleases Nde I and Kpn I and subjected to gel electrophoresis. The fragment containing the ampicillin resistance gene was extracted from the gel and ligated with 2 sets of synthetic adapters. Adapter 1 contained Nde I and Not I ends as recognized by those enzymes and adapter 2 contained Not I and Kpn I ends. Sequences for oligos used in making adapter 1 are: NdeNotS, 5'-tatgagggcgcgccagattaattaa 3' and NdeNotA 5-ggccgcgattaattaatgtggcgcg 3', adapter 2 sequences are Not-KpnS 5'-ggccgccacgacttcgggtac-3' and NotKpnA 5'-ccgaagtcgtggc-3'. Oligos were boiled for 5 minutes and allowed to cool to RT. Successful ligation of both sets of linkers and the vector produced the plasmid pUC8bc. The second phase consisted of cutting the pUC8bc vector with the endonucleases Kpn I and Afl III and purifying the fragment containing the ampicillin resistance gene. Into this was inserted (ligated) the KpnI-Afl III 3' UTR mouse WAP fragment from the plasmid pUCWAP6 in (S. Butler, thesis "Production and Secretion of Recombinant Human Fibrinogen by the Transgenic Murine Mammary Gland", Virginia Polytechnic Institute, Blacksburg, Va. (May, 1997)) to produce the vector pUC8-3'UTR-AflIII. Phase three consisted of modifying the remainder of the mouse WAP 3'UTR 207 bp (Afl III to Not I) and inserting it into the Afl III site of pUC8-3'UTR-Afl III. The Afl III-Not 13'UTR fragment of pUCWAP6 was ligated with linkers to disrupt the Not I site and introduce a Sbf I site followed by an Afl III site on the end. Oligo sequences used to make the linkers are as follows: NotXAflS 5'ggccagcctgcaggttga and NotXAflA1 5'-catgtcaacctgcaggct-3'. This ligation thus produced a fragment that could be ligated into the Afl III site in pUC8-3'UTR-Afl III. The orientation of the fragment was checked by endonuclease digestion with Sib I and Spe I, with the correct orientation indicated by the presence of three bands in the sizes of 2.7 kbp, 740 bp and 270 bp after gel electrophoresis.

Step 2. Production of the Gal-4 Binding Domain and Carrier Plasmid.

The Gal-4 DNA Binding Domain (DBD) was obtained through polymerase chain reaction amplification of genomic *Saccharomyces cerevisiae* DNA. The 555 bp fragment was produced using the primers GALDBDS1 (5'-tccca-gattttcagcttca) and GALDBDA1 (5'-atcatgatgagctgccgagt). The PCR fragment was gel purified and inserted into pCR4 to generate the plasmid pCR4Gal-4 (FIG. 12).

Step 3. Production of the Plasmid pStatdeltaDBD.

The plasmid pStatdeltaDBD containing sequences coding for mouse Stat 5a (Stat), where the DNA binding domain was removed and replaced with the Gal-4 DBD, was assembled in three phases. The first phase consisted of using PCR to generate Stat in two fragments (5' and 3') there by omitting the DBD. The template used for PCR was I.M.A.G.E. Consortium clone 3482404, library NCICGAPMam5 from Research Genetics (Huntsville, Ala.). PCR primers were StatPacS1 (5' gcgttaattaatggcgggctggattcaggc) and SStatrev (5'aaatatcgcat-gcttgttcgataga) to put Pac I and Sph I endonuclease recognition sites on the ends on the 5' fragment of 1395 bp. The PCR product was cloned into pCR4. PCR primers were 3StatFor (5'-caagcatgcctggaacagcattgttaacagcgctcaacatgaaattc) and StatNotA2 (5'acggcggccgctcaggacagggagcttctag) to put Sph I and Not I endonuclease recognition sites on the ends of the Stat 3' fragment of 876 bp. The PCR product was cloned into pCR4. The second phase was to put the two fragments together in one vector (FIG. 13). The vector pUC8 3' was digested with Pac I and Not I, gel purified and ligated with the two Stat fragments that were cut out with their corresponding endonucleases (5'Stat, Pac I and Sph 1 and 3'Stat, Sph I and Not I) and gel purified. The ligation mix was then used to transform competent E. coli cells with plasmids from corresponding transformants screened by endonuclease digestion with Pac I and Not I and confirmed by visualizing a ~2.2 kbp band. The modified pUC8 Stat 3' containing the Stat elements was named pStat(-DBD) (FIG. 13). The third phase consisted of inserting the Gal-4 DNA binding domain in between the Stat 5' and Stat 3' elements of pStat(-DBD) to produce pStat-deltaDBD (FIG. 14). The plasmid pStatdeltaDBD was produced by cutting the plasmid pStat(-DBD) with the endonucleases Sph I and Hpa I, and inserting the gel purified Gal-4 DNA binding domain that was removed from pCR4Gal-4 by Sph I and Hpa I digestion. The ligation mixture was used to transform competent E. coli cells and transformants were screened. Colonies of transformed E. coli were screen by digestion of corresponding plasmids with SphI and Hpa I and observing the ~250 bp fragment after agarose gel electrophoresis. After addition of the Gal-4 binding domain the modified Stat coding region is 2.4 kbp.

Step 4. Production of the Plasmid pMCS-Stat

The vector pMCS-Stat was produced to facilitate the insertion of the long mouse Whey Acidic Promoter (lmWAP) (Paleyanda et al., Transgene Res., 3 (1994) pp. 335-343) and short mouse Whey Acidic Promoter (smWAP) (Van Cott et al., *Genetic Analysis*, 15 (1999) pp. 155-160) in front of the DNA coding segment of pUC8-3'Stat. By digesting this plasmid with Pspom I (lmWAP) or EcoRI (smWAP) then with Sun I, the corresponding promoter can be inserted before the coding region. The vector was produced by digesting the plasmid pUC8-3'Stat with the endonucleases Asc I and Pac I, followed by gel purification. This fragment was then ligated with a fragment of DNA (referred to as MCS) containing internal endonuclease sites for EcoRI, Pspom I and Sun I along with compatible Asc I and Pac I ends (FIG. 15). The MCS fragment was produced by boiling two synthetic oligos (ProadapS, 5'cgcgcctcgtgaattccactgggccct-tatcgcagtcgtacgaacgttaat3' and ProadapA, 5'taacgttcgtac-gactgcgataagggcccagtggaattcacgagg3') and allowing them to cool to room temperature. The ligation mixture was used to transform competent E. coli cells with resulting transformants screened by digesting their corresponding plasmids with EcoRI and observing the presence of a linearized plasmid band (6.3 kbp) after agarose gel electrophoresis.

Step 5. Production of the Plasmid pLMWStat

The vector LMWStat containing elements of the long mouse Whey Acidic Protein (lmWAP) promoter defined above, used to express the engineered protein StatdeltaDBD, was produced by inserting the promoter for long mouse WAP in front of the coding DNA for StatdeltaDBD (FIG. 16). Specifically, pMCS-Stat was digested with the endonucleases Pspom I and Sun I, gel purified and ligated with the Not I and Acc65I digested lmWAP promoter. The overhanging ends Pspom I-Not I and Sun I-Acc65I are compatible. The Not I-Acc65I lmWAP promoter was obtained from digestion of the plasmid pUCWAP6 (S. Butler, thesis "Production and Secretion of Recombinant Human Fibrinogen by the Transgenic Murine Mammary Gland", Virginia Polytechnic Institute, Blacksburg, Va. (May, 1997)) with endonucleases Not I and Acc65I followed by the gel purification of the 4.1 kbp promoter. Ligation mixture was used to transform competent E. coli cells with resulting transformants screened by digesting their corresponding plasmids with EcoRI and Pac I and observing the presence of a 4.1 kbp promoter band after agarose gel electrophoresis. The plasmid with the 4.1 lmWAP insert was verified by DNA sequence analysis and designated pLMWStat.

Step 6. Preparation of LMWStat DNA for Microinjection.

The construct LMWStat is obtained for microinjection by its removal from pLMWStat with Not I and partial Sbf I digestion followed by separation from bacterial elements by agarose gel electrophoresis. The ~8.1 kbp fragment is excised from the gel and purified by using a gel extraction kit (Ultra-Clean 15, MoBio Labs, Solana Beach, Calif.) followed by ethanol precipitation and suspension in TE (10 mM Tris pH 7.4, 1 mM EDTA). The fragment is further purified by subjecting the fragment to ultracentrifugation through a standard NaCl gradient. DNA concentration is determined by agarose gel electrophoresis by staining with ethidium bromide and comparing the fluorescent intensity of an aliquot of the DNA with the intensity of standards. Samples were then adjusted to 5 µg/ml.

Example 19

Construction and Preparation of Short Mouse WAPStat (SMWStat—an Alternative Type A Gene of the Multi Gene System) for Microinjection into Embryos to Produce Transgenic Animals Step 1. Production of the Plasmid pSMWStat.

Assembly of SMWStat and its purification for microinjection is by routine recombinant DNA techniques known to the skilled artisan that can be found, for example, in Sambrook et al., MOLECULAR CLONING, A LABORATORY MANUAL, Vol. 1-3 (Cold Spring Harbor Press 1989).

The construct SMWStat containing elements of the short mouse Whey Acidic Protein (smWAP) promoter (Van Cott et al., *Genetic Analysis*, 15 (1999) pp. 155-160)) to express the engineered protein StatdeltaDBD was produced by inserting the promoter for short mouse WAP in front of the coding DNA for StatdeltaDBD (FIG. 17). Specifically, pMCS-Stat (described in Example 16) was digested with the endonucleases EcoRI and Sun I, gel purified and ligated with the EcoRI-Acc65I smWAP promoter. The overhanging ends Sun I and Acc65I are compatible. The EcoRI-Acc65I smWAP promoter was obtained from digestion of the plasmid pUCWAP5FIX (Van Cott et al., *Genetic Analysis*, 15 (1999) pp. 155-160)) with endonucleases EcoRI and Acc65I followed by the gel extraction and purification of the 2.5 kbp mWAP promoter. Ligation mixture was used to transform competent E. coli cells with resulting transformants screened by digesting their corresponding plasmids with EcoRI and Pac I and observing the presence of a 2.5 kbp promoter band after agarose gel electrophoresis. Plasmids with the correct insert were verified by DNA sequence analysis and identified as pSMWStat.

Step 2. The construct SMWStat is obtained for microinjection by its removal from pSMWStat with EcoRI and Sbf I digestion followed by separation from bacterial elements by agarose gel electrophoresis. The ~6.5 kbp fragment is excised from the gel and purified by using a gel extraction kit (Ultra-Clean 15, MoBio Labs, Solana Beach, Calif.) followed by ethanol precipitation and suspension in TE (10 mM Tris pH 7.4, 1 mM EDTA). The fragment is further purified by subjecting the fragment to ultracentrifugation through a standard NaCl gradient. DNA concentration is determined by agarose gel electrophoresis by staining with ethidium bromide and comparing the fluorescent intensity of an aliquot of the DNA with the intensity of standards. Samples were then adjusted to 5 µg/ml.

Example 20

Construction and Preparation of WAP6GR (an Alternative Type A Gene of the Multi Gene System) for Microinjection into Embryos to Make Transgenic Animals The WAP6GR construct uses the regulator elements of the mouse WAP gene to express coding sequences of a modified glucocorticoid receptor (GR) that has had its DNA binding domain removed and replaced with that of Gal-4. Specifically, The 4.1 kbp lmWAP promoter described in (Paleyanda et al., Transgene Res., 3 (1994) pp. 335-343) is used to direct expression of coding sequences of the modified GR that is followed by ~1.6 kbp of mouse Whey Acidic Protein (mWAP) 3'UTR (C. Russell, dissertation "Improvement of Expression of Recombinant Human Protein C in the Milk of Transgenic Mammal Using a Novel Transgenic Construct," Virginia Polytechnic Institute, Blacksburg, Va. (December 1993)) coding for the polyadenylation signal. Assembly of the WAP6GR and its purification for microinjection is by routine recombinant DNA techniques known to the skilled artisan that can be found, for example, in Sambrook et al., MOLECULAR CLONING, A LABORATORY MANUAL, Vol. 1-3 (Cold Spring Harbor Press 1989).

Step 1. Production of the Plasmid pGem(Eco-)GR

The vector pGR was produced by inserting the cDNA of GR into the BamHI site of the vector pGEM7 FIG. 18). The cDNA segment was produced using Reverse Transcriptase Polymerase Chain Reaction (RT-PCR) of total mouse mammary gland RNA where the primers were used to introduce BamHI sites at both ends of the cDNA. The conditions for RT-PCR were 50° C. for 30 min, then 94° C. for 2 min followed by 35 cycles of 94° C. for 15 sec, 56° C. for 30 sec, 72° C. for 2 min followed by 72° C. for 10 min. Both the vector and RT-PCR product were digested with BamHI and ligated together. The ligation mixture was used to transform competent *E. coli* cells with resulting transformants screened by blue/white selection on X-Gal plates. White colonies were further screened by digesting their corresponding plasmids with BamHI and observing the presence of a 1.6 kbp band after agarose gel electrophoresis. The strategy for changing the DNA binding domain for GR involved its removal by Xcm I and EcoRI endonucleases, inserting a linker containing SphI and Hpa I endonuclease sites then inserting in the Gal-4 DNA binding domain. However, the vector pGEM contained an EcoRI site and this needed to be removed before the DNA binding domain could be changed. Therefore, pGEM7 was modified by digesting the vector with Aat II and Sma I, filling in the overhanging ends with Klenow fragment polymerase and ligating the blunt ends together. Ligation mixture was used to transform competent *E. coli* cells with resulting transformants screened by blue/white color selection of X-gal plates. Plasmids from white colonies were then isolated and subjected to digestion with EcoRI to verify removal of the site. The plasmid missing the EcoRI site was designated pGEM(Eco-). The plasmid pGEM(Eco-)GR used to switch out the DNA binding domain was produced by digesting pGEM(Eco-) with BamHI, dephosphorylating using CLAP and ligating with the GR insert of pGR that was removed by BamHI digestion and gel purified. Ligation mixture was used to transform competent *E. coli* cells with resulting transformants screened by PCR using the primers GRS1 and GRA1. Colonies positive for the ~1.6 kbp PCR band were verified by digesting their corresponding plasmids with BamHI and observing a ~1.6 kbp band after agarose gel electrophoresis.

Step 2: Upon sequencing the GR insert of pGEM(Eco-)GR a mutation at 422 bp downstream of the start codon was found, where Asn was changed to Ser (AAT->AGT). This was changed to the sequence found in Genebank (assession# X04435) by digesting pGEM(Eco-)GR with the endonucleases Sal I and Sfi I, gel purified and ligating in a set of oligos. Oligos were: GrmendS, 5ptggcctccctctggggaaaca-gactttcggcttctggaagaaagcattgcaaacctcaatagg-3' and GrmendA 5'-ptcgacctattgaggtttgcaat-gctttcttccagaagccgaaagtcttgtttccccagaggagaggccaagc-3'. The plasmid with the corrected mutation pGEM(Eco-)GRdeltaMut was screened for by digesting with endonuclease Dde I as the corrected plasmid loses this endonuclease site after repair.

Step 3: Production of the Plasmid pGRdeltaDBD

The DNA binding domain of GR was replaced with that of Gal-4 by first removing the GR DNA binding domain from pGEM(Eco-)GRdeltaMut with the endonucleases Xcm I and EcoRI then ligating in a DNA linker (GRDBD) that contained endonuclease sites for Sph I and Hpa I. The linker GRDBD was produced from two oligos GradaptS (5-p-gcatgcgattat-gccagcattgttaacaaagaagaaaataaaagg) and GRDBDA1 (5'-p-aattccttttattttcttctttgttaacaatgctggcataatcgcatgcg) that were boiled for 5 min and allowed cool to room temperature. Ligation mixture was used to transform competent *E. coli* cells with resulting transformants screened by digesting their corresponding plasmids with Hpa I, where linearization of the vector indicated presence of insert. The vector containing the insert pGEM(Eco-)GR(-DBD) was cut with the endonucleases Hpa I and Sph I, gel purified and ligated with the Gal-4 DNA binding domain cut out of pCR4Gal-4 with Hpa I and Sph I and gel purified (FIG. 19). The ligation mixture was used to transform competent *E. coli* cells and transformants were screened. Colonies of transformed *E. coli* were screen by digesting their corresponding plasmids with Sph I and Hpa I and observing a ~550 bp band after gel electrophoresis. The plasmid containing the Gal-4 DNA binding domain inserted in the GR with the mutation corrected was named pGRdeltaDBD.

Step 4. Production of the Plasmid pGRdeltaDBD2

The plasmid pGRdelta DBD2 was produced to facilitate cloning of the GRdeltaDBD into the pUCWAP6 plasmid. The pUCWAP6 plasmid has a BamHI endonuclease site located in the mouse WAP 3'UTR, therefore the BamHI sites located on the ends of GRdeltaDBD needed to be changed to Acc65 I recognition sites. This was accomplished by digesting pGEM7 with the endonucleases Kpn I and BamHI and ligating in a set of oligos that contained a unique BamHI site surrounded by two Acc65 I recognition sites, thus providing an unique BamHI site to put in the GRdeltaDBD fragment and allowing its removal with Acc65 I digestion. Oligos used are Kpn-Bamsense (5'-ctcaggatcctaaggtaccctt) and Kpn-Bamantisense (5'-gatcaagggtaccttaggatcctgaggtac) which were boiled for 5 min and cooled to room temperature. These oligos were then ligated with pGEM7 that was cut with the endonucleases KpnI and BamHI and gel purified (FIG. 20). The ligation mixture was used to transform competent *E. coli* cells and transformants were screened. Colonies of transformed *E. coli* were screened by digesting their corresponding plasmids with Hind III and observing non-linearized vector after gel electrophoresis. This modified plasmid pGEMKBK was then digested with BamHI endonuclease, dephosphorylated with CIAP then gel purified and ligated with the GRdeltaDBD fragment isolated by digesting pGRdeltaDBD with BamHI and gel purifying. The ligation mixture was used to transform competent E. coli cells and transformants were screened. Colonies of transformed E. coli were screened by digestion of their corresponding plasmids with endonuclease Kpn I followed by observing the presence of a 1.6 kbp band after agarose gel electrophoresis.

Step 5. Production of pUCWAP6GR

The vector WAP6GR containing elements of the long mouse Whey Acidic Protein (lmWAP) promoter (described above) used to express the engineered GR-deltaDBD was produced from the plasmid pUCWAP6GR (FIG. 21). The plasmid pUCWAP6GR was assembled by digesting pUCWAP6 (described above) with the endonuclease Acc65I and dephosphorylated using CIAP followed by gel purification. This vector was then ligated with the coding region of GRdeltaDBD that was removed from pGR-deltaDBD2 by digest with Acc65I and gel purified. The ligation mixture was used to transform competent E. coli cells and transformants were screened. Colonies of transformed E. coli were screened by polymerase chain reaction for the presence of the vector and the insert in the correct orientation by using the following primers: lmWAP for, 5' atgcatcccagacactcaga and WAPGR-rev, 5'acagtgaaacggctttggat under the following conditions: 95° C. for 2 min then 40 cycles of annealing 55° C. for 30 sec, denaturation 95° C. for 30 sec and elongation 72° C. for 45 sec. Presence of a 348 bp band indicated correct orientation and vector. Final verification is by DNA sequence analysis.

Step 6. Production of WAP6GR DNA for Microinjection

The DNA fragment suitable for microinjection of early stage embryos is prepared by endonuclease digestion of pUCWAP6GR with the enzyme Not I followed by separation from bacterial elements by agarose gel electrophoresis. The ~7.4 kbp fragment is excised from the gel and purified by using a gel extraction kit (UltraClean 15, MoBio Labs, Solana Beach, Calif.) followed by chloroform/phenol extraction, ethanol precipitation and suspension in TE (10 mM Tris pH 7.4, 1 mM EDTA). The fragment is further purified by subjecting it to ultracentrifugation through a standard NaCl gradient. DNA concentration is determined by agarose gel electrophoresis by staining with ethidium bromide and comparing the fluorescent intensity of an aliquot of the DNA with the intensity of standards. Samples were then adjusted to 5 µg/ml.

Example 21

Construction and Preparation of Minimum Promoter —XKI Hybrid cDNA (MPXKI, Type B Gene of the Multi Gene System) for Microinjection with a Type A Gene into Embryos to Make Transgenic Animals The type B gene of the multi gene system, described as having a promoter made up of GAL-4 binding sites upstream of the eukaryotic polymerase "TATA" recognition site, is used to express a gene of interest when activated by the transactivation factor produced by a Type A gene. Flanking the coding region in the type B gene is the murine WAP 3' untranslated region (3'UTR) coding for the polyadenylation signal (C. Russell, dissertation "Improvement of Expression of Recombinant Human Protein C in the Milk of Transgenic Mammal Using a Novel Transgenic Construct," Virginia Polytechnic Institute, Blacksburg, Va. (December 1993))I. The core Type B gene has been designed to accept the coding region of any desired protein by cloning into either a unique Kpn I or Not I endonuclease site located between the minimum promoter and the 3' UTR.

Step 1. The minimum promoter cassette (MPC) was produced by digesting the plasmid pUC 8 3' with the endonucleases Asc I and Pac I followed by gel purification of the cut vector, then ligation with two sets of oligo fragments that correspond to the GAL-4 minimum promoter (Min 1 and Min 2) (FIG. 24). Promoter fragments were produced by boiling two sets of oligos (Min1S and Min1A) and (Min2S and Min2A) for 5 minutes then allowed to slowly cool to room temperature. Sequence of oligos are as follows: Min1S, 5'p-cgcgccggagtactgtcctccgagtg-gagtacttgtcctccgagcggagtactgtcctccgagtcgagggtcgaagcgga; Min 1A, 5'-agtactccgcttcgaccctcgactcg-gaggacagtactccgctcggaggacagtactccactcggaggacagtactccgg; Min2S, 5'p-gtactgtccgagtggagtactgtcctc-cgagcggagtactgtcctccgagtcgactctagagggtatataattaat; Min2A, 5' taattatataccctctagagtcgactcg-gaggacagtactccgctcggaggacagtactccactcggac. The ligation mixture was used to transform competent E. coli cells and transformants were screened. Colonies of transformed E. coli were screened by digesting their corresponding plasmids with Sal I endonuclease, where linearization of the vector indicated incorporation of the promoter fragments. The plasmid containing the correct insert was verified by DNA sequence analysis and designated pMPC.

Step 2. The minimum promoter-XKI plasmid was produce by digesting the plasmid pMPC with the endonuclease Kpn I followed by ligation with the coding segment of pUCWAP6XKI (Example 1) (FIG. 25). The coding segment of pUCWAP6XKI was obtained by digesting the pUCWAP6XKI vector with Kpn I followed by gel purification of the 786 bp fragment. Colonies of transformed E. coli were screened by polymerase chain reaction for the presence of the vector and the insert in the correct orientation by using the following primers: MinFor, 5'ggtcgaagcggagtactgtc3' and minXKIrev, 5'-ttcattcgtcttgtcgctgt-3' under the following conditions: 95° C. for 2 min then 40 cycles of annealing 55° C. for 30 sec, denaturation 95° C. for 30 sec and elongation 72° C. for 45 sec. Presence of a 356 bp band indicated correct orientation of insert. The plasmid containing the correct insert was verified by DNA sequence analysis and designated pMPXKI.

Step 3. The DNA fragment suitable for microinjection of early stage embryos is prepared by endonuclease digestion of pMPXKI with the endonucleases Asc I and Sbf I followed by separation from bacterial elements by agarose gel electrophoresis. The ~4.7 kbp fragment is excised from the gel and purified, followed by ethanol precipitation and suspension in TE (10 mM Tris pH 7.4, 1 mM EDTA). The fragment is further purified by subjecting the fragment to ultracentrifugation through a standard NaCl gradient. DNA concentration is determined by agarose gel electrophoresis by staining with ethidium bromide and comparing the fluorescent intensity of an aliquot of the DNA with the intensity of standards. Samples are then adjusted to 5 µg/ml.

Example 22

Production of Transgenic Mice that Express the Factor XKI cDNA using the Multi Gene System with LMWStat and MPXKI DNA Sequences Step 1. Transgenic mice are produced essentially as described by Hogan et al., *Manipulating the Mouse Embryo*, Cold Spring Harbor Press, (1986), which is hereby incorporated by reference. That is, glass needles for microinjection are prepared using a micropipet puller and microforge. Injections are performed using a Nikon microscope having Hoffman Modulation Contrast optics, with Narashigi micromanipulators and a pico-injector driven by $N_2$ (Narishige). Fertilized mouse embryos are surgically removed from oviducts of superovulated female CD-1 mice and placed into M2 medium. Cumulus cells are removed from the embryos with hyaluronidase at 300 µg/ml. The embryos are then rinsed in new M2 medium and stored at 37 degrees centigrade prior to injection. Stock solutions containing about 5 µg/ml of the above described DNA are mixed in an equal volume ratio and microinjected into the mouse embryos. After microinjection, embryos are implanted into avertin-anesthetized CD-1 recipient females made pseudo-pregnant by mating with vasectomized males. About 25-30 microinjected mouse embryos per recipient are transferred into pseudopregnant females.

Step 2. Mice produced after embryo transfer of microinjected embryos are screened by Southern analysis. Screening for the lmWAPStat construct: 10 mg of DNA isolated from tail tissue (as described in Example 5) is digested with the endonucleases Pac I and Not I and subjected to agarose gel electrophoresis and transferred to a nylon membrane. The membrane is probed with a $^{32}P$ labeled DNA fragment of lmWAPStat consisting of the Pac I to Not I (~2.4 kbp) cDNA fragment. Hybridization is carried out at 68° C. for 4 hours using Quick Hyb (Stratagene; LaJolla, Calif.). Following standard washing methods, the membrane is subjected to autoradiography (–70° C.) for a period of 24 hours. Transgenic mice carrying the Stat gene are identified by the presence of a ~2.4 kbp size band. Screening for the MPXKI construct: 10 mg of DNA isolated from tail tissue is digested with the endonuclease Kpn I and subjected to agarose gel electrophoresis and transferred to a nylon membrane. The membrane is probed with a $^{32}P$ labeled DNA fragment of MPXKI consisting of the Kpn I (~0.8 kbp) cDNA fragment. Hybridization is carried out at 6° C. for 4 hours using Quick Hyb (Stratagene; LaJolla, Calif.). Following standard washing methods, the membrane is subjected to autoradiography (–70° C.) for a period of 24 hours. Transgenic mice carrying the Stat gene are identified by the presence of a ~0.8 kbp size band.

Example 23

Production of Transgenic Pigs that Express the XKI cDNA Using the Multi Gene System with LMWStat and MPXKI DNA Sequences Step 1. Pig embryos are recovered from the oviduct, and placed into a 1.5 ml microcentrifuge tube containing approximately 0.5 ml embryo transfer media (Beltsville Embryo Culture Medium). Embryos are centrifuged for 12 minutes at 16,000×g RCF (13,450 RPM) in a microcentrifuge (Hermle, model Z231). The embryos are then removed from the microcentrifuge tube with a drawn and polished Pasteur pipette and placed into a 35 mm petri dish for examination. Embryos are then placed into a microdrop of media (approximately 100 µl) in the center of the lid of a 100 mm petri dish, and silicone oil is used to cover the microdrop and fill the lid to prevent media from evaporating. The petri dish lid containing the embryos is set onto an inverted microscope (Carl Zeiss) equipped with both a heated stage and Hoffman Modulation Contrast optics (200× final magnification). A finely drawn (Kopf Vertical Pipette Puller, model 720) and polished (Narishige microforge, model MF-35) micropipette is used to stabilize the embryos while about 1-2 picoliters of stock solutions containing about 5 µg/ml of the above described DNA are mixed in an equal volume ratio and microinjected into the non-pronuclear stage pig embryos using another finely drawn micropipette. Embryos surviving the microinjection process as judged by morphological observation are loaded into a polypropylene tube (2 mm ID) for transfer into the recipient pig. About 40-50 microinjected embryos are transferred into each hormonally synchronized surrogate mother recipient female pig.

Step 2. Pigs produced after embryo transfer of microinjected embryos are screened by Southern analysis. Screening for the lmWAPStat construct: 10 mg of DNA isolated from tail tissue is digested with the endonucleases Pac I and Not I and subjected to agarose gel electrophoresis and transferred to a nylon membrane. The membrane is probed with a $^{32}P$ labeled DNA fragment of lmWAPStat consisting of the Pac I to Not I (~2.4 kbp) cDNA fragment. Hybridization is carried out at 68° C. for 4 hours using Quick Hyb (Stratagene; LaJolla, Calif.). Following standard washing methods, the membrane is subjected to autoradiography (–70° C.) for a period of 24 hours. Transgenic mice carrying the Stat gene are identified by the presence of a ~2.4 kbp size band. Screening for the MPXKI construct: 10 mg of DNA isolated from tail tissue is digested with the endonuclease Kpn I and subjected to agarose gel electrophoresis and transferred to a nylon membrane. The membrane is probed with a $^{32}P$ labeled DNA fragment of MPXKI consisting of the Kpn I (~0.8 kbp) cDNA fragment. Hybridization is carried out at 6° C. for 4 hours using Quick Hyb (Stratagene; LaJolla, Calif.). Following standard washing methods, the membrane is subjected to autoradiography (–70° C.) for a period of 24 hours. Transgenic mice carrying the MPXKI gene are identified by the presence of a ~0.8 kbp size band.

Example 24

Production of Transgenic Mice that Express the XKI cDNA using the Multi Gene System with SMWStat and MPXKI DNA Sequences Step 1. Mice transgenic for SMWStat and MPXKI are produced essentially as described in Example 22.

Step 2. Mice produced after embryo transfer of microinjected embryos are screened by Southern analysis. Screening for the smWAPStat construct: 10 mg of DNA isolated from tail tissue is digested with the endonucleases Pac I and Not I and subjected to agarose gel electrophoresis and transferred to a nylon membrane. The membrane is probed with a $^{32}P$ labeled DNA fragment of SMWStat consisting of the Pac I to Not I (~2.4 kbp) cDNA fragment. Hybridization is carried out at 68° C. for 4 hours using Quick Hyb (Stratagene; LaJolla, Calif.). Following standard washing methods, the membrane is subjected to autoradiography (–70° C.) for a period of 24 hours. Transgenic mice carrying the Stat gene are identified by the presence of a ~2.4 kbp size band. Screening for the MPXKI construct: 10 mg of DNA isolated from tail tissue is digested with the endonuclease Kpn I and subjected to agarose gel electrophoresis and transferred to a nylon membrane. The membrane is probed with a $^{32}P$ labeled DNA fragment of MPXKI consisting of the Kpn I (~0.8 kbp) cDNA fragment. Hybridization is carried out at 680° C. for 4 hours using Quick Hyb (Stratagene; LaJolla, Calif.). Following standard washing methods, the membrane is subjected to autoradiography (−70° C.) for a period of 24 hours. Transgenic mice carrying the MPXKI gene are identified by the presence of a −0.8 kbp size band.

Example 25

Production of Transgenic Pigs that Express the XKI cDNA using the Multi Gene System with SMWStat and MPXKI DNA Sequences Step 1. Pigs transgenic for SMWStat and MPXKI are produced essentially as described in Example 23.

Step 2. Pigs produced after embryo transfer of microinjected embryos are screened by Southern analysis. Screening for the SMWStat construct: 10 mg of DNA isolated from tail tissue is digested with the endonucleases Pac I and Not I and subjected to agarose gel electrophoresis and transferred to a nylon membrane. The membrane is probed with a $^{32}$P labeled DNA fragment of SMWStat consisting of the Pac I to Not I (~2.4 kbp) cDNA fragment. Hybridization is carried out at 68° C. for 4 hours using Quick Hyb (Stratagene; LaJolla, Calif.). Following standard washing methods, the membrane is subjected to autoradiography (−70° C.) for a period of 24 hours. Transgenic mice carrying the Stat gene are identified by the presence of a ~2.4 kbp size band. Screening for the MPXKI construct: 10 mg of DNA isolated from tail tissue is digested with the endonuclease Kpn I and subjected to agarose gel electrophoresis and transferred to a nylon membrane. The membrane is probed with a $^{32}$P labeled DNA fragment of MPXKI consisting of the Kpn I (~0.8 kbp) cDNA fragment. Hybridization is carried out at 68° C. for 4 hours using Quick Hyb (Stratagene; LaJolla, Calif.). Following standard washing methods, the membrane is subjected to autoradiography (−700° C.) for a period of 24 hours. Transgenic mice carrying the MPXKI gene are identified by the presence of a ~0.8 kbp size band.

Example 26

Production of Transgenic Mice that Express the XKI cDNA using the Multi Gene System with LMWGR and MPXKI DNA Sequences Step 1. Mice transgenic for LMWGR and MPXKI are produced essentially as described in Example 22.

Step 2. Mice produced after embryo transfer of microinjected embryos are screened by Southern analysis. Screening for the LMWGR construct: 10 mg of DNA isolated from tail tissue is digested with the endonucleases Kpn I and subjected to agarose gel electrophoresis and transferred to a nylon membrane. The membrane is probed with a $^{32}$P labeled DNA fragment of LMWGR consisting of the Kpn I (~1.6 kbp) cDNA fragment. Hybridization is carried out at 68° C. for 4 hours using Quick Hyb (Stratagene; LaJolla, Calif.). Following standard washing methods, the membrane is subjected to autoradiography (−70° C.) for a period of 24 hours. Transgenic mice carrying the GR gene are identified by the presence of a −1.6 kbp size band. Screening for the MPXKI construct, 10 mg of DNA isolated from tail tissue is digested with the endonuclease Kpn I and subjected to agarose gel electrophoresis and transferred to a nylon membrane. The membrane is probed with a $^{32}$P labeled DNA fragment of MPXKI consisting of the Kpn I (~0.8 kbp) cDNA fragment. Hybridization is carried out at 68° C. for 4 hours using Quick Hyb (Stratagene; LaJolla, Calif.). Following standard washing methods, the membrane is subjected to autoradiography (−70° C.) for a period of 24 hours. Transgenic mice carrying the MPXKI gene are identified by the presence of a −0.8 kbp size band.

Example 27

Production of Transgenic Pigs that Express the XKI cDNA using the Multi Gene System with LMWGR and MPXKI DNA Constructs Step 1. Pigs transgenic for LMWGR and XKI are produced essentially as described in Example 23.

Step 2. Pigs produced after embryo transfer of microinjected embryos are screened by Southern analysis. Screening for the LMWGR construct: 10 mg of DNA isolated from tail tissue is digested with the endonuclease Kpn I and subjected to agarose gel electrophoresis and transferred to a nylon membrane. The membrane is probed with a $^{32}$P labeled DNA fragment of LMWGR consisting of the Kpn I (~2.4 kbp) cDNA fragment. Hybridization is carried out at 68 C for 4 hours using Quick Hyb (Stratagene; LaJolla, Calif.). Following standard washing methods, the membrane is subjected to autoradiography (−70 C) for a period of 24 hours. Transgenic pigs carrying the GR gene are identified by the presence of a 1.6 kbp size band. Screening for the XKI construct: 10 mg of DNA isolated from tail tissue is digested with the endonuclease Kpn I and subjected to agarose gel electrophoresis and transferred to a nylon membrane. The membrane is probed with a $^{32}$P labeled DNA fragment of MPXKI consisting of the Kpn I (~0.8 kbp) cDNA fragment. Hybridization is carried out at 68° C. for 4 hours using Quick Hyb (Stratagene; LaJolla, Calif.). Following standard washing methods, the membrane is subjected to autoradiography (−70° C.) for a period of 24 hours. Transgenic pigs carrying the MPXKI gene are identified by the presence of a ~0.8 kbp size band.

What is claimed is:

1. A method of producing one or more peptides or proteins in a transgenic non-human mammal, wherein said mammal comprises multiple exogenous DNA sequences stably integrated in its genome, wherein the method does not require the administration of an exogenous induction factor or ligand, wherein said method comprises:
    A) providing said transgenic non-human mammal, wherein said mammal comprises multiple exogenous DNA sequences stably integrated in its genome comprising:
    (1) an exogenous DNA sequence of type A, said type A DNA sequence comprising:
        (a) 5' regulatory sequences including a milk protein promoter operably linked to the DNA of (b),
        (b) DNA encoding a non-secreted transactivating protein, wherein said non-secreted transactivating protein contains a DNA binding domain which recognizes the DNA binding site in a type B DNA sequence, and possesses transactivating activity, and
        (c) 3' regulatory sequences active in the transgenic non-human mammal; and
    (2) one or more exogenous DNA sequences of type B, said type B DNA sequence or each type B DNA sequence comprising:
        (d) a DNA binding site recognized by the DNA binding domain of said non-secreted transactivating protein, operably linked to a minimal promoter operably linked to the DNA of(e),
        (e) DNA encoding a peptide or protein, and
        (f) 3' regulatory sequences active in the transgenic non-human mammal, wherein said multiple exogenous DNA sequences are effective in directing the secretion of the peptide or protein into milk of said transgenic non-human mammal, wherein said milk protein promoter and said minimal promoter are different promoters;

B) allowing the peptide or protein to be produced and secreted into the milk of the transgenic non-human mammal; and C) collecting and purifying the peptide(s) or protein(s).

2. The method of claim 1 wherein said milk protein promoter is selected from the group consisting of whey acidic protein (WAP) promoter, α-casein promoter, β-casein promoter, κ-casein promoter, α-lactalbumin promoter, lactoferrin promoter and β-lactoglobulin promoter.

3. The method of claim 2 wherein said milk protein promoter is the WAP promoter.

4. The method of claim 1 wherein said non-human transgenic mammal is selected from the group consisting of mouse, rat, rabbit, pig, goat, sheep and cow.

5. The method of claim 1 wherein said 3' regulatory sequences are chosen to function efficiently with said milk protein promoter.

6. The method of claim 5 wherein said 3' regulatory sequences are from a milk protein gene.

7. The method of claim 6 wherein said 3' regulatory sequences are from a WAP gene.

8. The method of claim 1 wherein said minimal promoter contains a TATA box and a transcriptional start site.

9. The method of claim 8 wherein said minimal promoter contains a TATA box, a transcriptional start site and other 5' regulatory sequences to boost expression level.

10. The method of claim 1 wherein the said DNA binding site is the binding site of the GAL 4 DNA binding protein.

11. The method of claim 1 wherein said peptide or protein can be any secreted peptide or protein of therapeutic or industrial importance.

12. The method of claim 11 wherein said protein is a fusion protein containing the light chain of factor X (X) combined with the $1^{st}$ Kunitz domain of Tissue Factor Plasminogen Inhibitor (TFPI-KI) designated XKI.

13. The method of claim 11 wherein said protein is a fusion protein containing the propeptide of factor IX (9) and the light chain of factor X (X) combined with the $1^{st}$ Kunitz domain of Tissue Factor Plasminogen inhibitor (TFPI-KI) designated 9XKI.

14. The method of claim 11 wherein said protein is a fusion protein containing the propeptide of factor IX combined with the mature peptide of protein C, designated 9PC.

15. The method of claim 11 wherein said protein is a fusion protein containing the propeptide of factor VII combined with the mature peptide of protein C, designated 7PC.

16. The method of claim 11 wherein said protein is a fusion protein containing the propeptide of factor X combined with the mature peptide of protein C, designated 10PC.

17. The method of claim 1, wherein said non-secreted transactivating protein is a modified glucocorticoid receptor (GR), containing a DNA binding domain which recognizes the DNA binding site in a type B gene and possesses transactivating activity.

18. The method of claim 2, wherein said non-secreted transactivating protein is a modified Stat5 transcription factor, containing a DNA binding domain which recognizes the DNA binding site in a type B gene and possesses transactivating activity.

19. The method of claim 17 or 18 wherein said non-secreted transactivating protein is further modified to contain an enhanced transactivating activity by the addition of extra transactivation domains.

20. The method of claim 19 wherein said extra transactivation domain is selected from the group consisting of TAF-1, TAF-2, TAU-1, TAU-2, VP16 and $NF_\kappa B$-P65.

21. The method of claim 17 or 18 wherein the said DNA binding site is the binding site of the GAL 4 DNA binding protein.

22. The method of claim 17 or 18 wherein said milk protein promoter is selected from the group consisting of whey acidic protein (WAP) promoter, α-casein promoter, β-casein promoter, κ-casein promoter, α-lactalbumin promoter, lactoferrin promoter and β-lactoglobulin promoter.

23. The method of claim 22 wherein said milk protein promoter is the WAP promoter.

24. The method of claim 22 wherein said non-human transgenic mammal is selected from the group consisting of mouse, rat, rabbit, pig, goat, sheep and cow.

25. The method of claim 22 wherein said 3' regulatory sequences are chosen to function efficiently with said milk protein promoter.

26. The method of claim 25 wherein said 3' regulatory sequences are from a milk protein gene.

27. The method of claim 26 wherein said 3' regulatory sequences are from a WAP gene.

28. The method of claim 17 or 18 wherein said minimal promoter contains a TATA box and a transcriptional start site.

29. The method of claim 28 wherein said minimal promoter contains a TATA box, a transcriptional start site and other 5' regulatory sequences to boost expression level.

30. The method of claim 17 or 18 wherein said peptide or protein can be any secreted peptide or protein of therapeutic or industrial importance.

31. The method of claim 30 wherein said desired protein is a fusion protein containing the light chain of factor X (X) combined with the $1^{st}$ Kunitz domain of Tissue Factor Plasminogen Inhibitor (TFPI-KI) designated XKI.

32. The method of claim 30 wherein said desired protein is a fusion protein containing the propeptide of factor IX (9) and the light chain of factor X (X) combined with the $1^{st}$ Kunitz domain of Tissue Factor Plasminogen Inhibitor (TFPI-KI), designated 9XKI.

33. The method of claim 30 wherein said desired protein is a fusion protein containing the propeptide of factor IX combined with the mature peptide of protein C, designated 9PC.

34. The method of claim 30 wherein said desired protein is a fusion protein containing the propeptide of factor VII combined with the mature peptide of protein C, designated 7PC.

35. The method of claim 30 wherein said desired protein is a fusion protein containing the propeptide of factor X combined with the mature peptide of protein C, designated 10PC.

36. The method of claim 1, wherein said protein encoded by the DNA of (2)(e) is a vitamin K dependent (VKD) protein.

37. The method of claim 9, wherein the 5' regulatory sequences are selected from the group consisting of a CCAAT box or a CACCC box.

38. The method of claim 29, wherein the 5' regulatory sequences are selected from the group consisting of a CCAAT box or a CACCC box.

* * * * *